United States Patent [19]
Brownlee

[11] Patent Number: 4,927,265
[45] Date of Patent: May 22, 1990

[54] DETECTOR FOR FLUORESCENCE AND ABSORPTION SPECTROSCOPY

[75] Inventor: Robert G. Brownlee, Los Altos Hills, Calif.

[73] Assignee: 501 Microphoretic Systems, Inc., Sunnyvale, Calif.

[21] Appl. No.: 187,789

[22] Filed: Apr. 29, 1988

[51] Int. Cl.[5] .................. G01N 21/31; G01N 21/64
[52] U.S. Cl. .................. 356/73; 356/72
[58] Field of Search .................. 356/73, 72

[56] References Cited

U.S. PATENT DOCUMENTS

| | | | |
|---|---|---|---|
| 3,920,334 | 11/1975 | Steichen et al. | 356/73 |
| 4,145,139 | 3/1979 | Nakamura et al. | 356/73 |
| 4,699,510 | 10/1987 | Alguard | 356/73 |
| 4,730,922 | 3/1988 | Bach et al. | 356/73 |

OTHER PUBLICATIONS

J. L. Beckers et al., "Use of a Double Detector System for the Measurement of Mobilities in Zone Electrophoresis," Journal of Chromatography, vol. 452, pp. 591-600, 1988.

Y. F. Cheng et al., "Subattomole Amino Acid Analysis by Capillary Zone Electrophoresis and Laser-Induced Fluorescence" Science, vol. 242, Oct. 1988, pp. 563-564.

F. Foret et al., "On-Line Fiber Optic UV Detection Cell and Conductivity Cell for Capillary Zone Electrophoresis", vol. 7, pp. 430-432, 1986.

J. R. Gant et al., "A Low-Cost LC System With Trifunctional Detector", American Laboratory, pp. 104-111, Mar. 1985.

J. S. Green et al., "Variable-Wavelength On-Column Fluorescence Detector for Open-Tubular Zone Electrophoresis" Journal of Chromatography, vol. 352, pp. 337-343, 1986.

M. Goto et al., "Multichannel Spectrophotometric Detector for Fused-Silica Capillary Isotachophoresis", Journal of Chromatography, vol. 346, pp. 167-176, 1985.

J. W. Jorgenson et al., "Capillary Zone Electrophoresis", Science, vol. 222, pp. 266-272, Oct. 1983.

J. W. Jorgenson et al., "Zone Electrophoresis in Open-Tubular Glass Capillaries", Analytical Chemistry, vol. 53, No. 8, pp. 1298-1301, Jul. 1981.

H. H. Lauer et al., "Capillary Zone Electrophoresis of Proteins in Untreated Fused Silica Tubing", Analytical Chemistry, vol. 58, No. 1, pp. 166-170, Jan. 1986.

Z. Prusik et al., Experimental Device for Electrokinetic Micellar Chromatography Exploiting Some Components of Capillary . . . , Journal of Chromatography, vol. 390, pp. 87-96, 1987.

G. J. Schmidt et al., "A Multifunctional Liquid Chromatographic Detector, Analyst", vol. 110, pp. 757-760, Jul. 1985.

Y. Walbroehl et al., "On-Column UV Absorption Detector for Open Tubular Capillary Zone Electrophoresis", Journal of Chromatography, vol. 315, pp. 135-143, 1984.

*Primary Examiner*—Vincent P. McGraw
*Attorney, Agent, or Firm*—Fliesler, Dubb, Meyer & Lovejoy

[57] ABSTRACT

Automated capillary electrophoresis tests can be performed using the capillary electrophoresis instrument of this invention. The capillary electrophoresis instrument has means for automatically purging and replenishing electrolytes, for automatically entering a sample into the capillary tube and for automatically performing capillary electrophoresis. A detector for simultaneous detection of absorbance and fluorescence provides means for quantifing the species separated by electrophoresis.

21 Claims, 42 Drawing Sheets

4/42

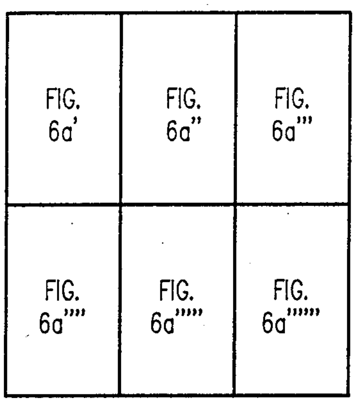
KEY TO FIG. 6a
FIG. 6a'
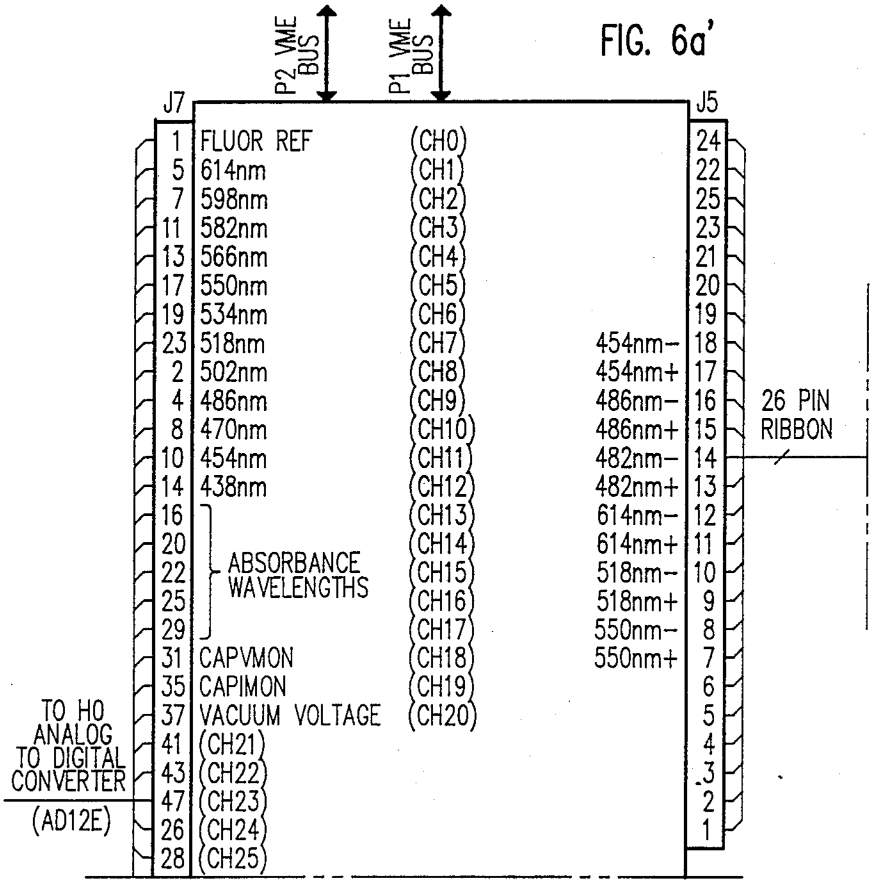

FIG. 6a"
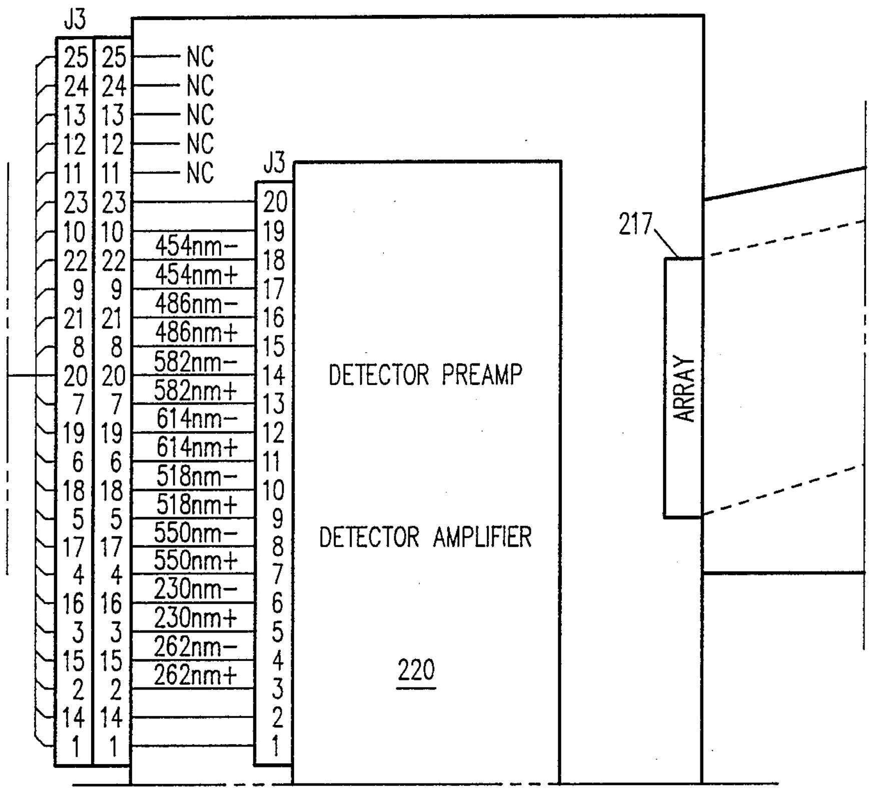

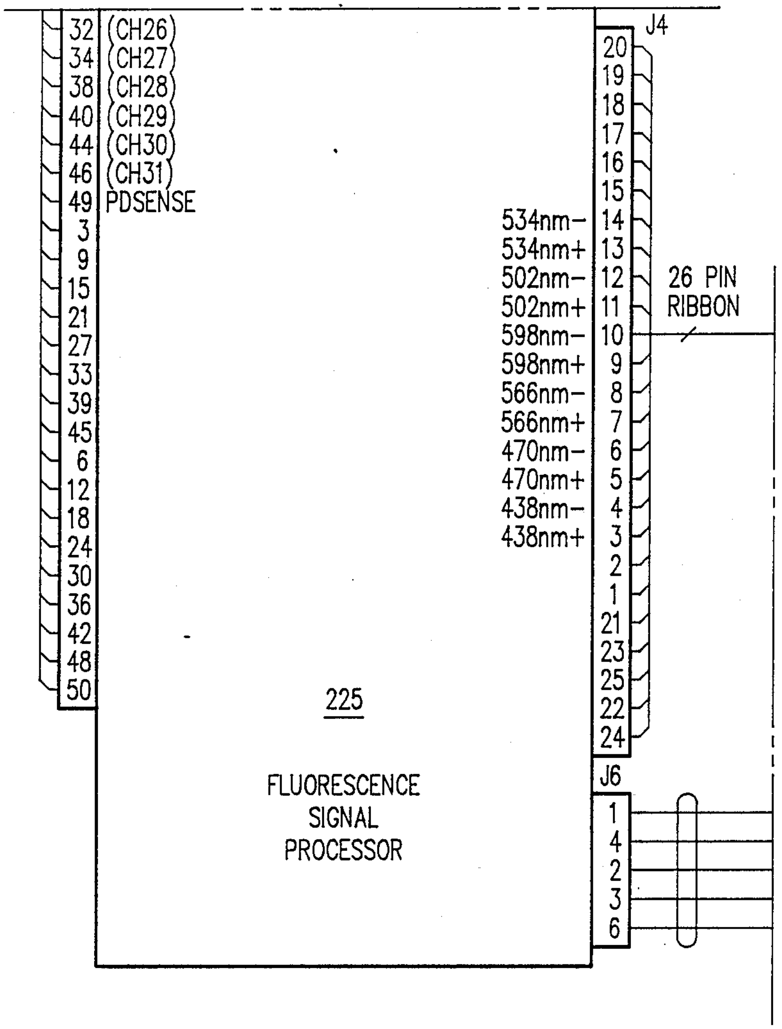
FIG. 6a''''

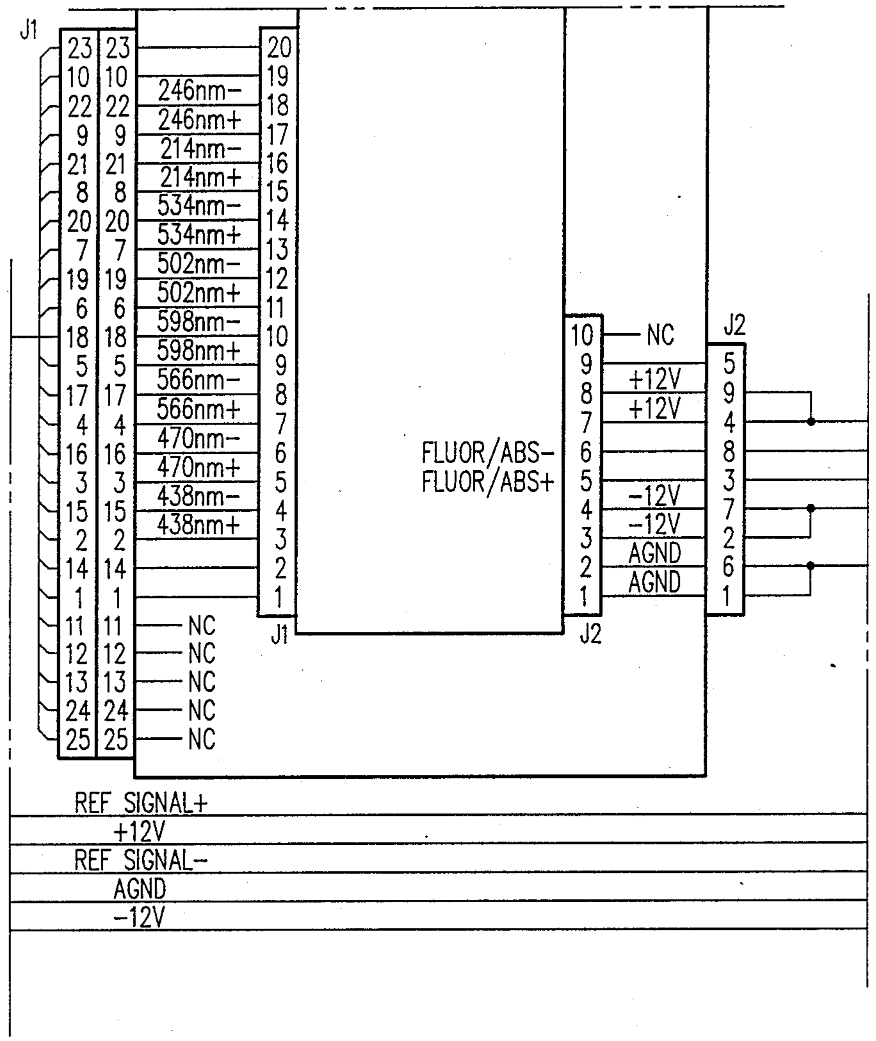
FIG. 6a'''''

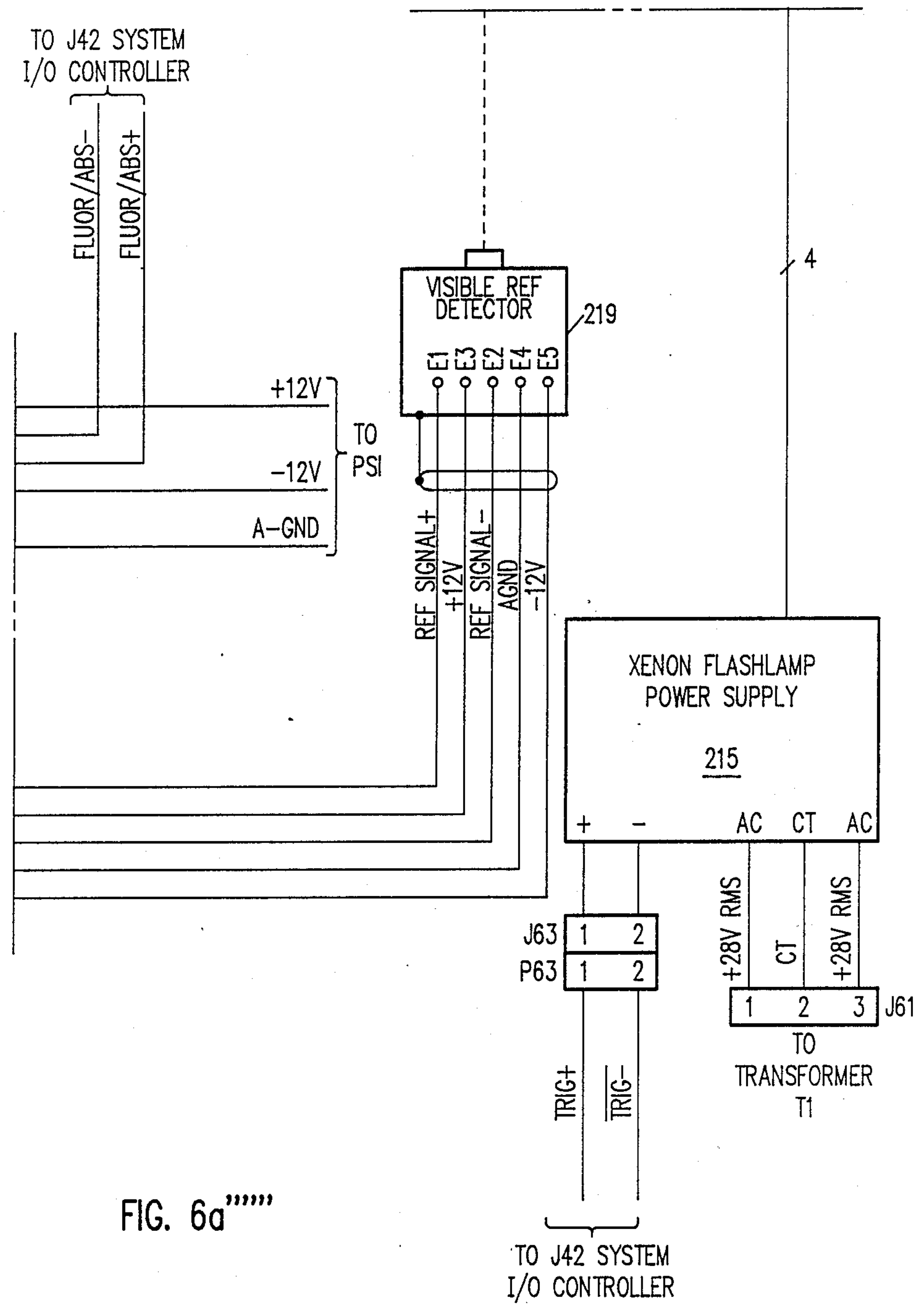
FIG. 6a'''''''

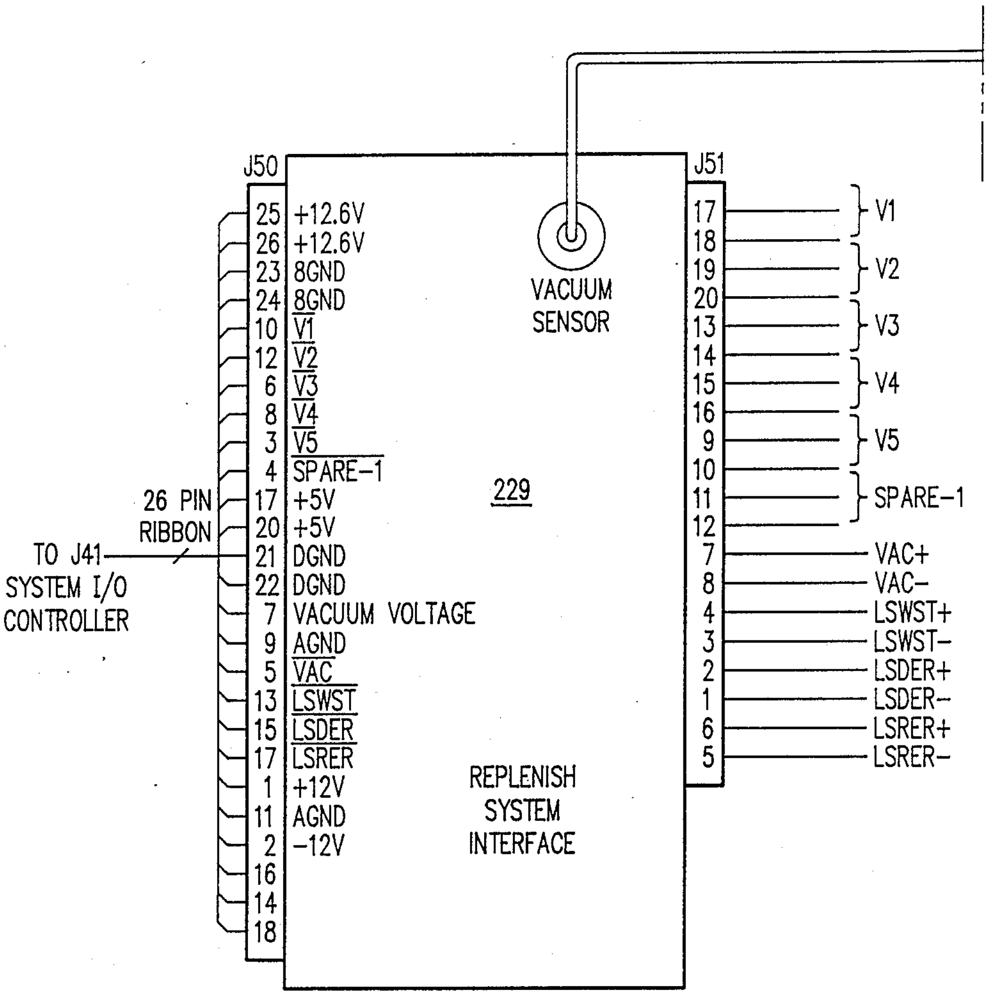
FIG. 6b'
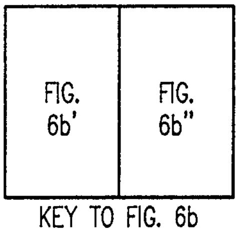
KEY TO FIG. 6b

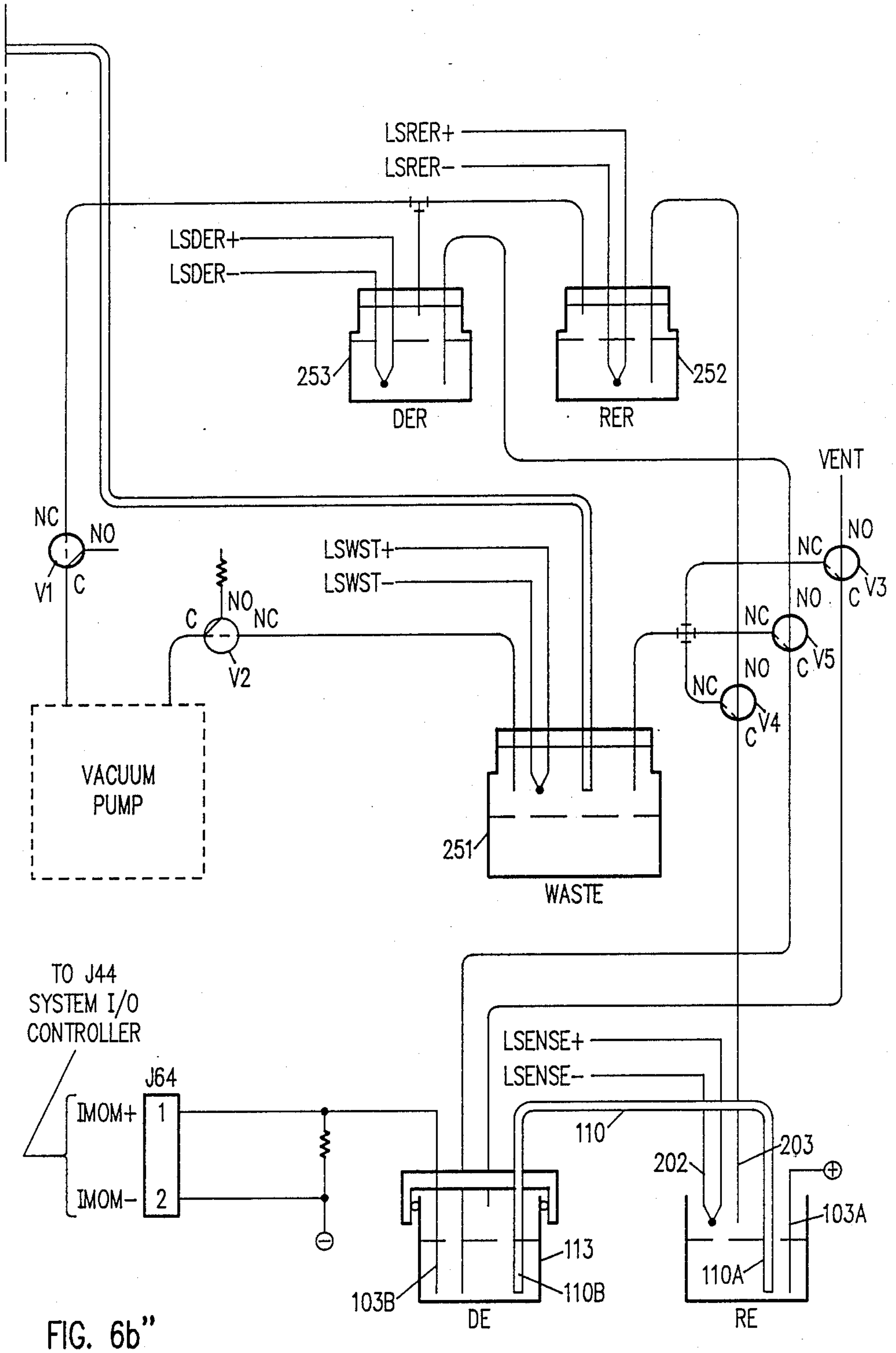
FIG. 6b"

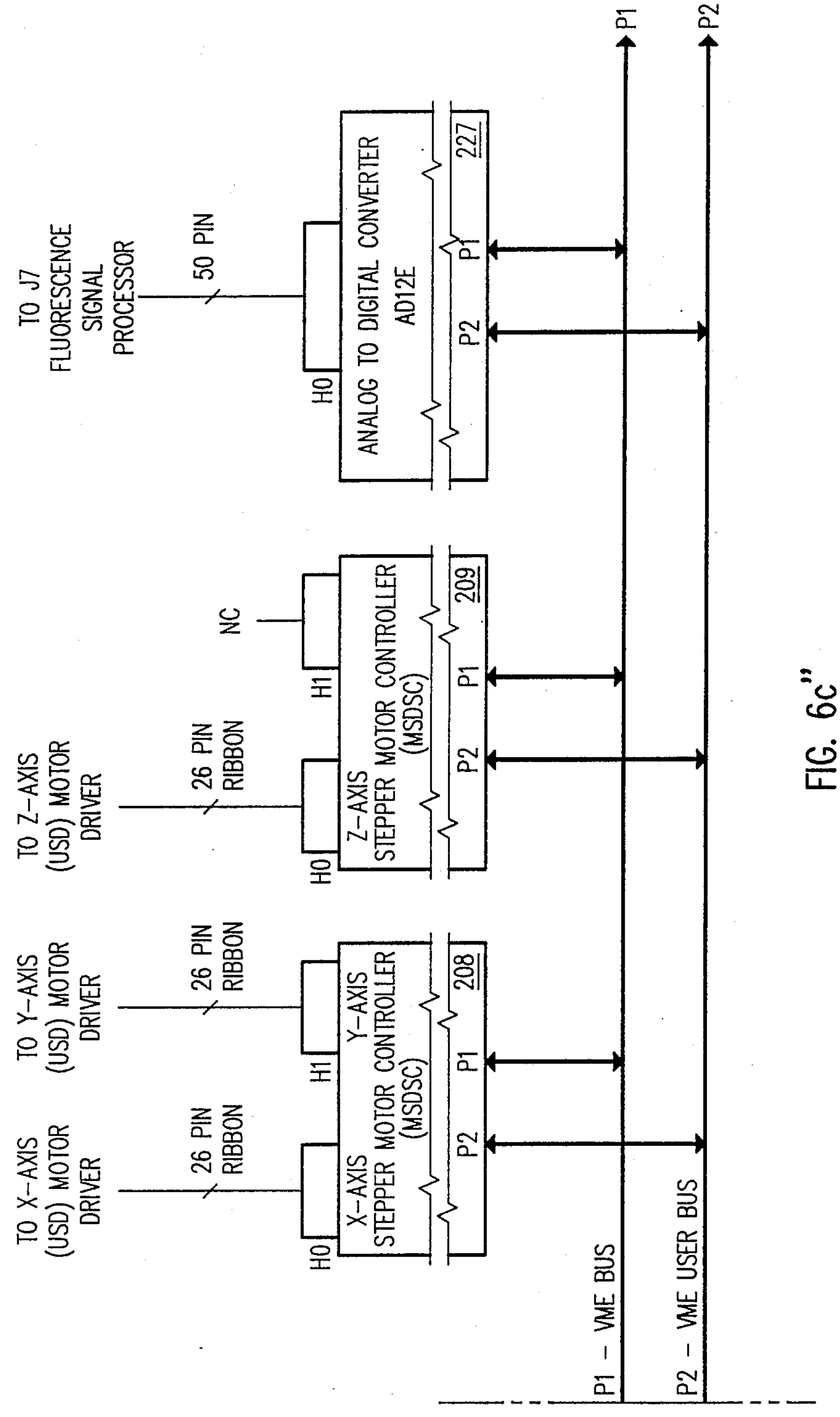
FIG. 6c"

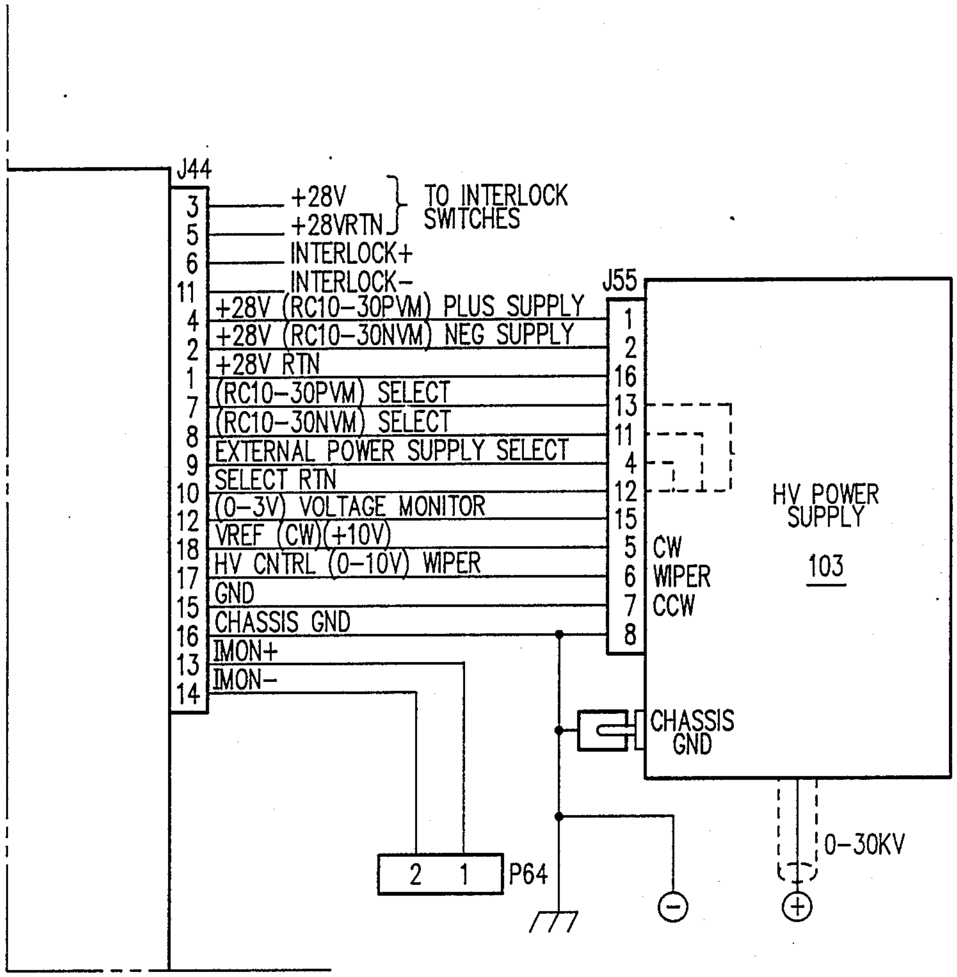
FIG. 6d"

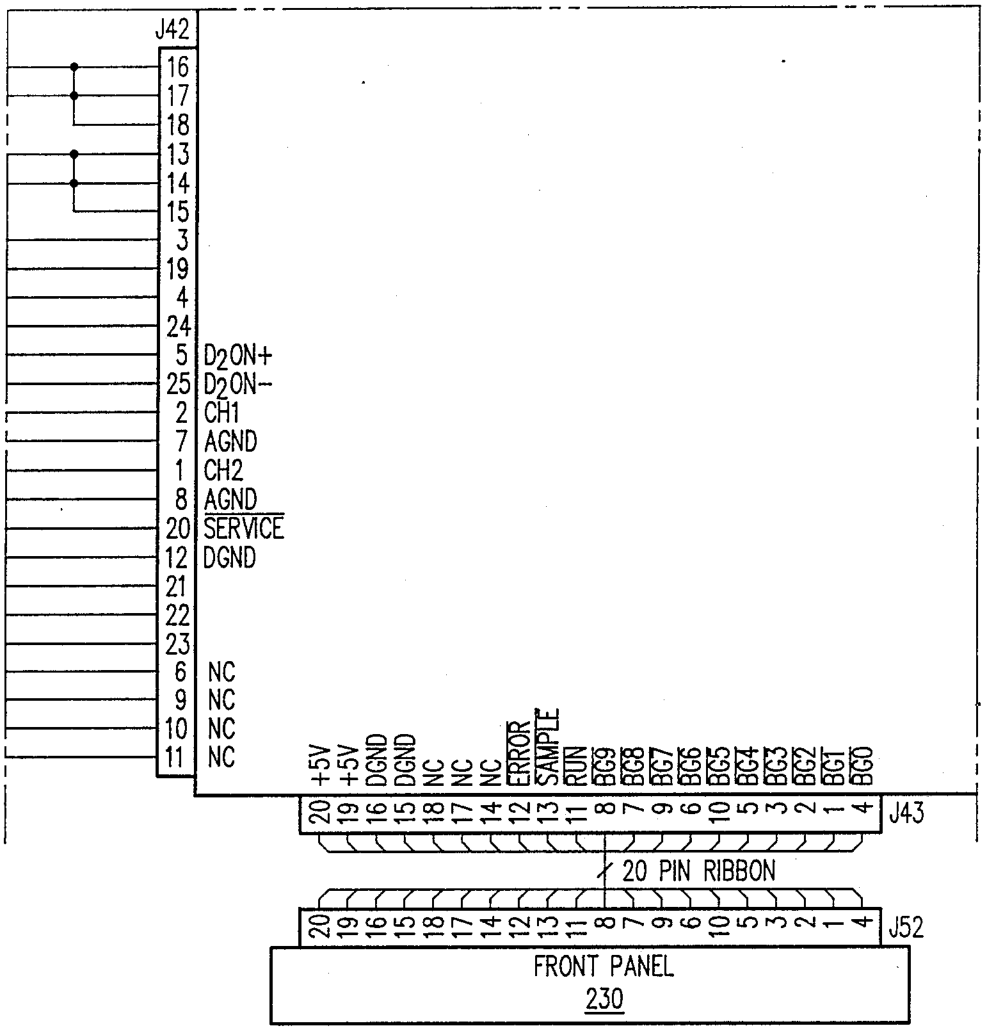
FIG. 6d''''

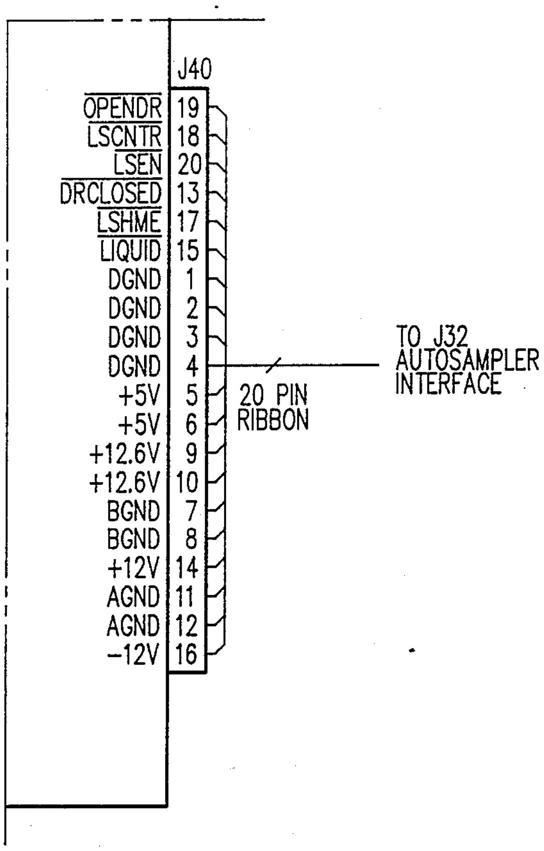
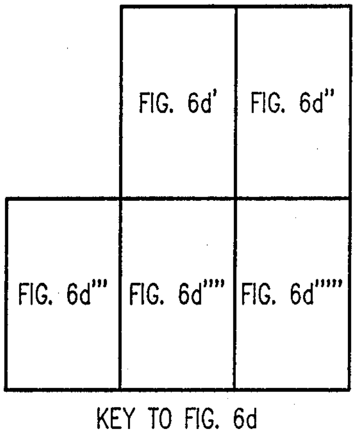
KEY TO FIG. 6d
FIG. 6d'''''

SECTION A–A

SECTION B–B

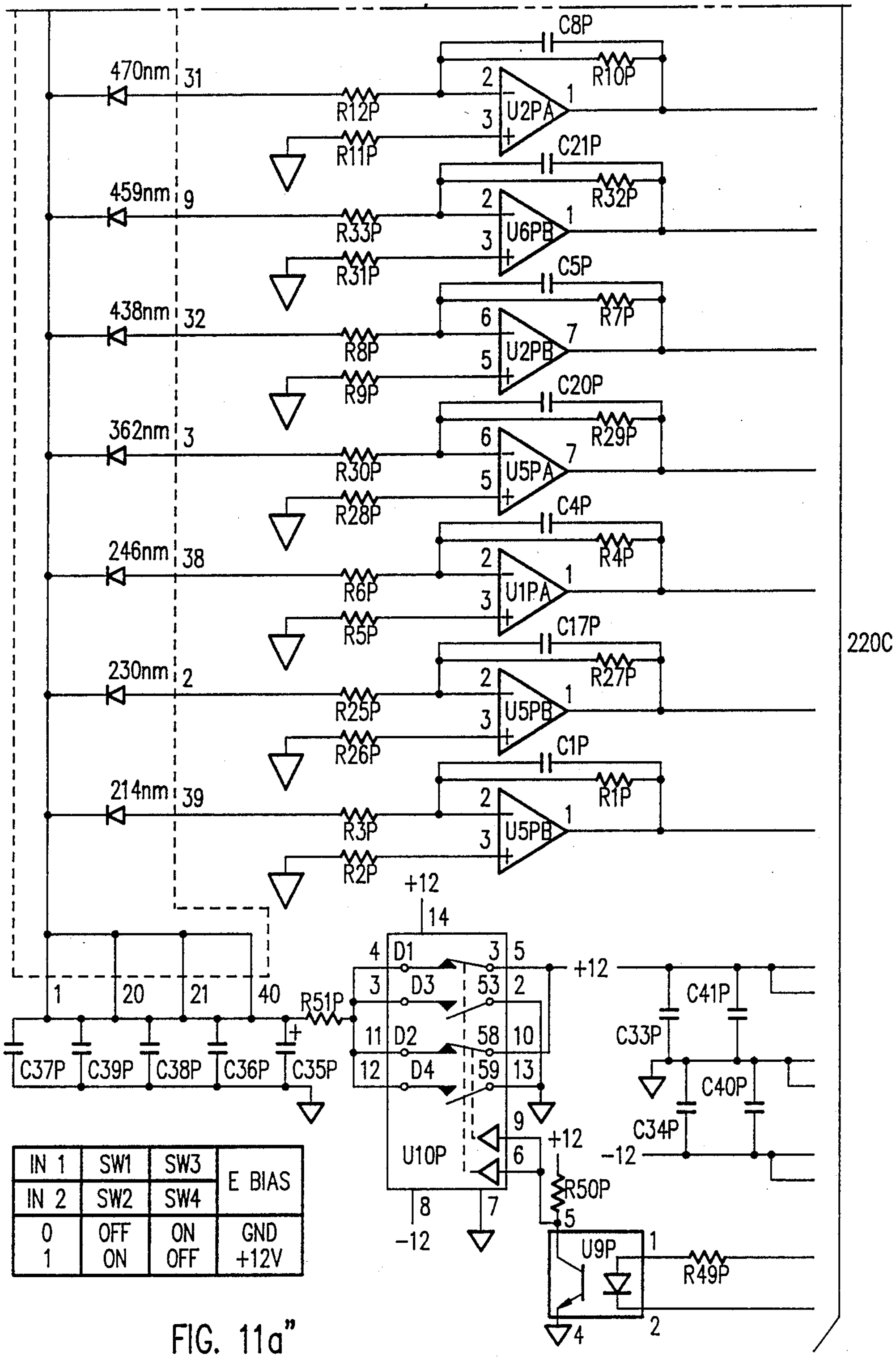
| IN 1 | SW1 | SW3 | E BIAS |
|---|---|---|---|
| IN 2 | SW2 | SW4 | |
| 0 | OFF | ON | GND |
| 1 | ON | OFF | +12V |
FIG. 11a"

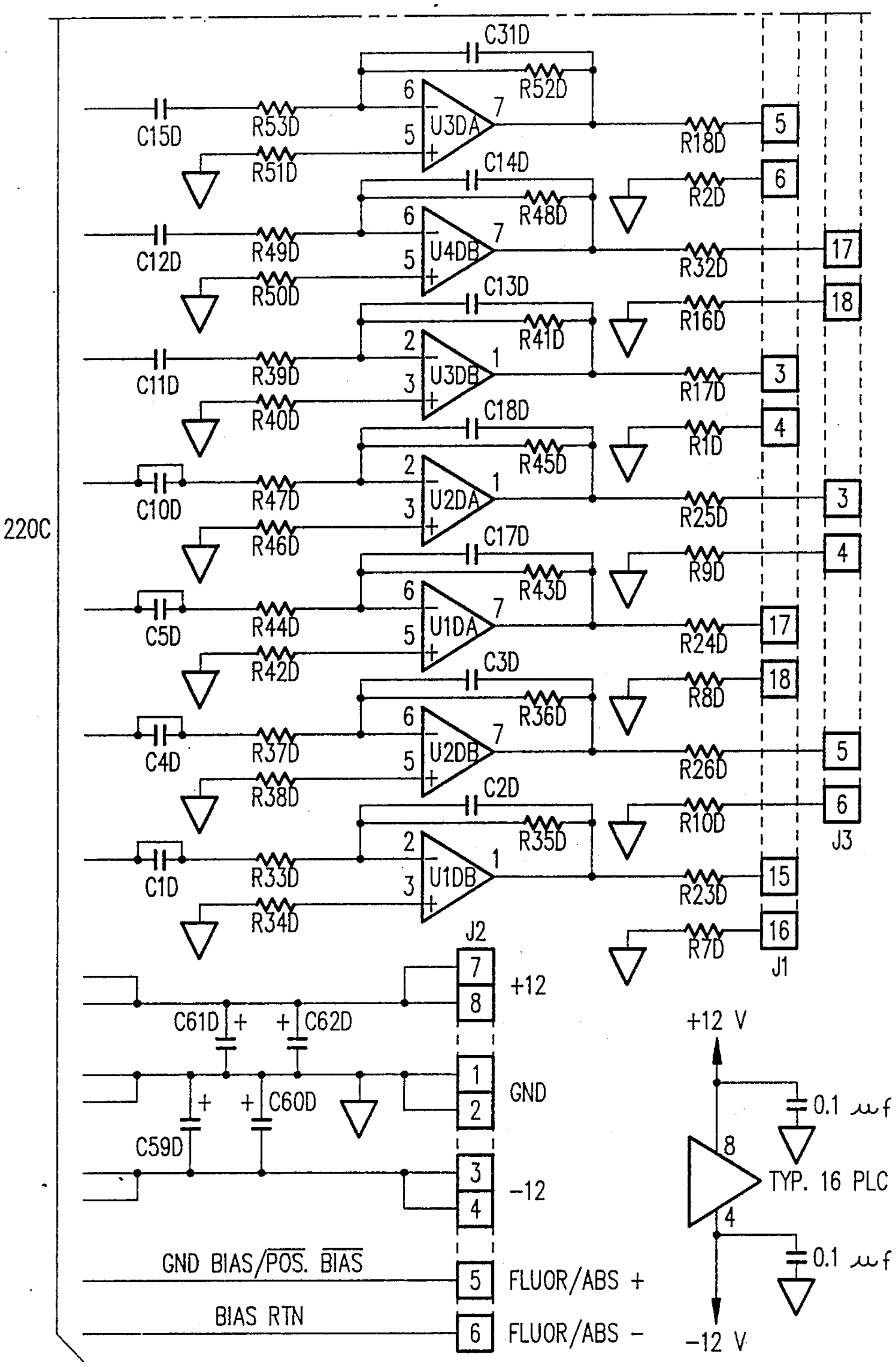
FIG. 11b"

KEY TO FIG. 12a

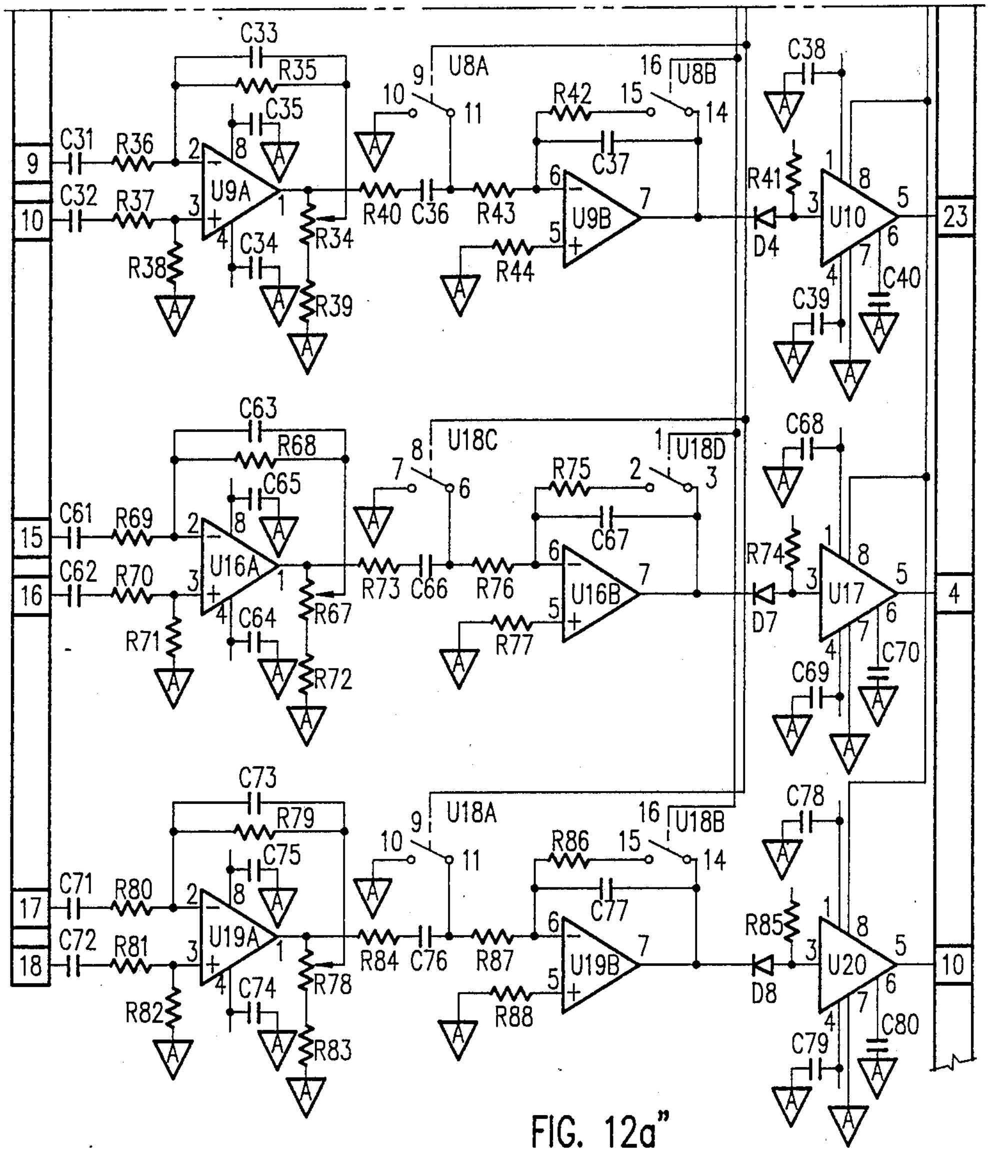
FIG. 12a"

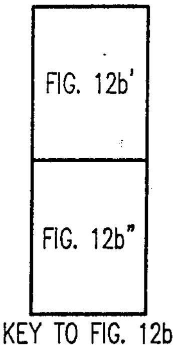
FIG. 12b'
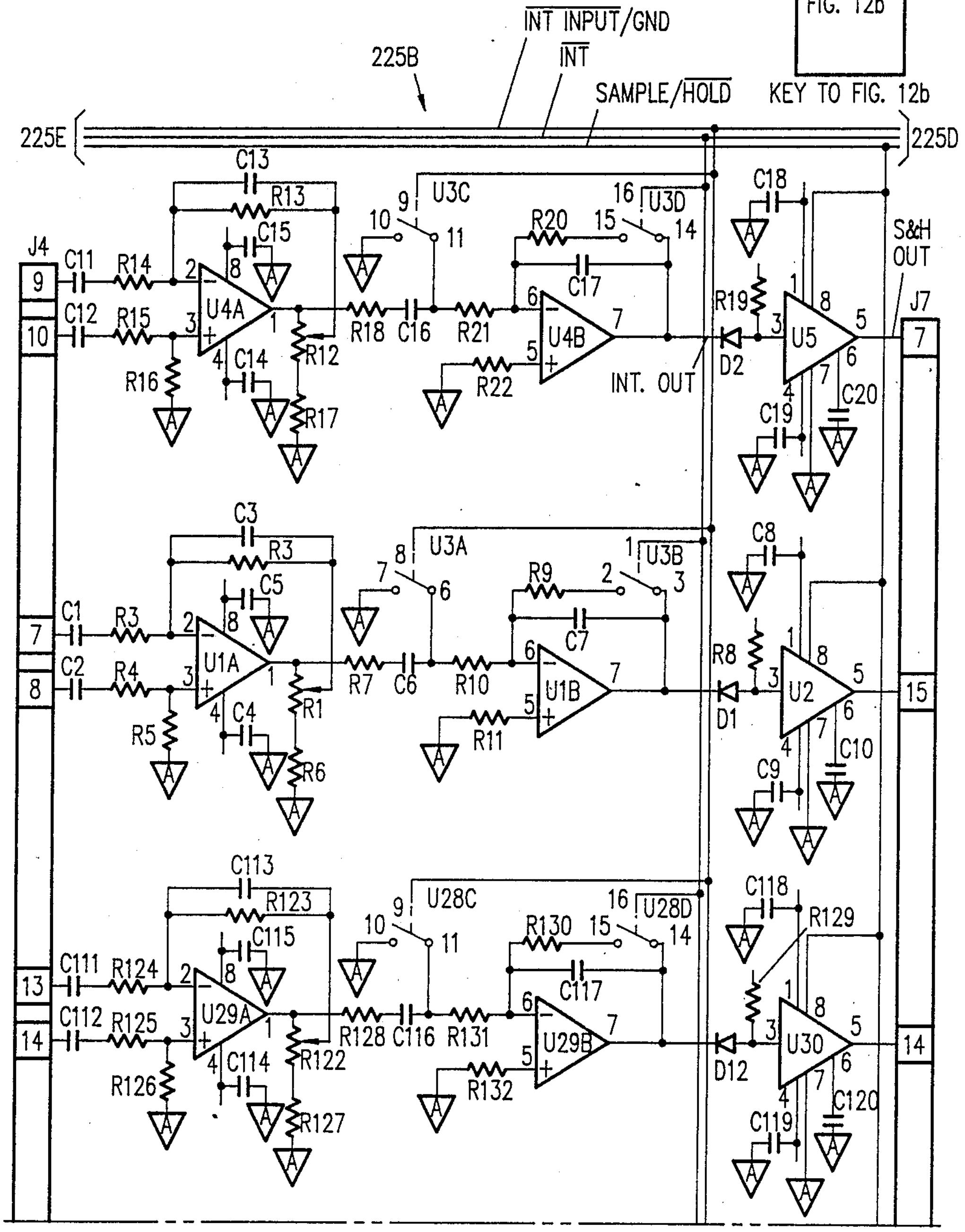

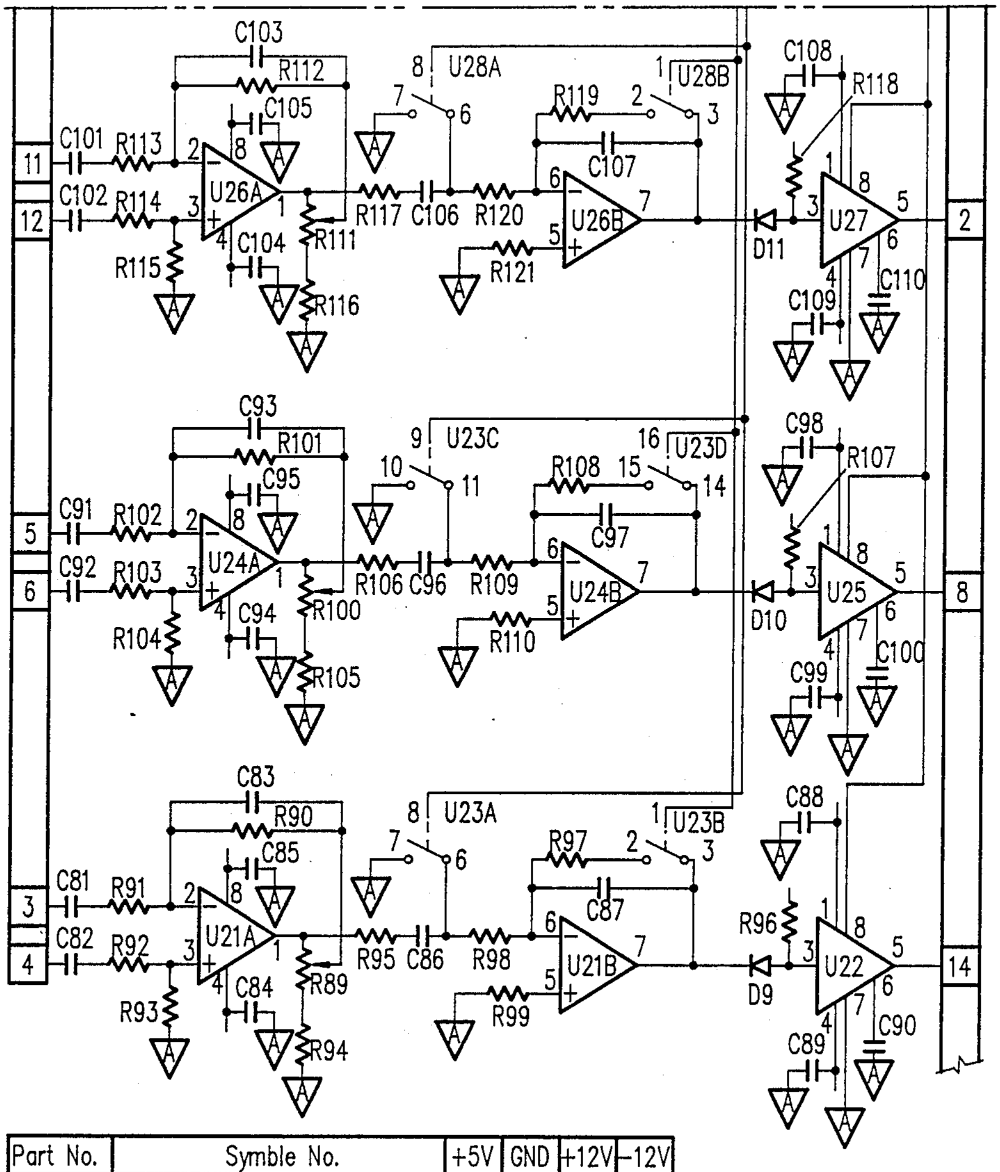
| Part No. | Symble No. | +5V | GND | +12V | -12V |
|---|---|---|---|---|---|
| OP215 | U1 U4 U6 U9 U11 U14 U16 U19 U21 U24 U26 U29 U31 | – | – | 8 | 4 |
| LF398 | U2 U5 U7 U10 U12 U15 U17 U20 U22 U25 U27 U30 U32 | – | 4 | 1 | 4 |
| DG202 | U3 U8 U13 U18 U23 U28 U33 | – | 5 | 13 | 4 |
| LM311 | U503 | – | 1 | 8 | 4 |
| 746502 | U502 | 14 | 7 | – | – |
| 746574 | U500 | 14 | 7 | – | – |
| 7465123 | U501 | 16 | 8 | – | – |
FIG. 12b"

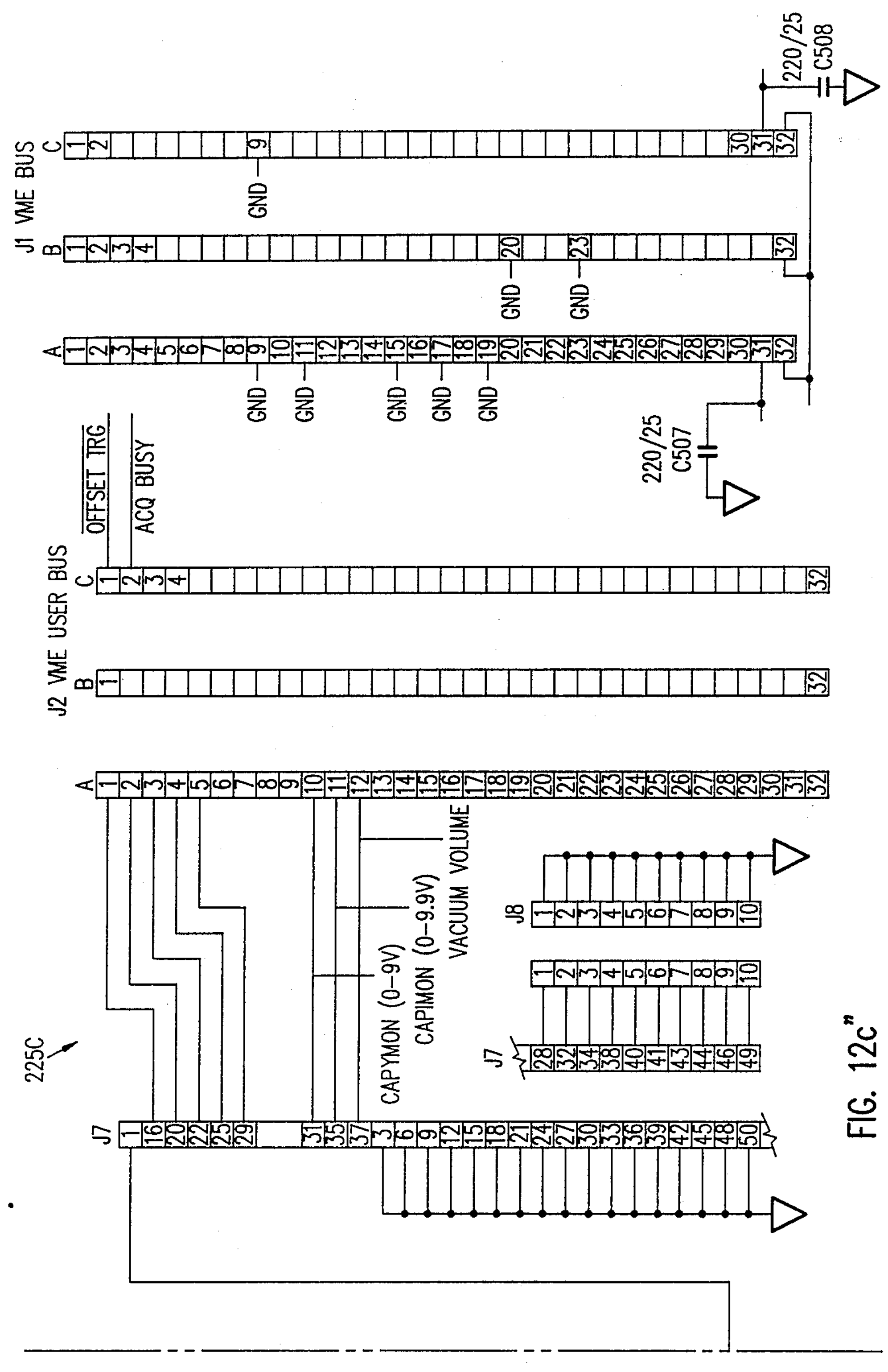
FIG. 12c"

DETECTOR FOR FLUORESCENCE AND ABSORPTION SPECTROSCOPY

RELATED APPLICATION

This application is related to U.S. patent application Ser. No. 07/187,769, entitled "An Auto-Sample System and Related Apparatus for Capillary Electrophoresis," filed by Robert G. Brownlee, assigned to the assignee of the present invention and incorporated herein by reference.

BACKGROUND OF THE INVENTION

1. Field of the Invention

The invention relates generally to a subsystem for fluorescence and absorption spectroscopy and more specifically to an apparatus for simultaneously generating absorption and fluorescent data for a single sample.

2. Description of the Prior Art

High performance liquid chromatography (HPLC), gel electrophoresis and capillary electrophoresis are all used for biochemistry applications such as separation of DNA molecules. Electrophoresis is a separation technique produced by the migration of charged molecules (or particles) in an electrolyte under the influence of an electric field. Smaller or more highly charged sample molecules move faster than larger or lower charged molecules. Hence, each species of the sample molecules is divided into bands which pass or reach a fixed point at different times.

In gel electrophoresis (GE), the electrolyte is usually supported by a porous hydrophilic polymer matrix, the gel, coated on a sheet of glass, sandwiched together with another glass plate and sealed on each side with a gasket. The samples are applied to the top edge of the gel. The bottom edge of the gel sandwich is placed vertically in a reservoir containing a buffered electrolyte. A second reservoir is placed on top of the sandwich and filled with buffered electrolyte. Each reservoir contains an electrode connected to the proper output of a DC power supply. A voltage of up to two thousand volts is applied to the sample. A typical GE run may take six hours. After the run the plate must be stained to visualize the GE bands of interest.

The success of electrophoresis in most applications depends upon the effective utilization of a stabilizing medium such as polymer gels. The gels stabilize the separation medium against convection and flow which would otherwise disrupt separations. A large body of modern electrophoresis technology is devoted to understanding and to controlling the formation of electrophoresis gels.

Gel electrophoresis, as commonly practiced, is generally not considered a true instrumental method of analysis. Instrumental versions of gel electrophoresis analogous to column chromatography are still in the developmental stages in most cases. The presence of the stabilizing gels has prevented the adaptation of electrophoresis to on-line detection quantification or automated operation and consequently gel electrophoresis is still a manual intensive methodology.

Capillary electrophoresis has been developed as an alternative to column chromatography and gel electrophoresis because capillary electrophoresis is up to ten times faster than gel electrophoresis and is more accurate. In capillary electrophoresis, the time, expense and variability of packing a chromatographic column or casting an electrophoresis gel are obviated. Small samples are separated and analyzed in a few minutes. The sharpness of separations is enhanced by the use of narrow-bore tubing, since this minimizes the thermal gradients and the consequential convective turbulence and diffusion of sample components. Capillary separations avoid the "eddy migration" problems which are encountered when stabilizing media such as electrophoretic gels or chromatographic packings are used.

A schematic of a prior art capillary electrophoresis system is illustrated in FIG. 1. A high voltage power supply 10 provides a high voltage to a first electrode 17 which is mounted in a first reservoir 16 containing an electrolyte. A first end 15 of a capillary tube 14 is also suspended in reservoir 16. A second end 13 of capillary tube 14 is mounted in a second reservoir 12 containing an electrolyte and a second electrode 11 connected to ground through power supply 10. A detector 18 is mounted around capillary tube 14.

Capillary tube 14, used to bridge the gap between two electrolyte reservoirs 12, 16, is typically a fused silica capillary tube 50 microns in diameter and about 50 cm long. Tube 14 is first filled with electrolyte and then approximately five nanoliters of sample solution are introduced at end 15 of capillary tube 14, and an ultraviolet (UV) light is passed through the diameter of the capillary tube by the detector near end 13 of tube 14. When a 20-30 KV potential is applied across capillary tube 14, electrophoresis causes all charged sample molecules to travel along capillary tube 14 at different velocities and to pass through the illuminated section of capillary tube 14 at different times. The sample molecules are detected by a photosensor placed opposite the UV light source in the case of an absorbance detector, or at right angles to the light source in the case of a fluorescence detector. All sample components whether anions, cations, or neutrals are eventually swept through the detector as peaks, sometimes called bands, and the output signals from the detector are analyzed to identify the characteristics of the sample.

Since the migration time for a species in the sample is dependent upon the length of capillary tube 14, the electrophoretic mobility of the species, and the applied voltage, species having different electrophoretic mobilities will pass through the detector at different times. The separation efficiency of the various species in the sample in terms of the total number of theoretical plates is dependent upon the mobility, the applied voltage and the diffusion coefficient. Hence, high separation efficiencies are best achieved through the use of high voltages. Also, column length plays no role in the separation efficiency but column length has an influence on the migration times and hence the time required for analysis of a sample.

The CE system, as illustrated in FIG. 1, potentially provides rapid, high resolution online detection capability that is not attainable wih gel electrophoresis equipment. Capillary electrophoresis circumvents the labor intensive manual procedures of experiment preparation, sample manipulation, data generation and interpretation which is inherent in gel or other stabilizing medium electrophoresis techniques. Further, the quantity of sample required to perform capillary electrophoresis is significantly less than that of the other methods.

A variety of methods for introducing the sample into the capillary tube have been used. Displacement techniques such as direct injection, gravity flow or siphoning and suction are commonly used since these techniques are simple and produce separations which accurately reflect the relative concentration of sample constituents. Other techniques for introducing the sample involve the principle of electromigration. In these applications, the samples are introduced into the capillary tube by a short duration electrical current. Both electrophoretic and electroendosmotic forces can contribute to the sample movement in these techniques. Devices using a sample splitter (See M. Deml, F. Foret and P. Bocek, "Electric Sample Splitter for Capillary Zone Electrophoresis," *J. Chrom.* 346 pp. 159–165 (1985)), a micro injector (See R. A. Wallingford and A. G. Ewing, "Characterization of a Micro Injector for Capillary Electrophoresis," *Anal. Chem.* 59, pp. 678–681 (1987)), and a rotary injector (See T. Tsuda, T. Mizuno, and J. Akiyama, "Rotary-Type Injector for Capillary Zone Electrophoresis," *Anal. Chem.* 59, pp. 799–800 (1987)) have been reported.

In capillary electrophoresis separations utilizing electroendosmotic flow, the sample components are introduced at the high voltage anode side of the apparatus. This is the opposite of most conventional electrophoretic techniques.

Fused silica is most commonly used for electrophoretic capillaries. Capillary tube inner diameters of 50–100 microns with wall thicknesses of less than 200 microns are used in most applications. Capillary lengths of 10–100 centimeters are most often used. While as described above, the species separation is theoretically independent of capillary length, and a shorter tube would seem advantageous in minimizing band broadening caused by diffusion and sample interactions. Practical considerations of Joule heat dissipation dictate the length of the capillary tube.

The regulated direct current high voltage power supplies have had potentials up to 50 kilovolts. These voltages generate microamp currents through the capillary tube. Again, while the theoretical considerations indicate that faster separations are obtained with higher voltage potentials, there are practical limits imposed by heat dissipation requirements. In addition, excessively high voltages may result in corona discharge through the capillary tube and elsewhere within the instrument.

The small scale of analysis in capillary electrophoresis requires ultra-sensitive detection instrumentation. Hence, no convenient universal detector for every conceivable type of sample molecule exists. Multiple detection methodologies have been used. Capillaries have been used for years in "on-column" detection among several areas of the separation sciences, most notably, liquid and gas chromatography. Hence, much of the detection instrumentation for capillary electrophoresis is drawn from these areas. Ultraviolet wave length detectors are commonly used for analysis of amino acids, peptides, proteins, nucleics components, as well as some carbohydrates, drugs and other molecules of biological significance. In one prior art application, capillary electrophoresis zone detection was accomplished with fluorescence detectors and ultraviolet absorption detectors. Both detectors were separately used in an on-column mode (See J. W. Jorgenson and K. D. Lukacs, "Capillary Zone Electrophoresis," Science, Vol. 222, pp. 266–272, Oct. 21, 1983).

Commercial absorption detectors and fluorescence detectors are available which may be modified for use in capillary electrophoresis. In one prior art absorption detector, shown in FIG. 2, a low wavelength ultraviolet light 20, typically between 200 nanometers and 280 nanometers, is incident upon a diffraction grating 21. Grating 21 separates the light into different wavelength components and one of these components 24 is passed through the sample measurement region 23 of capillary tube 22. The light 25 emerging from the sample is incident upon a first photodiode 26. Actually, as shown in FIG. 2, the light from grating 24 is divided into two parts, one which passes through the sample and a second which is incident upon a second photodiode 27. The signal from photodiode 27 is used as a reference so that as the relative intensity from light source 20 changes, the signal from first photodiode 26 is corrected for the changes in light source 20.

This apparatus has two primary limitations. First, only one wavelength at a time is incident upon the sample. To use a second wavelength, grating 21 must be mechanically repositioned so that a different wavelength is incident upon capillary tube 22. The second problem with this absorption detector is designing a holder for capillary tube 22 so that capillary tube 22 is not damaged while performing the measurement, changing samples, or loading the sample into the capillary tube.

In prior art fluorescence detectors, an ultraviolet (UV) light source, having a selected wavelength, illuminates the sample. The wavelength of the ultraviolet light causes certain molecules to fluoresce and emit light at wavelengths different from the wavelength of the incident UV light. A spectrophotometer is oriented at an angle, typically 90°, from the light source so that the emitted visible light (between 450 and 630 nm) is measured against a black background.

Fluorescence detection is inherently very sensitive and biomolecules can be detected using fluorescence via a fluorescence tag for proteins or a "stain" for DNA. The spectrophotometer, used in fluorescence detectors, typically has a grating and a photomultiplier tube. The grating reflects a specific wavelength of the fluorescent light from the sample upon a photomultiplier tube. The photomultiplier tube provides great sensitivity, but using such a tube inherently restricts the detector to a single channel. Rotation of the grating is required for the selection of a different wavelength.

To overcome the limitations of single wavelength operation, a detector has been developed which utilizes a spectrophotometer and a diode array. In this detector, the light from the sample is incident upon a grating. The grating disperses the light from the sample into a spectrum of wavelengths. Instead of having a single photodiode or photomultiplier tube to intercept the light from the grating, an array of up to 1000 photodiodes on a single semiconductor chip is used.

In this self scanning diode array detector, electronic sensing circuitry measures the charge on a capacitor associated with each diode by quickly scanning the capacitors with a video type signal. Thus, the relative light intensity incident upon each diode is measured. Each diode in the array corresponds to two nanometers in bandwidth and so the measurement provides a complete spectrum. However, the rapid switching from one diode to another introduces electronic noise, which in turn limits the sensitivity of the detector. Thus, this detector generates a spectrum from which information about the chemistry of the sample can be ascertained by looking at the relative absorption at different wavelengths, but the detector does not provide the sensitivity of single channel detectors.

The prior art detectors are not easily adapted for use in capillary electrophoresis. Each detector requires a special holder for the capillary tube and the combination of the thin capillary tube and the requirement for changing electrolytes and samples makes an automated apparatus impractical. While as previously described, capillary electrophoresis has significant advantages over gel electrophoresis, the detector limitations inhibit the development of an automated instrument.

A detector which provides the sensitivity of the single channel absorption detector or fluorescence detector and the advantages of a multichannel detector is currently not available. Further, separate detectors are used for fluorescence and absorption measurements. Thus multiple tests are required to obtain fluorescence and absorption data. A system having an integral absorption and fluorescence detector with multiple channel capability would significantly enhance the flexibility and utilization of capillary electrophoresis and in fact all HPLC.

While capillary electrophoresis is faster and more accurate than gel electrophoresis, prior art systems still require multiple manual manipulations. For example, manual filling and replacement of the electrolyte is frequently required during electrophoresis tests. Accordingly, capillary electrophoresis measurements, while not as manually intensive as the gel electrophoresis measurements, still require some amount of manual intervention.

SUMMARY OF THE INVENTION

The capillary electrophoresis instrument of this invention includes an automated means of sampling nanoliter samples from a sample tray, an automated means for replacing the running electrolyte and the detector electrolyte used in capillary electrophoresis, an automated means for performing capillary electrophoresis tests and a single detector for simultaneously measuring both absorbance and fluorescence.

The capillary electrophoresis instrument of this invention includes a capillary tube; a programmable high voltage power supply with a first and second electrode; a vacuum tight detector electrolyte bottle containing a electrolyte, a first of the high voltage electrodes and a first end of the capillary tube; up to four running electrolyte bottles; and a sample tray. An autosampler head provides a means for moving a second high voltage electrode and the second end of the capillary tube between the four running electrolyte bottles and the sample tray. A replenishment system containing a pump, valve system, a waste bottle and electrolyte supply bottles is connected to the detector electrolyte bottle and is coupled to the running electrolyte bottles by the autosampler head so that the electrolytes in the detector electrolyte bottle and the running electrolyte bottles can be evacuated and refilled.

A system controller in the capillary electrophoresis instrument, which receives specified commands from either a personal computer or a teletype, controls the autosampler head, the high voltage supply, the replenishment system and the electrophoresis test sequence. The system controller also controls the detector and the associated electronics.

The detector contains a pulsed light source; a continuous light source; a polychromator containing a grating; and a photodiode array. The capillary tube is positioned at the entrance slit of the polychromator such that light emerging from a sample in the capillary tube is incident upon the grating. Light from the continuous light source, used for absorption measurements, is focused on a section of the capillary tube so that the light passes through the capillary tube and enters the polychromator. Light from the pulsed light source, used for fluorescent measurements, is focused on the same section of the capillary tube at a selected angle from the slit of the polychromator such that light from the pulsed light source does not directly enter the polychromator.

The visible fluorescent light excited by the pulsed light source and the unabsorbed light of the continuous light source both enter the polychromator. The unabsorbed light from the continuous light source is primarily comprised of short wavelengths while the pulsed fluorescent light is primarily comprised of longer visible wavelengths. The grating in the polychromator separates the unabsorbed continuous light and the pulsed fluorescent light into discrete wavelengths. The diode array is oriented so that individual diodes in the array receive the discrete wavelengths provided by the grating. Further, selected diodes in the array are used to measure absorbance, i.e., the shorter wavelengths while other diodes measure fluorescence, i.e., the longer wavelengths. The continuous nature of the unabsorbed light and the pulsed nature of the fluorescent light provides a means for effectively eliminating contributions to the fluorescence measurements from the unabsorbed light and conversely any contributions from the fluorescent light to the absorption measurements.

To perform a capillary electrophoresis test a series of samples are entered in a microtiter tray and a running electrolyte is placed in the running electrolyte bottles. Also, the external computer is used to supply commands to the system controller which describe the locations of hardware in the capillary electrophoresis instrument, the test conditions, and the sequence of tests to be performed. After the system controller initializes the capillary electrophoresis instrument, the specified tests are performed.

Specifically, the system controller first checks to see whether a directive has been supplied to purge and refill the electrolyte in any of the running electrolyte bottles or the detector electrolyte bottle. If such a command has been given, a level sensor is automatically lowered into the appropriate bottle and then the replenishment system is used to evacuate the bottle until the level sensor indicates that the bottle is dry. Upon receipt of the dry signal from the level sensor and a subsequent fill command, the system controller automatically raises the level sensor to a "full" position and proceeds to refill the electrolyte bottle with electrolyte from the running electrolyte storage bottle. When the electrolyte reaches the level of the sensor, the sensor sends a command to the system controller indicating that the bottle is full and the system controller then stops the filling of the bottle and raises the level sensor to a location where it does not impede the capillary electrophoresis tests.

Next, the system controller automatically moves the sample end of the capillary tube and an associated high voltage electrode into the electrolyte in a selected running electrolyte bottle. The replenishment system is used to draw a vacuum on the detector electrolyte bottle so that running electrolyte from the running electrolyte bottle is drawn into and through the capillary tube. After the capillary tube is filled, the system controller moves the capillary tube and the associated high voltage electrode into a sample in a selected well in the microtiter plate. Following previously supplied instructions from the external microcomputer or teletype, the system controller draws the sample into the capillary tube using either a vacuum or a high voltage.

After drawing the sample into the end of the capillary tube, the system controller automatically returns the sample end of the capillary tube to the electrolyte bottle and applies a high voltage so as to maintain either a constant selected voltage or a selected current across the capillary. The controller can also change either the voltage or the current with time. The high voltage causes the sample to separate and move through the capillary tube in bands. The bands pass through the fluorescence and absorbance detector which is mounted close to the second end of the capillary tube. As the sample molecules pass through the detector, light from the ultraviolet light source causes the molecules to fluoresce and this fluorescence is passed into the polychromator which disperses it onto a first subset of diodes in a photodiode array. Similarly, some of the short wavelength light from the continuous light source is absorbed by the sample as the sample passes through the detector. The polychromator disperses the unabsorbed light from the continuous light source onto a second subset of diodes in the photodiode array. The analog output signals from both subsets of diodes are processed, digitized, corrected for changes in the output intensity of the light sources and provided to the output terminal of the electrophoresis instrument.

Hence, the instrument of this invention provides a completely automated means for performing capillary electrophoresis and an unique detector which includes both fluorescence and absorption capability in conjunction with multichannel capability. The multichannel fluorescence and absorption detector approaches the sensitivity of the prior art single channel detectors by reducing the electronic noise limitations of the prior art self scanning diode array detectors by using a discrete amplifier for each diode. The detector sensitivity is further enhanced by the use of broader bandpass detection, i.e., 16 nm per diode instead of 2 nm as in the prior art detector.

Figure 5A:
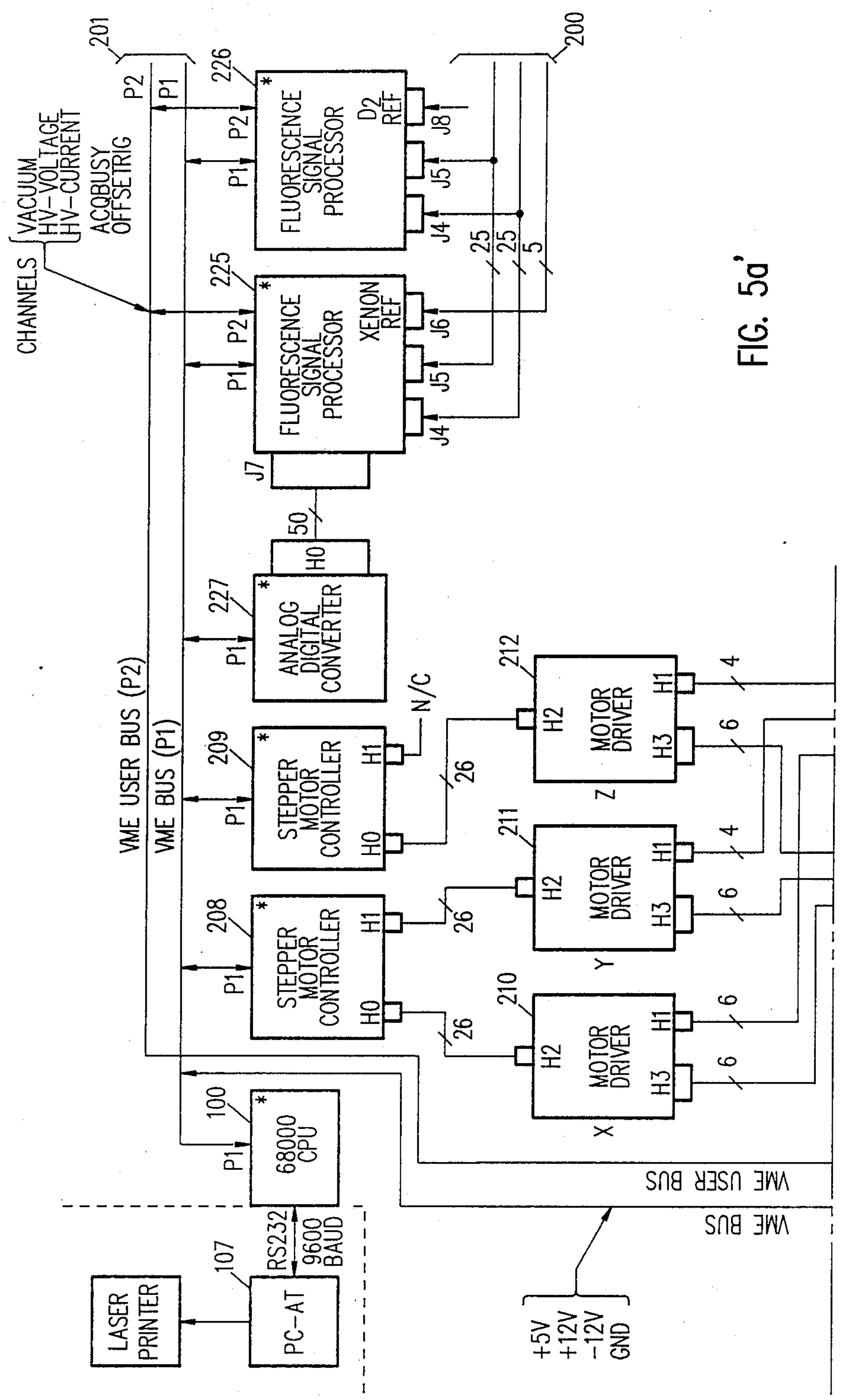
Figure 5A:
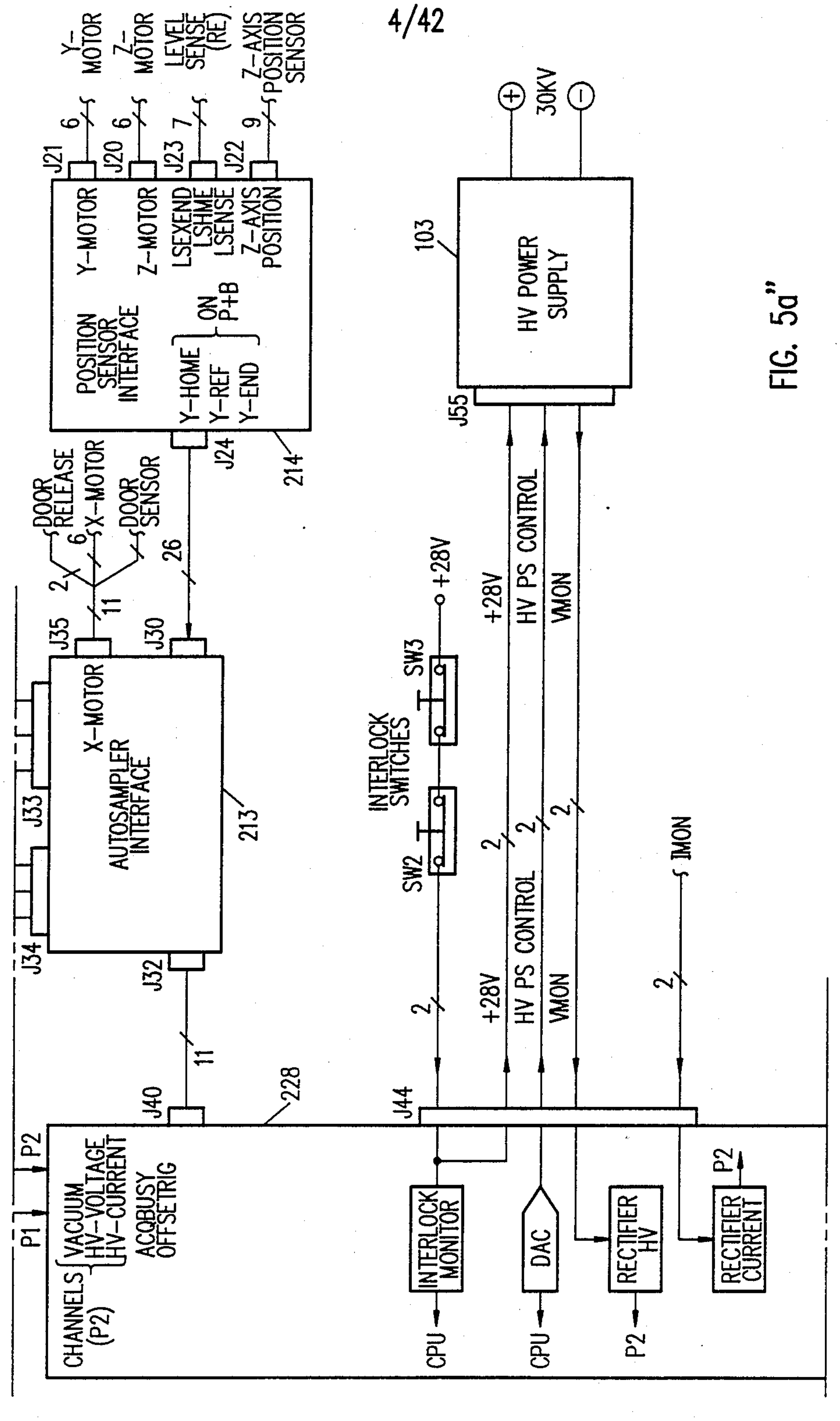
Figure 5A:
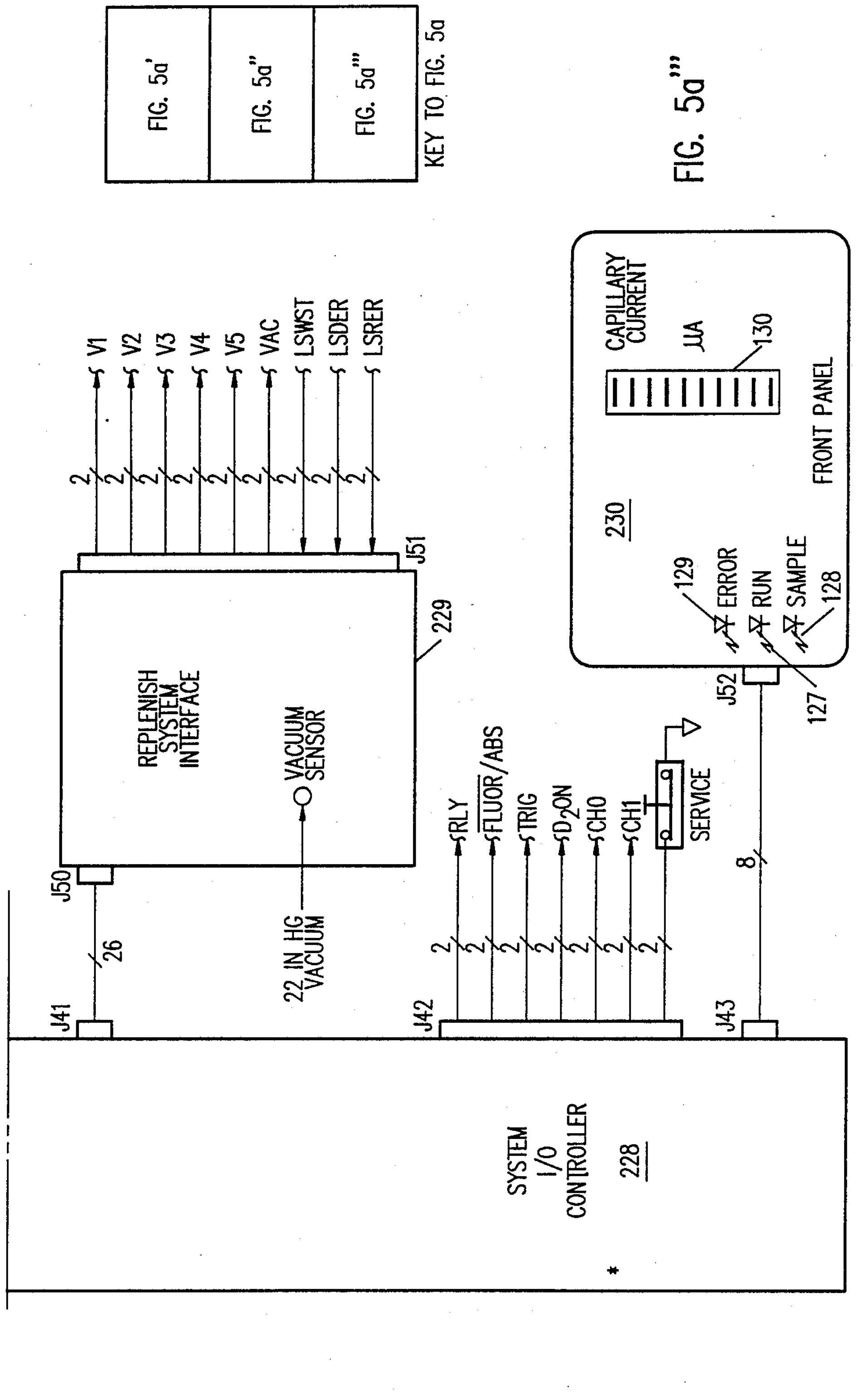

FIGS. 5a'–5a''' and 5b'–5b'' are a detailed block diagram of the capillary electrophoresis instrument of this invention.

Figure 6A:
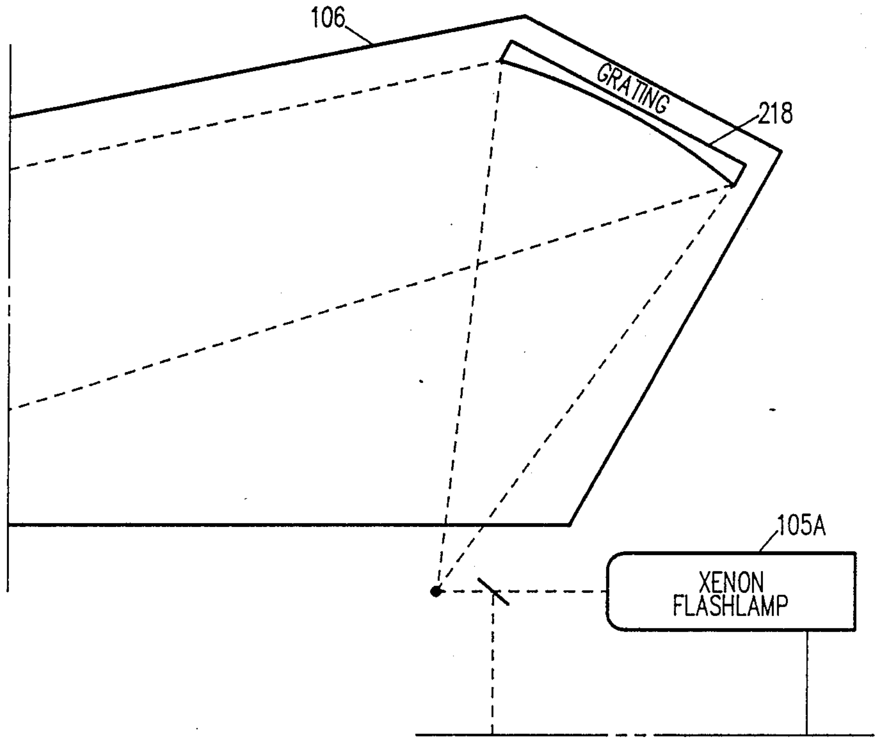
Figure 6C:
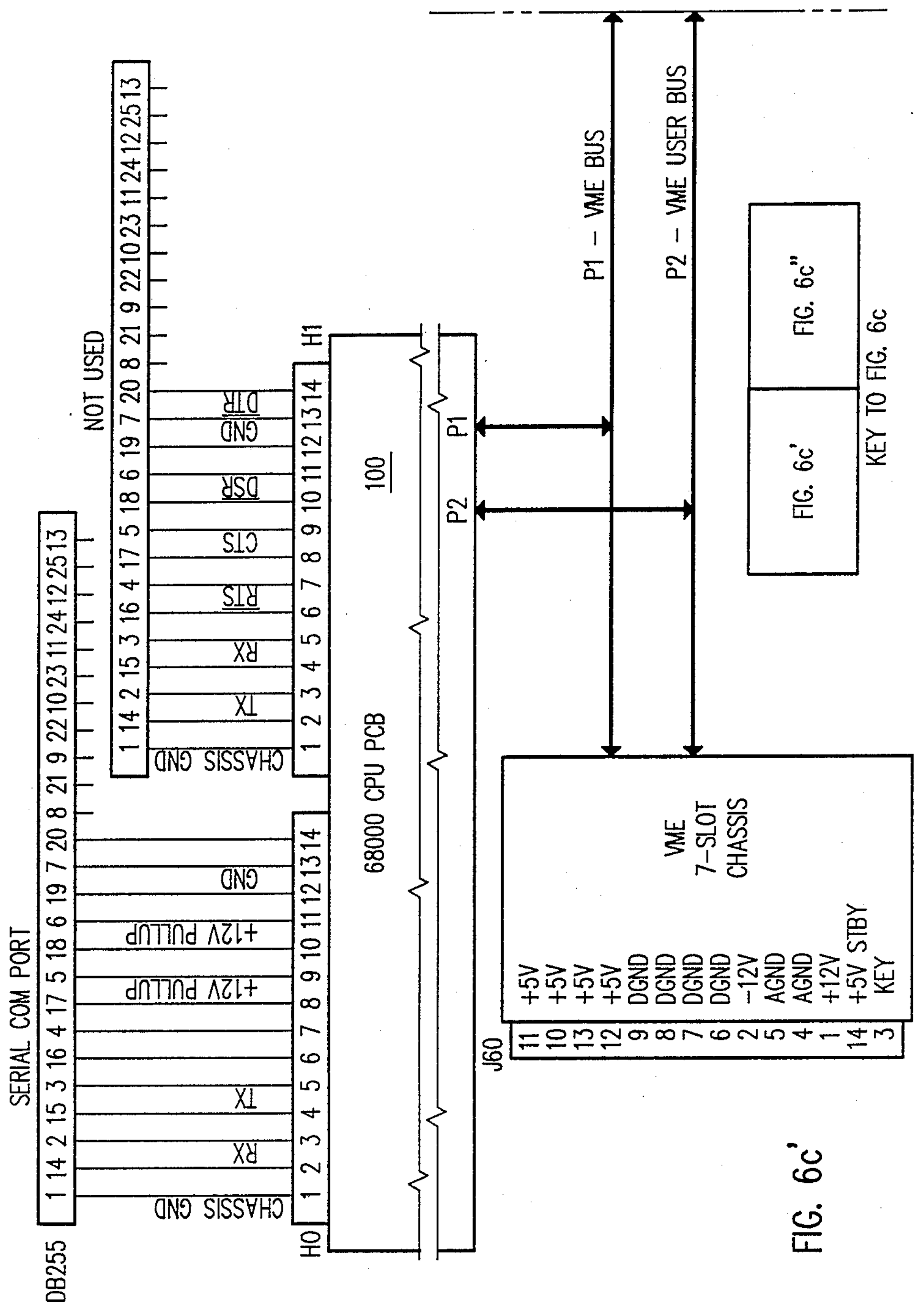
Figure 6D:
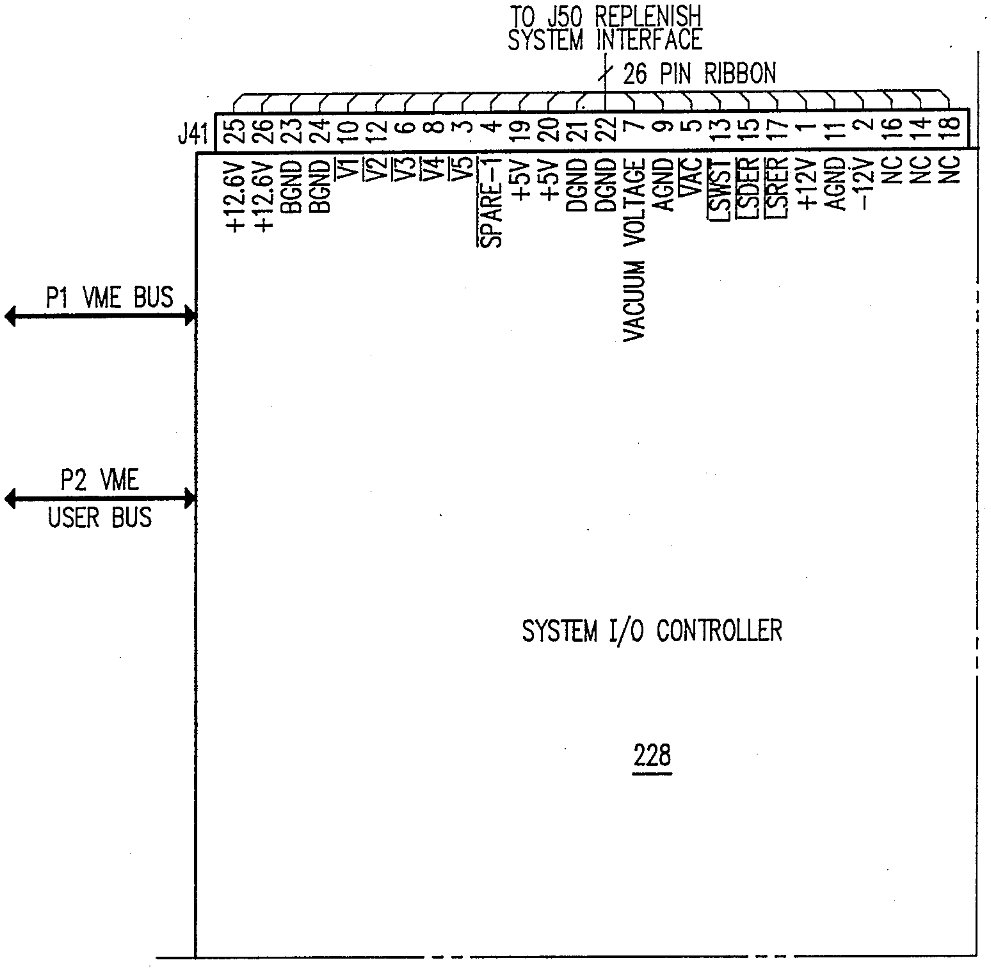
Figure 6D:
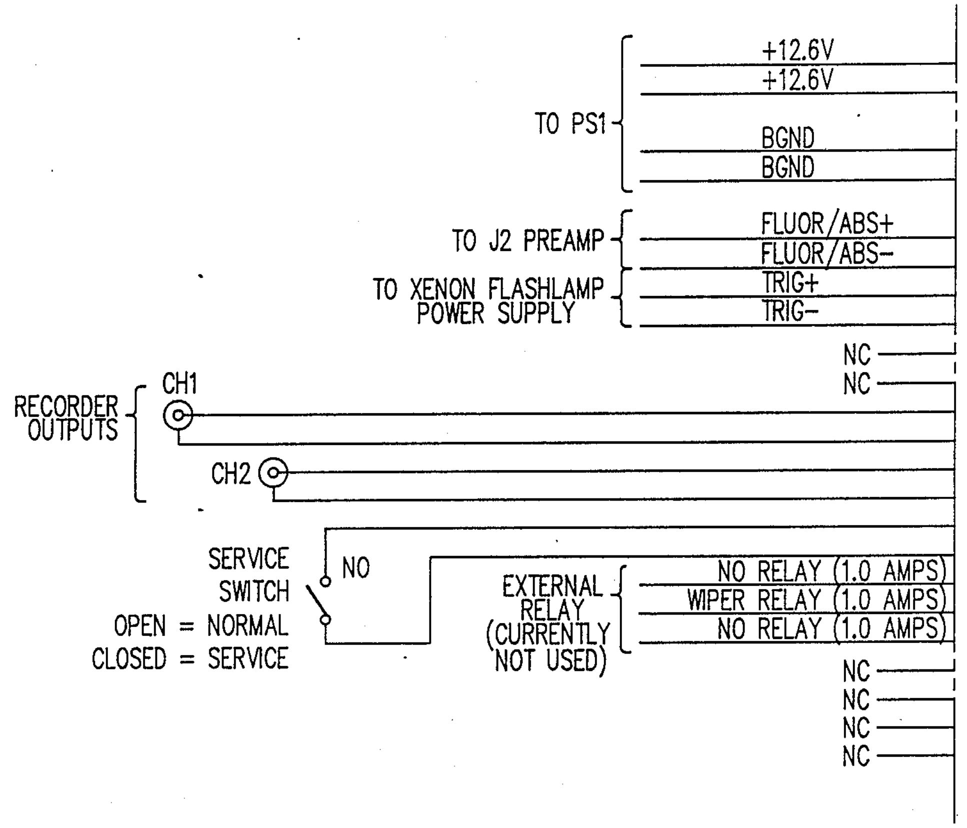
Figure 6E:
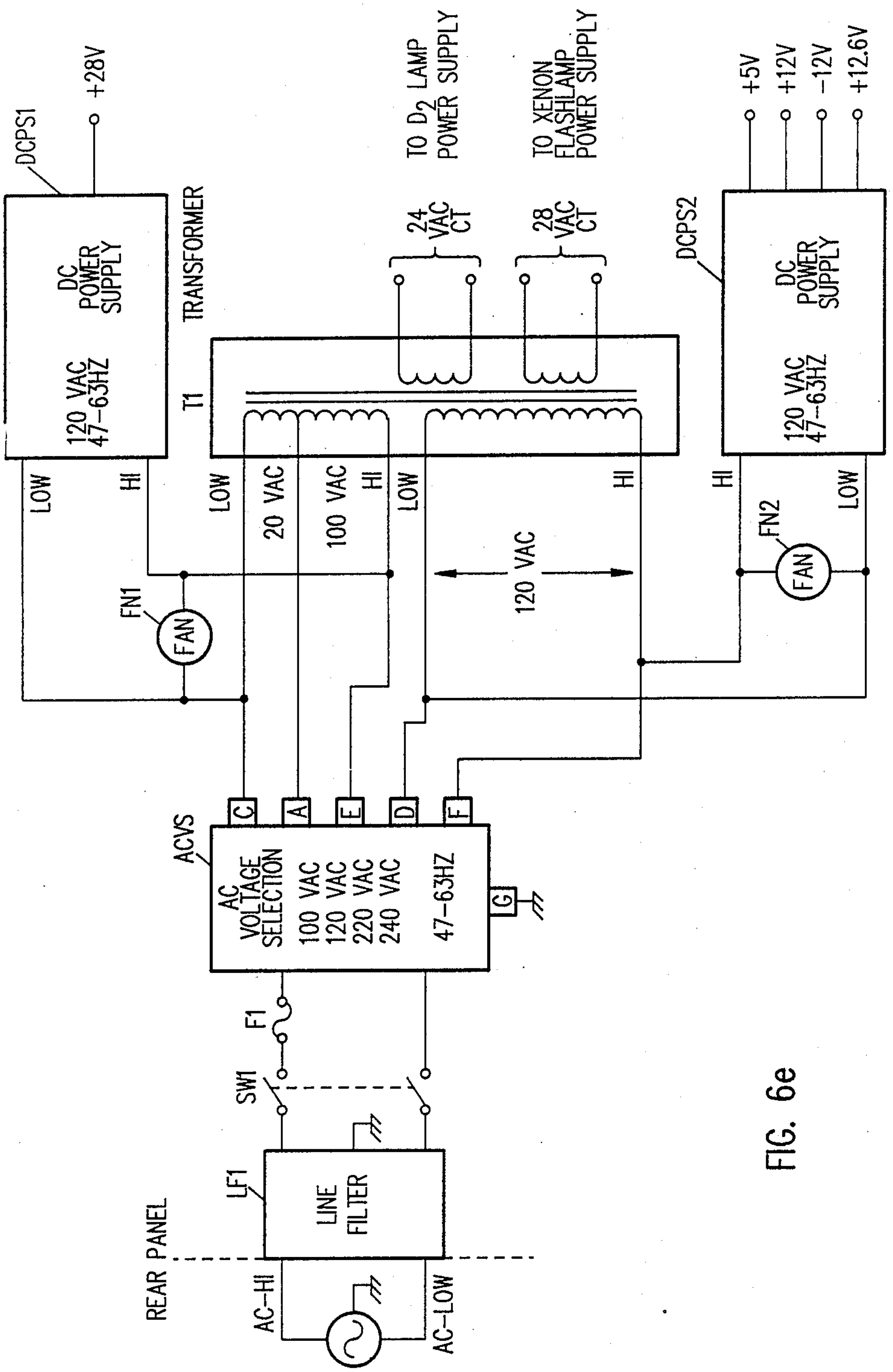

FIGS. 6a 6a'–6a''''', 6b'–6b'', 6c'–6c'', 6d'–6d''''' and 6e are wiring diagrams for the capillary electrophoresis instrument of this invention.

Figure 7:
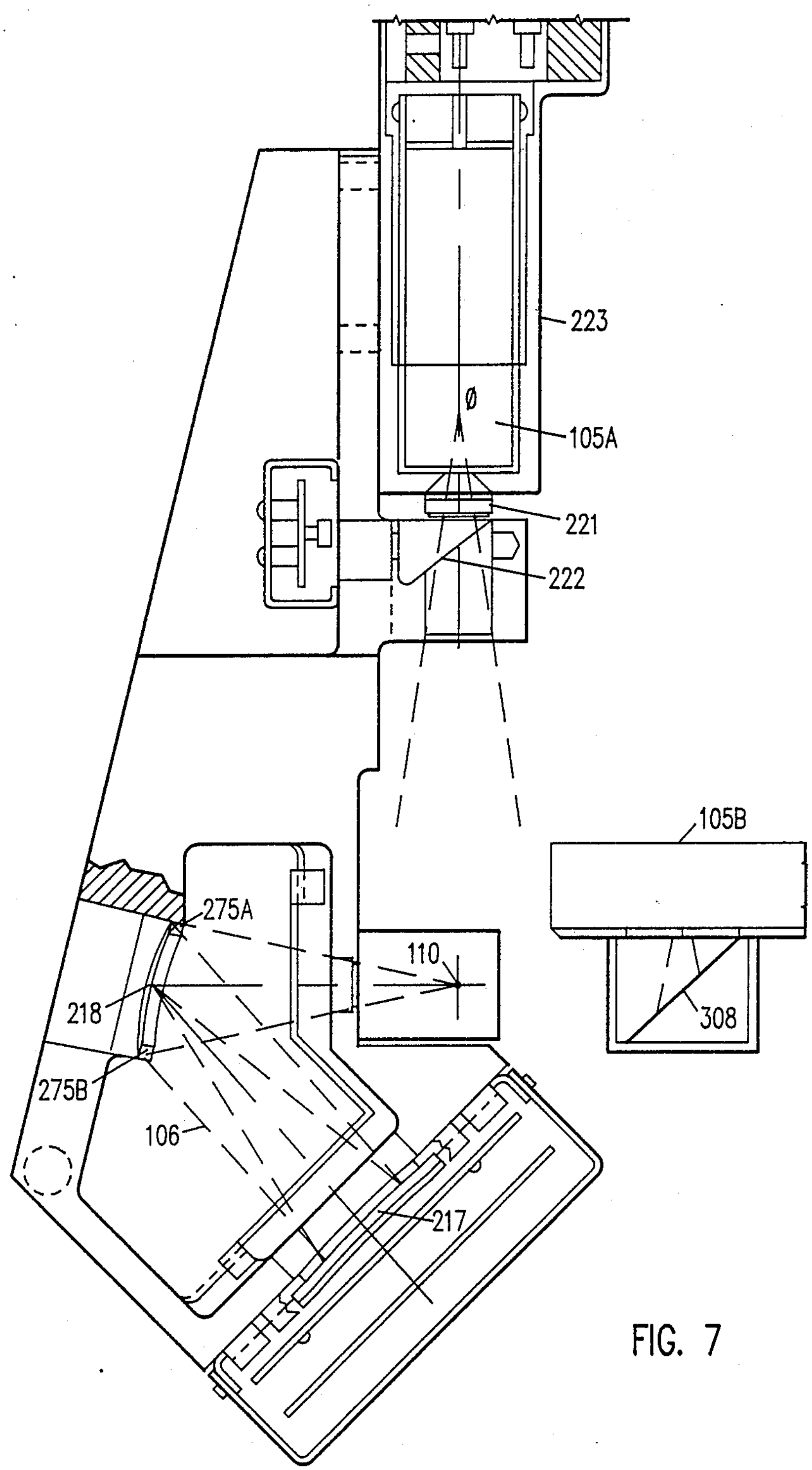

FIG. 7 illustrates detector module 104 of this invention.

FIGS. 8a through 8g are a front view, a top view, a section A—A view, a section B—B view, a left side view, a right side view, and a bottom view, respectively, of capillary tube holder 232.

Figure 9:
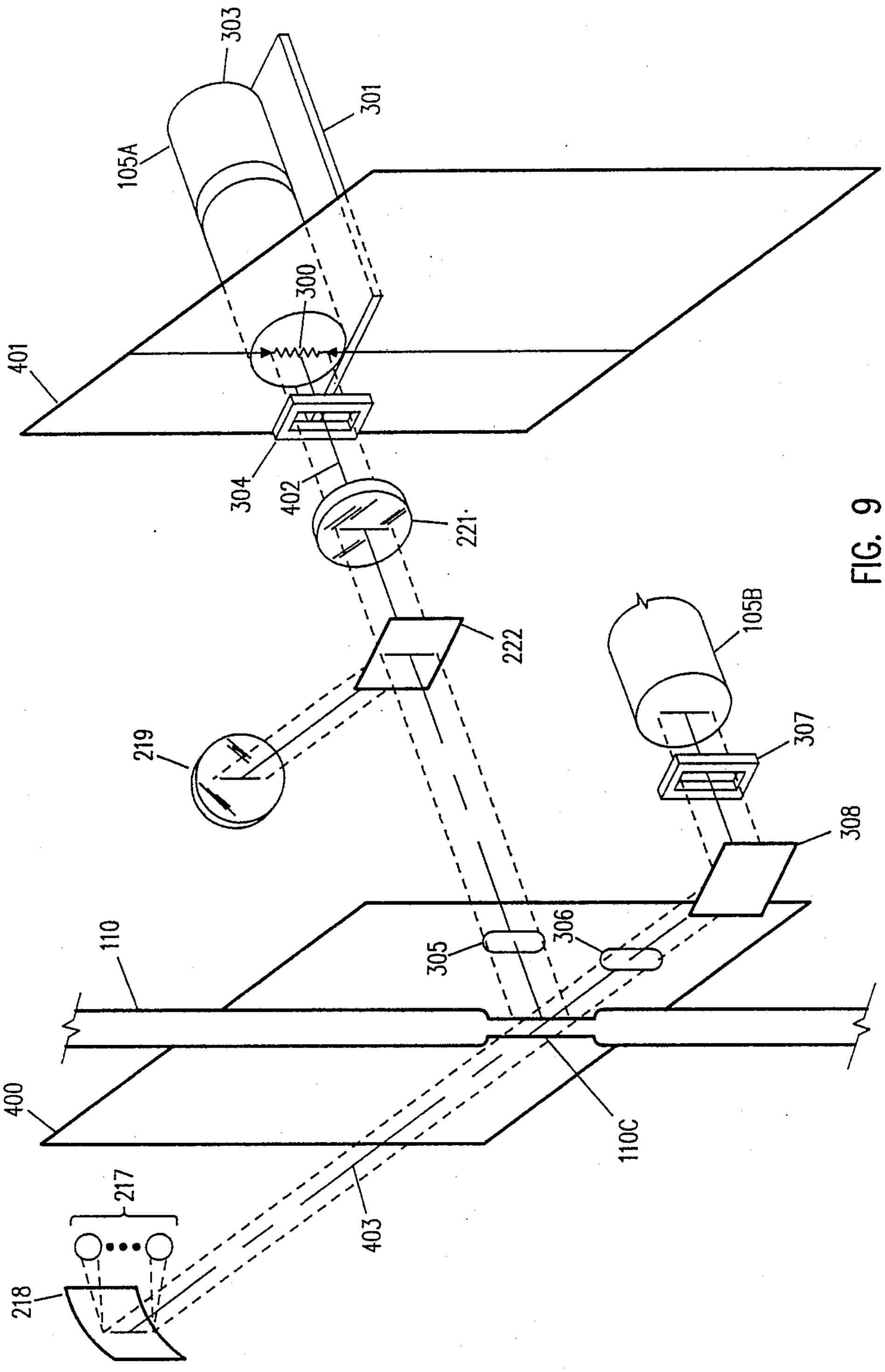

FIG. 9 illustrates the general spatial relationship of the components in the detector of this invention. The figure is not drawn to scale.

Figure 10:
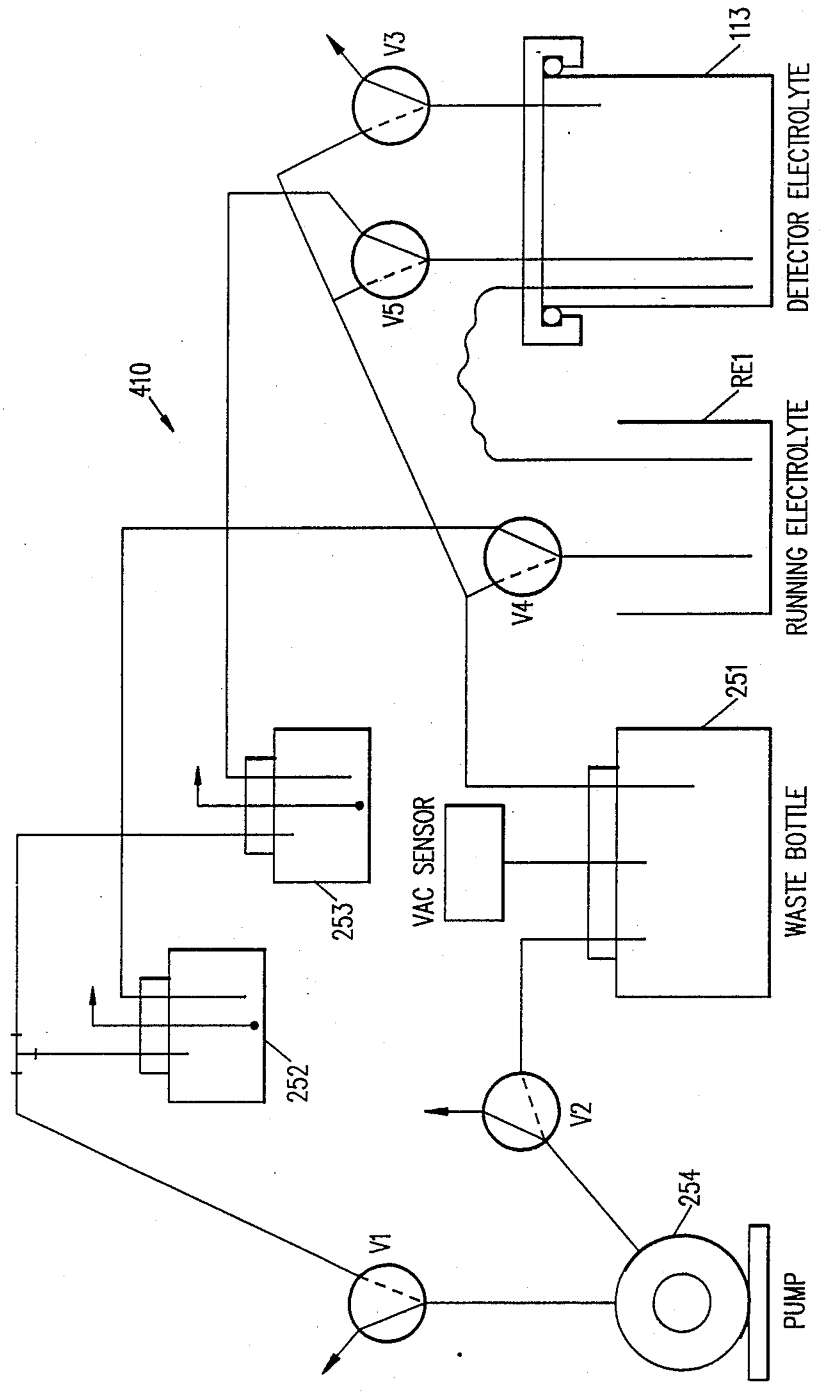

FIG. 10 is a simplified schematic representation of the replenishment system of this invention.

Figure 11A:
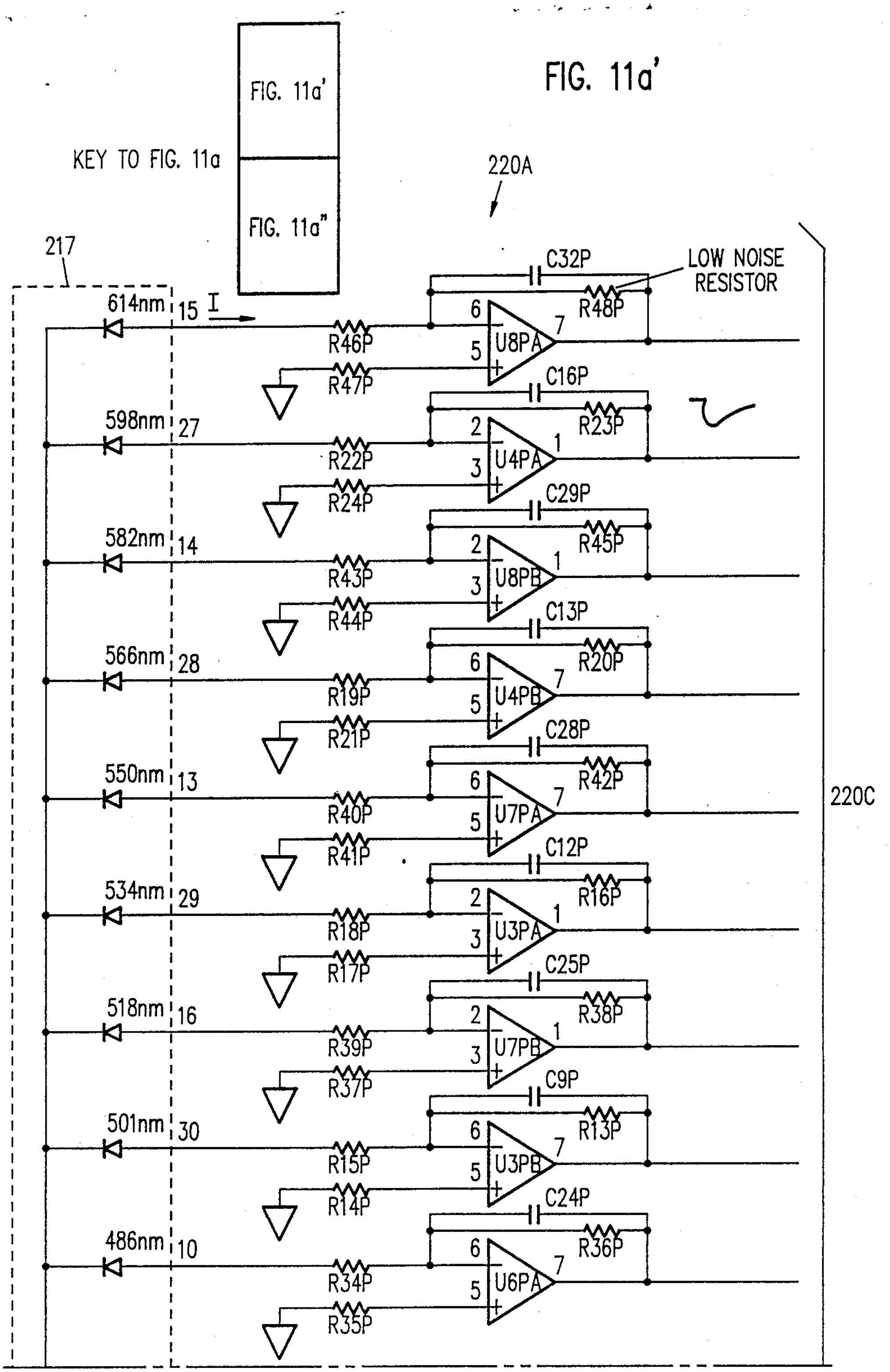
Figure 11B:
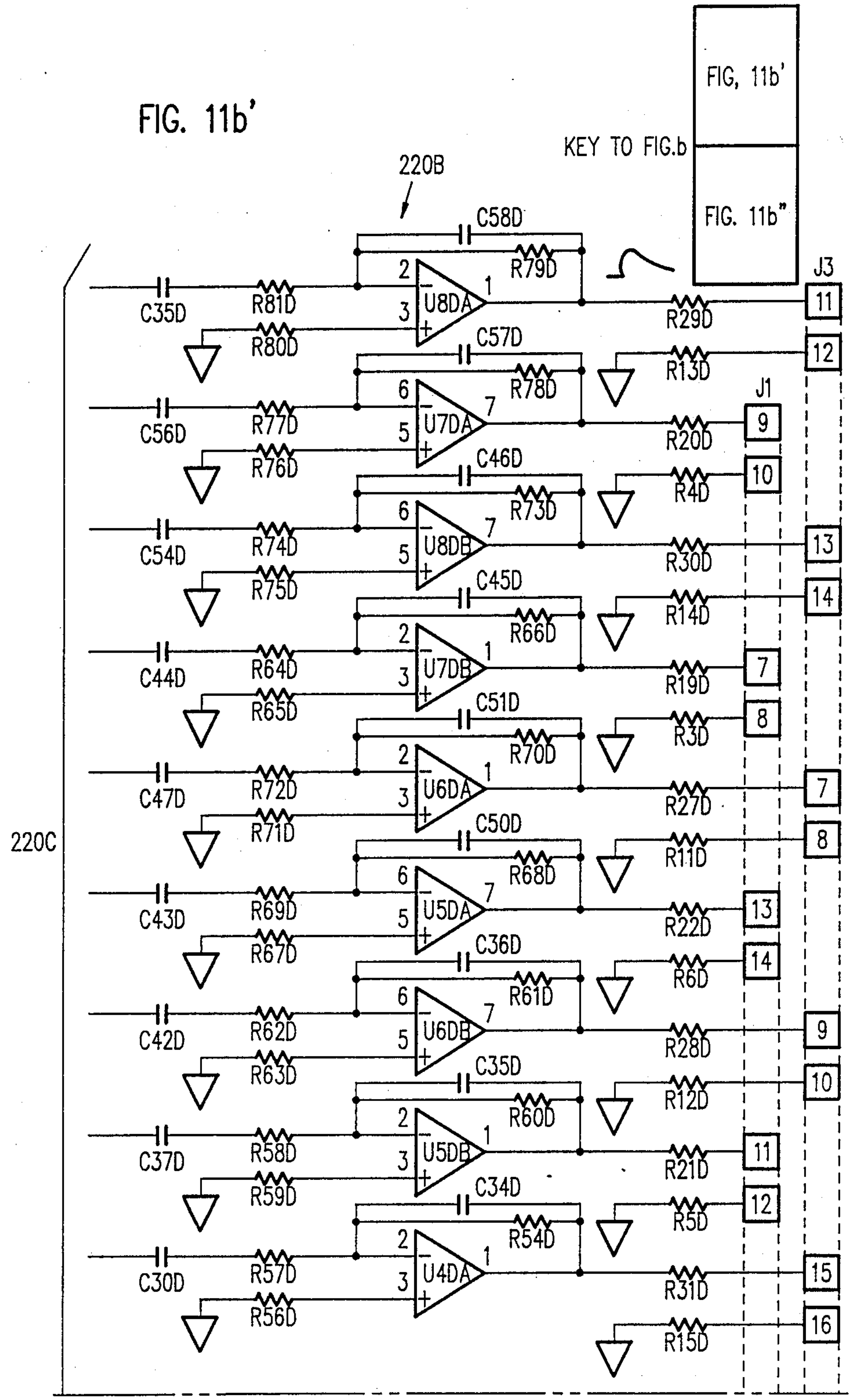

FIGS. 11a'–11a'' and 11b' are a schematic of detector preamp circuit 220 of this invention.

Figure 12A:
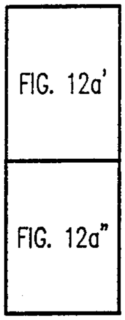
Figure 12A:
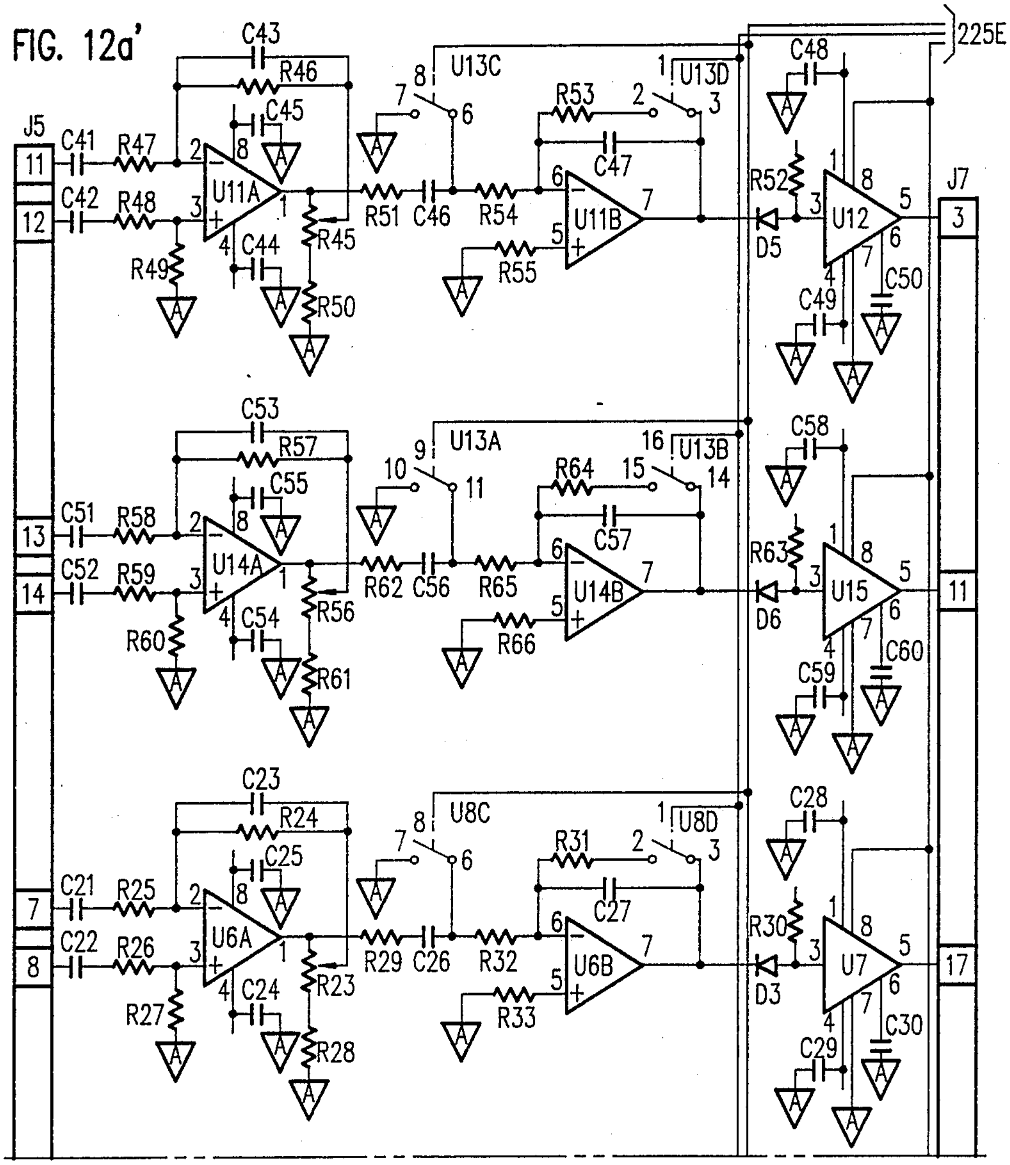
Figure 12C:
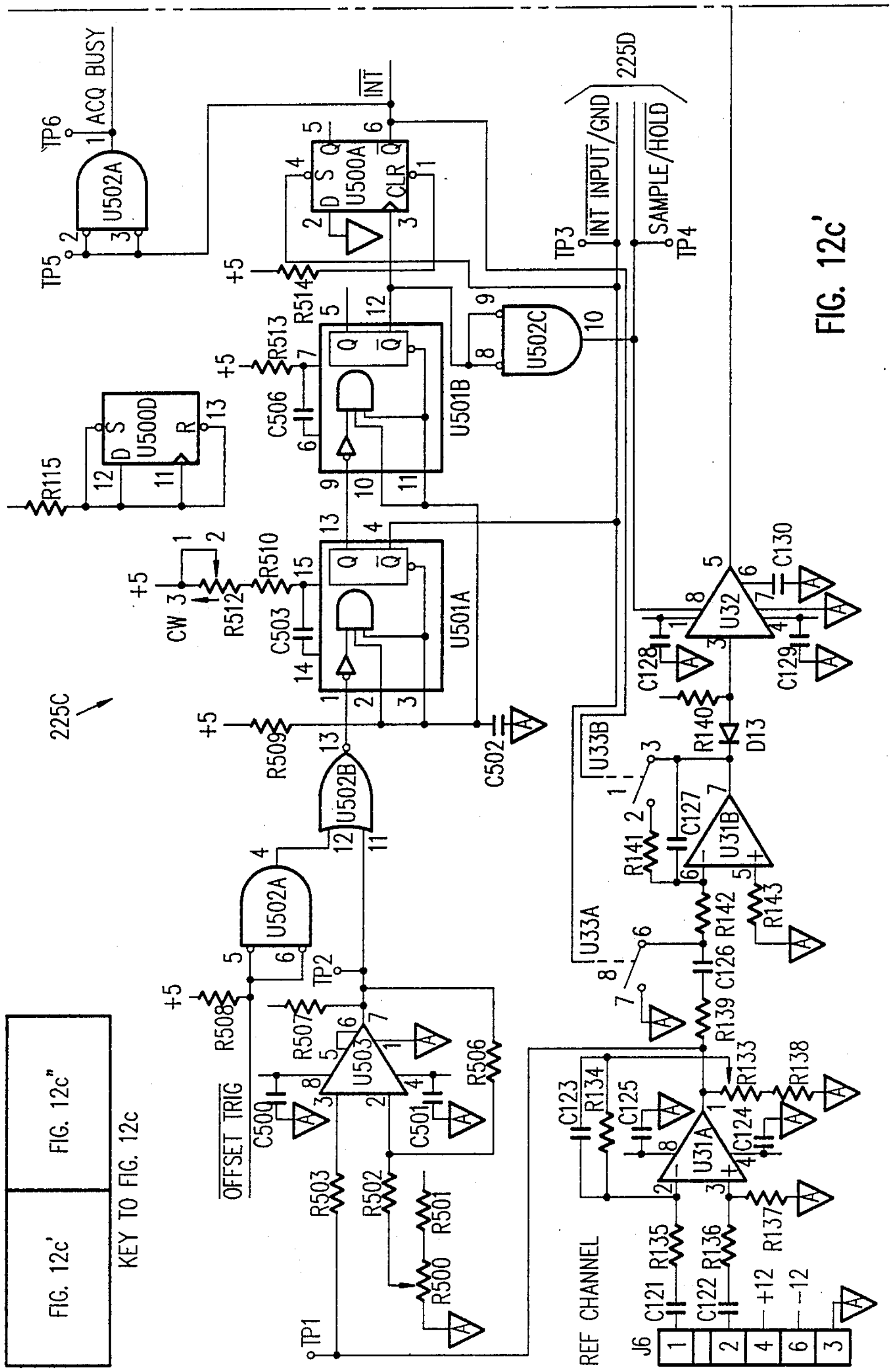
Figure 12D:
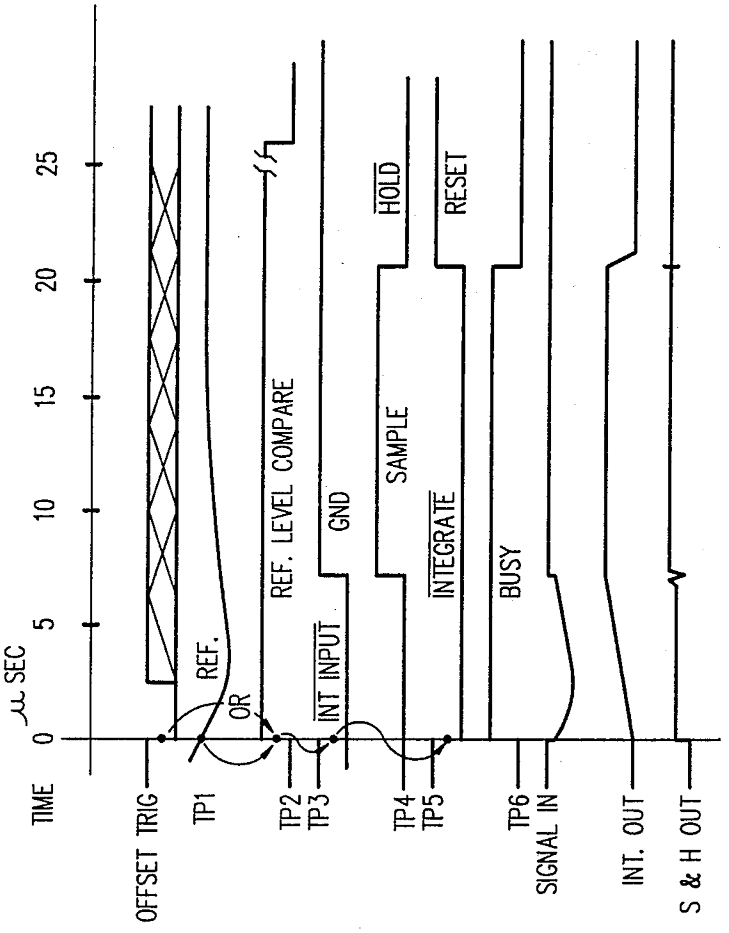

FIGS. 12a'–12a'', 12b'–12b'' and 12d are a schematic of the fluorescence signal processing circuit 225 of this invention and a timing diagram representative of each channel in circuit 225.

Figure 13A:
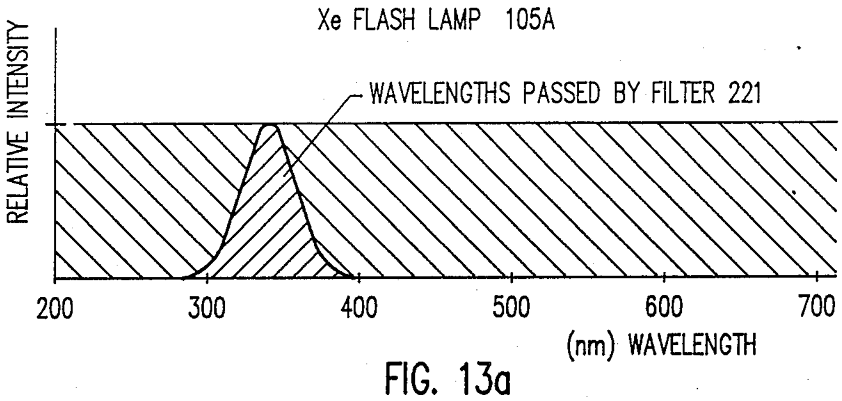
Figure 13B:
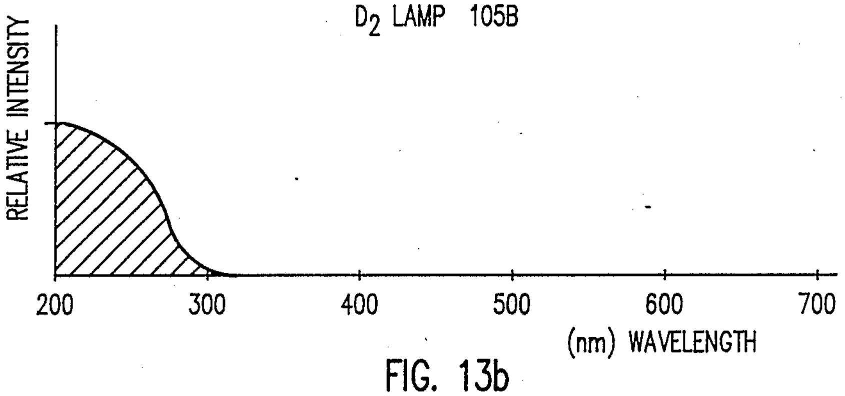
Figure 13C:
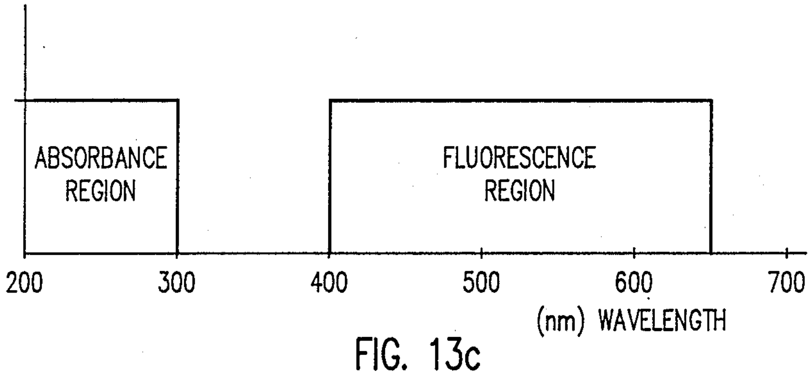

FIGS. 13a through 13c illustrate the wavelength of the light sources of this invention and the range of absorbance and fluorescence wavelengths.

Figure 14A:
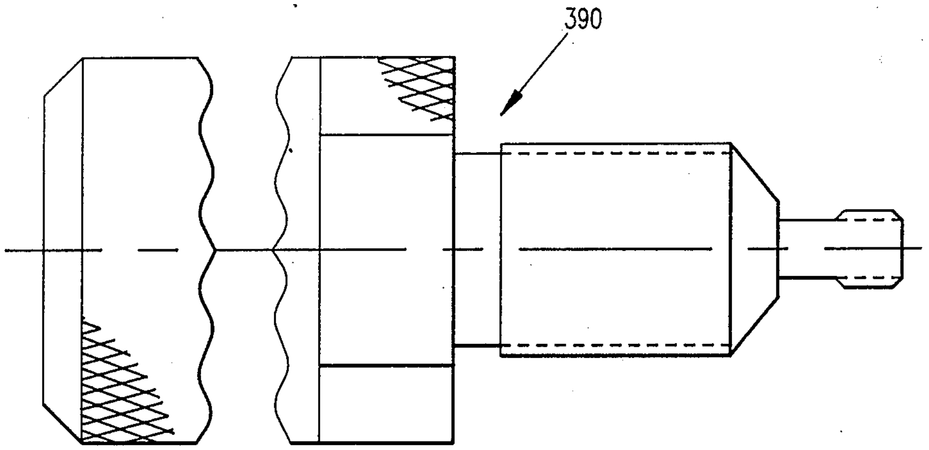
Figure 14B:
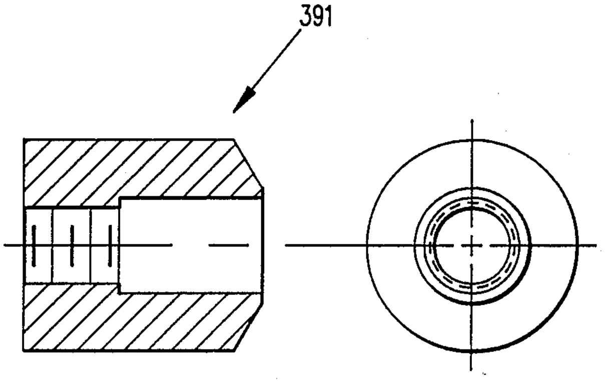

FIGS. 14a and 14b illustrate the screw and clamp respectively used to secure capillary tube 110 in capillary tube holder 232 of this invention.

DETAILED DESCRIPTION

Figure 1:
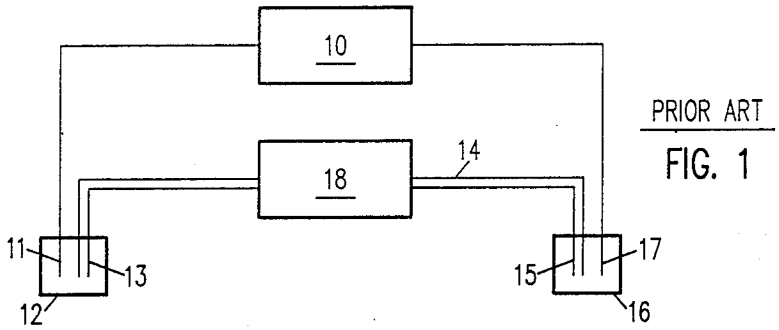
FIG. 1 is a schematic diagram of a prior art capillary electrophoresis apparatus.
Figure 2:
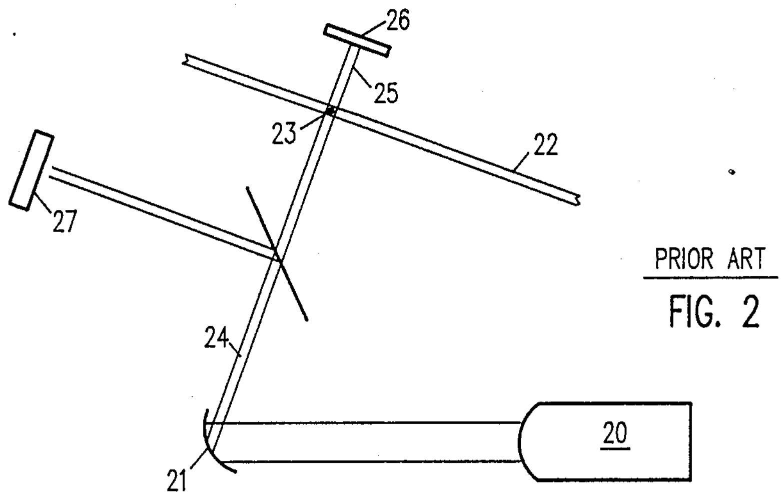
FIG. 2 illustrates a prior art single channel absorption detector for use in capillary electrophoresis.
Figure 3:
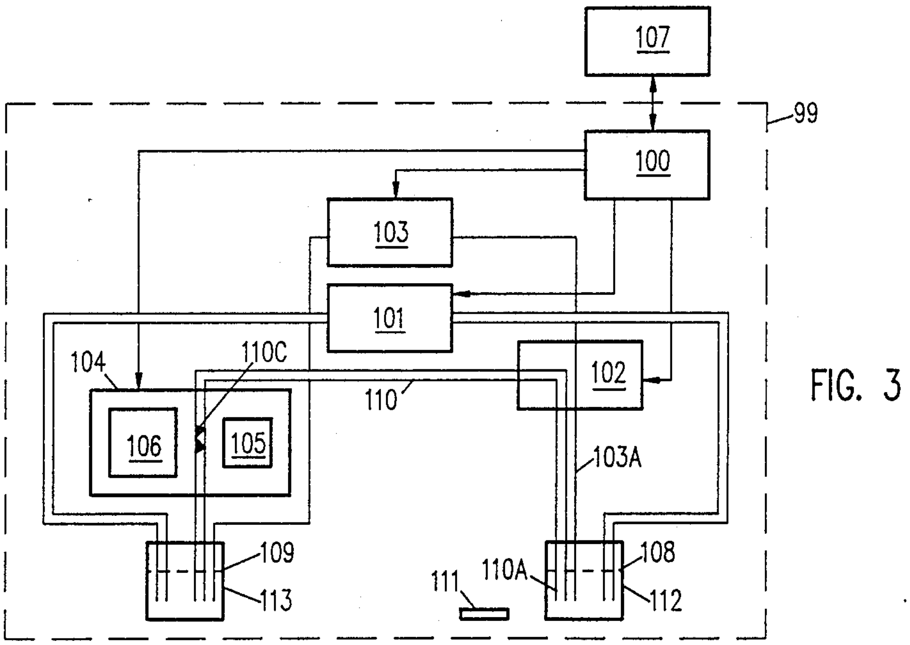
FIG. 3 illustrates a general block diagram of the capillary electrophoresis instrument of this invention.

The capillary electrophoresis instrument of this invention includes a detection system which simultaneously measures absorption and fluorescence induced by light from a light source, a replenishment system for automatically replacing the running electrolyte and the detector electrolyte and an autosampler for automatically analyzing up to 96 different samples. A block diagram of the electrophoresis instrument of this invention is shown in FIG. 3. A system controller 100, a VME 3U style 10 Mhz 68000 microprocessor VME bus master in one embodiment, interfaces with a replenishment system 101, an autosampler 102, a high voltage power supply 103, and a detection system 104 including light source 105 and polychromator 106.

Either an external computer 107 or a teletype provides instructions to system controller 100. System controller 100 interprets these instructions and automatically performs capillary electrophoresis using a specified sample. The system controller 100 may also be directed to replace electrolyte 108 in running electrolyte reservoir 112 and electrolyte 109 in detector electrolyte reservoir 113 using replenishment system 101.

To perform a capillary electrophoresis test, system controller 100, following commands from external computer 107, moves capillary tube end 110A and electrode 103A to sample 111 using autosampler 102. Sample 111 is entered in capillary tube 110 using high voltage from high voltage power supply 103 or vacuum created by replenishment system 101.

After the sample is introduced into capillary tube 110, system controller 100 causes autosampler 102 to move capillary tube end 110A and associated high voltage electrode 103A into the electrolyte of running electrolyte bottle 112. A programmed high voltage from high voltage supply 103 is then applied across capillary tube 110 so that the sample is moved by electrophoresis through capillary tube 110. Simultaneously, the system controller activates detection system 104.

In one embodiment, light source 105 contains both a xenon flash tube and a deuterium lamp. The deuterium lamp generates a beam of light which passes through a first slit and lens imaging system so that the light is focused precisely on the center of capillary tube 110. A second lens imaging system with or without a slit, focuses the light from the xenon flash tube on the inner diameter of capillary tube 110. As described below, the light sources are oriented about a sample region 110C of capillary tube 110 so that fluorescence and absorption measurements can be obtained simultaneously. Here, sample region 110C means the region of capillary tube 110 where the bands of different species of sample molecules are detected and not the end 110A of capillary tube 110 where the sample is initially introduced. The capillary tube and the capillary tube holder are described more completely below. Detector 104 of this invention provides an increased capability over prior art detectors because both fluorescence and absorption measurements can be made without changing the on-column detector.

Polychromator 106 contains a grating oriented such that the light from the deuterium lamp and fluorescent light excited by light from the xenon flash lamp are simultaneously incident upon the grating. As described more completely below, the grating is selected such that the fluorescent light is projected onto a first subset of photodiodes and the deuterium light, which is not absorbed by the sample molecules in capillary tube 110, is focused upon a second subset of photodiodes in detector 104. Accordingly, detector 104 simultaneously measures both absorbed light and fluorescent light.

Output signals from the photodiodes responding to the deuterium lamp are passed to a signal processor where signals are first processed by an analog system. The output signals from the analog system are passed through an analog to digital converter and then the 12-bit digital output signals from the analog to digital converter are provided to the output lines of the electrophoresis instrument. In another embodiment, the absorbance signals from the diode array are processed directly by an analog to digital converter which generates 16-bit digital output signals.

The fluorescent photodiode output signals, which are typically about ten microseconds in duration, are amplified and captured in a sample and hold circuit and then passed through an analog to digital converter. For each flash of the xenon flash lamp, the detector output signal is divided by a flash lamp reference signal to reduce the effect of flash to flash intensity diferences. In one embodiment, the flash rate is 100 Hz, ten ratioed values are averaged to further improve the signal to noise ratio and reduce the data transfer rate to 10 Hz. This 10 Hz data is provided to the output terminals of the capillary electrophoresis instrument. The capillary electrophoresis instrument separates, for example, very large DNA molecules (chromosomes), virus particles, and cell organelles.

Figure 4:
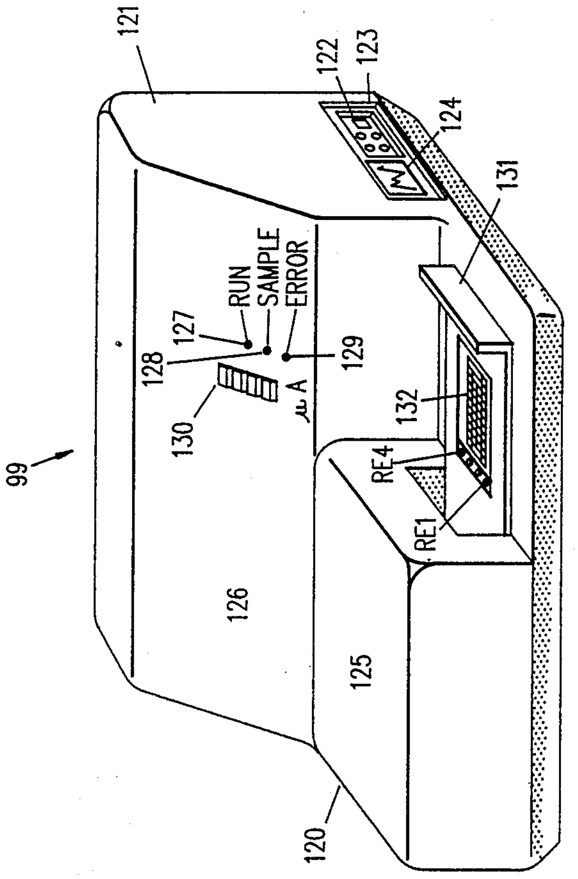
FIG. 4 illustrates the capillary electrophoresis instrument of this invention.

The capillary electrophoresis (CE) instrument 99 of this invention, as illustrated in FIG. 4, is 34 inches wide by 23 inches deep by 18 inches high at its highest point. AC power is provided through the rear panel to an AC power entry module having an integrated RFI line filter, and a fuse. A UL recognized, CSA certified, and VDE approved power entry module, such as that made by Corcom 5EFM4S, is used in the CE instrument. In viewing the instrument from the front, the left side 120 of instrument 99 has a fan outlet. The right side 121 of instrument 99 contains a fan inlet 124 and RS232 serial communication port 122, which is used to link an IBM PC-AT compatible computer or a teletype to CE instrument 99, and two strip chart recorder output channels with BNC output connectors 123.

The front of instrument 99 has two removable covers. A first front cover 125 encloses autosampler 102 mechanism, electrolyte replenishment system bottles, polychromator 106 and a high voltage power supply 103. All of these components may need frequent access by the operator. This cover when opened activates an interlock which turns off the HV power supply 103 and informs system controller 100 (FIG. 3), a central processing unit (CPU), of CE instrument 99 that the interlock was triggered. The second front cover 126 encloses the electronic circuits, DC power supplies, transformer and other components.

On the front of the CE instrument are three light emitting diodes (LED) 127, 128, 129 and a capillary current monitor 130. The LEDs indicate the RUN, SAMPLE, or ERROR conditions of CE instrument 99. When the ERROR LED 129 is lit, one of the following errors have occurred:

1. A safety interlock has been triggered;
2. A high level current limit has been exceeded and Joule heating of the electrolyte may result;
3. A low level current limit has been exceeded and air bubbles may be present within the capillary tube; or
4. The communication between the PC-AT and the CE instrument has been lost.

SAMPLE LED 128 indicates that an autosampler head, described below, is moving the capillary tube input end 110A to either a microtiter well or a running electrolyte (RE) bottle, also described below. High voltage is not applied while SAMPLE is lit. RUN LED 127 indicates that the CE instrument is taking data, high voltage is applied to the capillary tube ends, and a sample is being quantified by the electronics of CE instrument 99.

The autosampler access door is part of a carriage 131 and opens to the right side of the instrument. (See FIG. 4). Autosampler carrier 131 slides from the external load position to the internal operate position on a rail, and holds the four running electrolyte bottles (RE1 thru RE4) and either a 96 well microtiter plate 132 or a tray for eight discrete bottles (not shown). After loading the microtiter plate 132 and running electrolyte bottles RE1 through RE4 on carrier 131, carrier 131 is pushed to the left into instrument 99, against a light spring force, until the door closes and the latch is engaged. After the batch of samples has been processed by CE instrument 99, the door latch is automatically released by CPU 100 and the processed sample tray slowly slides out of the instrument on carrier 131.

Access to instrument 99 via carrier 131 and its integral door is prohibited during a test since up to 30 KV is present across capillary tube 110. Carrier 131 and door are sensed as being closed by an infrared opto sensor. The carrier is released to open by a solenoid release mechanism.

Capillary electrophoresis instrument 99 is illustrated in the system block diagram of FIGS. 5*a*'–5*a*''' and 5*b*'–5*b*'' and wiring diagrams FIGS. 6*a*' through 6*e*. In one embodiment, the CE instrument 99 interacts with an IBM PC-AT clone 107 having: 1. 80286 Processor; 2. 10 MhZ Clock (no wait states); 3. 1 Mega-byte of Fast RAM; 4. One 1.2 Megabyte Floppy Disk Drive; 5. One Serial and One Parallel Port; 6. Enhance AT Keyboard; 7. 44 Megabyte Full Height Hard Disk with 28 ms access time; 8. Streaming Tape Back-up; 9. EGA Card; and 10. 14" EGA Monitor.

As described more completely below, the external computer 107 or teletype provides set-up conditions to CE instrument 99 for batch processing of samples. External computer 107 could also perform post-processing of the data acquired by CE instrument 99, generate reports results via the EGA monitor and other similar functions. The post-processing functions are dependent upon the specific use of CE instrument 99 and accordingly are not considered further.

Figure 5B:
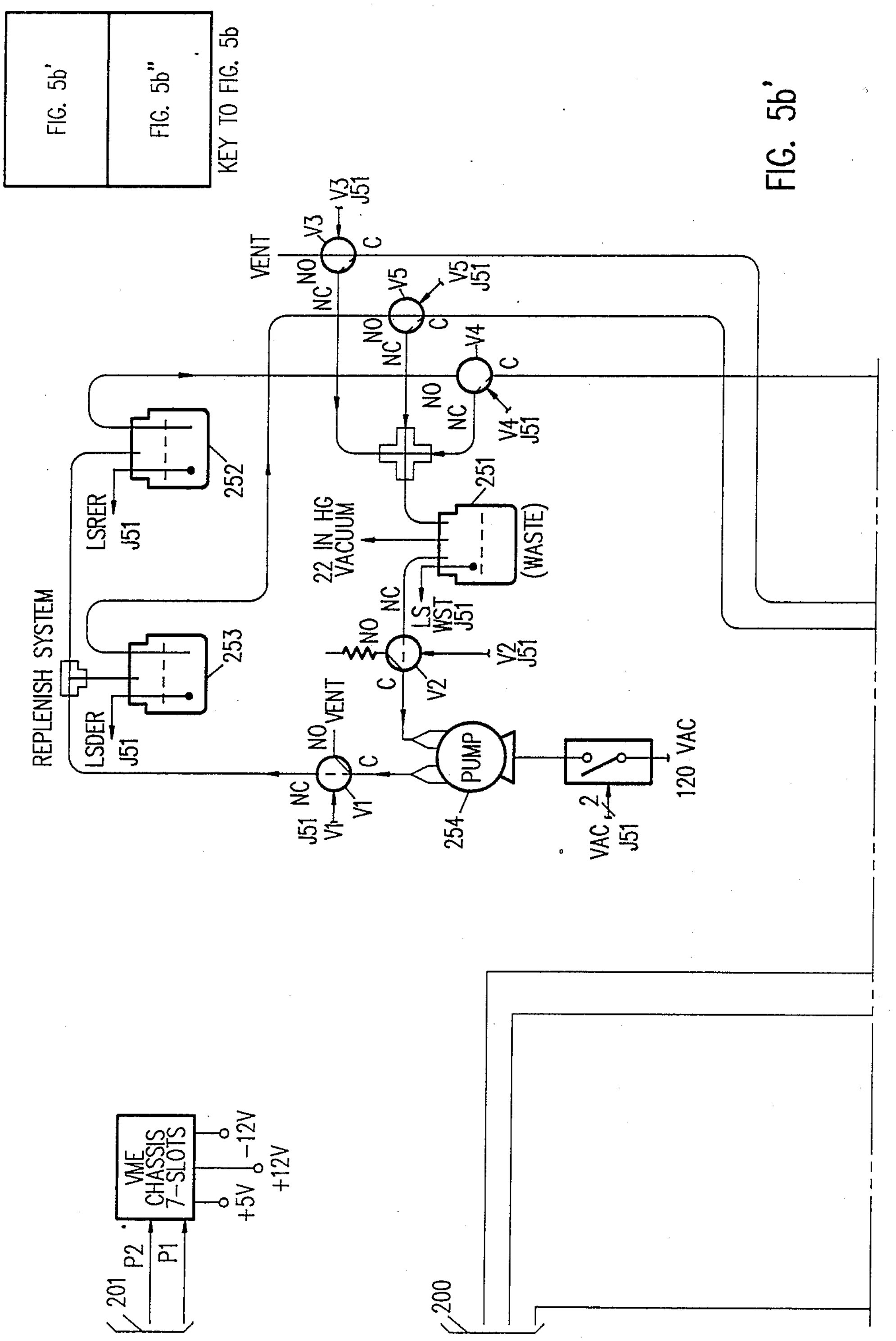
Figure 5B:
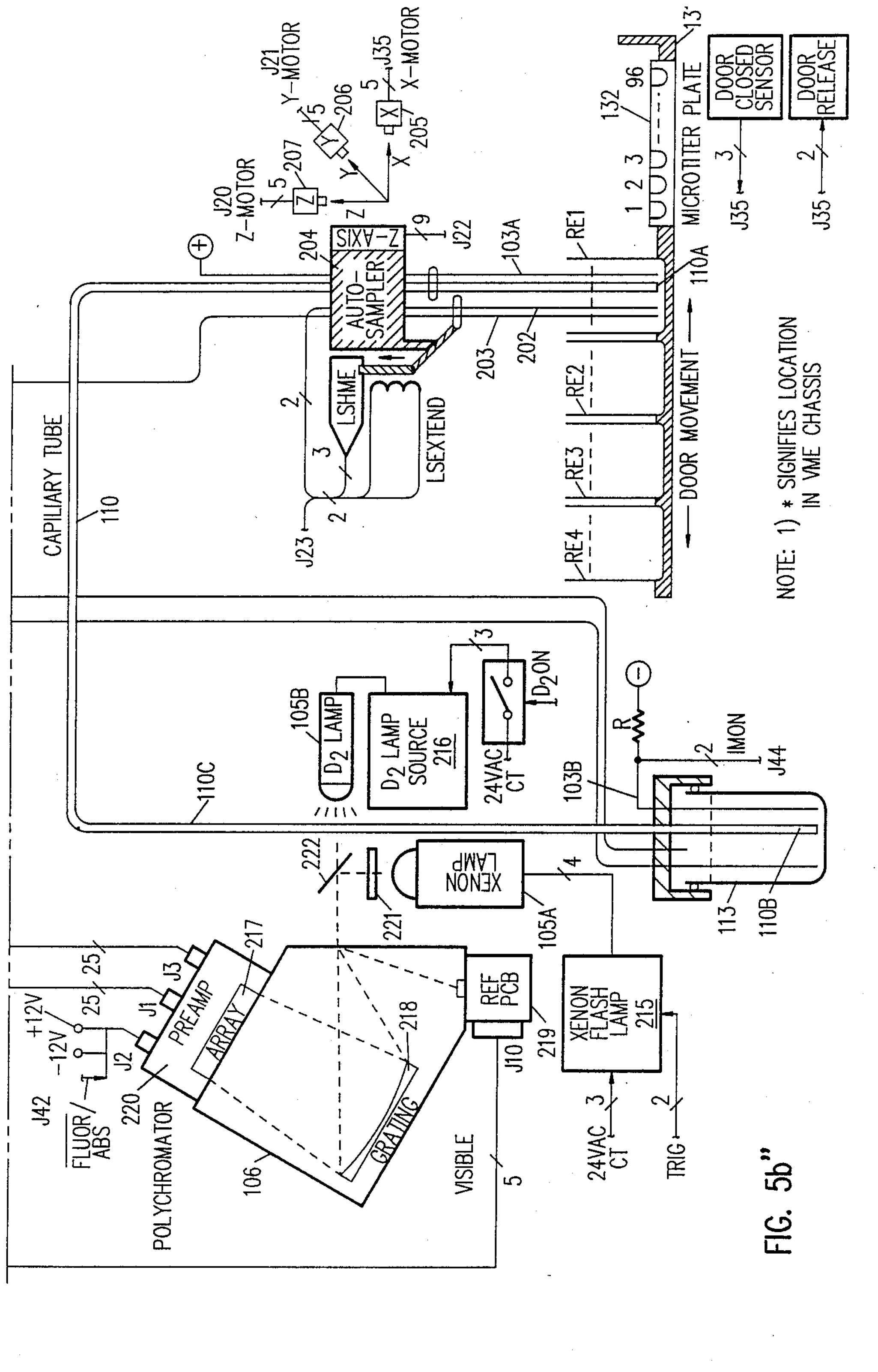

The CE instrument 99 batch processes either a single microtiter plate 132 with 96 individual sample wells or individual sample vials. The CE instrument (FIGS. 5b′-5b″) contains up to four different running electrolyte (RE) bottles RE1, RE2, RE3, RE4, and one detector electrolyte (DE) bottle 113. The automatic reagent replenishment system, described more completely below, for both the running electrolyte (RE) and for the detector electrolyte (DE) bottles may be automatically implemented after each sample run.

The autosampler has four main functions:

1. To move end 110A of capillary tube 110 (FIGS. 5b′-5b″) and associated platinum (Pt) electrode 103A between a selected microtiter well and a running electrolyte bottle RE1, RE2, RE3, RE4 and to immerse capillary tube end 110A and electrode 103A in the fluid of the selected microtiter well or running electrolyte bottle;
2. To lower a level sensor 202 sequentially into each of the four running electrolyte bottles to measure if sufficient electrolyte is present for a test;
3. To release sample tray and running electrolyte bottles to the operator via the movable sliding sample carrier 131; and
4. To deliver a reagent fill tube 203 over each of the running electrolyte bottles during a reagent replenish cycle.

The autosampler consists of an autosampler head 204 which holds an end 110A of capillary tube 110 and high voltage platinum electrode 103A, a thermistor 202 and associated tube 203 from replenishment system 101. Thermistor 202 and tube 203 are coupled to autosampler head 204 by a solenoid controlled arm. The autosampler also contains three stepper motors 205, 206, 207, stepper motor control circuits 208, 209, motor drivers 210, 211, 212, an autosampler interface 213 and a position sensor interface 214.

When carrier 131 is inserted and the door is closed, sample end 110A of capillary tube 110 with associated high voltage Pt electrode 103A are moved from the sample well to the running electrolyte bottle and vice versa by the X, Y and Z stepper motor driven head 204, sometimes called the autosakmpler head.

The X axis is defined as motion parallel to the carrier movement. Viewing the instrument from the front (FIG. 4), the X axis is from left to right. The Y axis is from the front of the instrument to the back and the Z axis is vertical.

In one embodiment, each axis has three infrared opto interrupt position sensors. The three positions are called HOME, REF and END. Viewing the CE instrument from the front, HOME position is located at the center of running electrolyte bottle, RE1. Bottle RE1 is the running electrolyte bottle closest to the front of instrument 99 (FIG. 4). For both the X and Y axis these sensors, i.e., the HOME position sensors, are positioned 0.1 inches before a mechanical stop. For the Z axis the HOME position is in the up, fully retracted, position 0.1 inches before a mechanical stop. The END opto sensor for each axis is at the end of travel opposite to the HOME sensor. The END opto sensor limit is encountered before hitting a mechanical stop. Viewing the CE instrument from the front, END corresponds to autosampler head 204 being positioned to the left side, in the front position and fully down. The third sensor associated with each axis is a reference (REF) sensor. For both the X and Y axis, the REF sensors are located at running electrolyte bottle RE1. For the Z axis, the REF position was chosen as being 0.250 inches down from the Z axis HOME position. In another embodiment, the REF sensors are not used, and each axis has only the HOME and END sensors.

One of the functions of the autosampler is to sense the electrolyte level in the running electrolyte bottles RE1-RE4 using thermistor 202 which is encased in a stainless steel sleeve. Thermistor 202 is heated and in air is at a temperature of approximately 10 degrees above the ambient temperature. The thermistor's resistance, when it is lowered into the cooler room temperature electrolyte, changes rapidly. Conditioning electronics in position sensor interface circuit 214 sense this change and signal 68000 VME CPU 100, the system controller, that the sampled electrolyte bottle contains an electrolyte. Autosampler head 204, which moves end 110A of capillary tube 110 and HV electrode 103A as a pair, also carries level sensing thermistor 202 and Teflon running electrolyte replenish tube 203 as a pair. Replenish tube 203 and thermistor 202 are mounted on head 204 about one inch away from capillary tube 110 and electrode 103A. Replenish tube 203 and thermistor 202 as a pair can be lowered one half inch beyond the tip of capillary tube 110 by a solenoid driven plunger. When the solenoid is de-energized, replenish tube 203 and thermistor 202 are retracted one half inch above tip 110A of capillary tube 110. When the autosampler is sampling or taking an acquisition run, the solenoid is de-energized and so replenish tube 203 and thermistor 202 are retracted above tip 110A of capillary tube 110. When the autosampler is sensing the presence of liquids, replenish tube 203 and thermistor 202 are extended beyond capillary tube 110 by the plunger. During a running electrolyte replenish cycle, replenish tube 203 and thermistor 202 are inserted by autosampler head 204 into the RE bottle near the top of the bottle to sense when the proper electrolyte level has been reached.

With replenish tube 203 and thermistor 202 suspended on autosampler head 204, the running electrolyte bottle liquid levels must be tested in series. Any of the running electrolyte bottles RE1, RE2, RE3, R34 (FIGS. 6b′-5b″) can have its level sensed, but only running electrolyte bottles having the same electrolyte can be replenished because in this embodiment, the capillary electrophoresis instrument has only one running electrolyte supply bottle. Cross contamination between electrolytes is not a problem.

Since the running electrolyte bottle, end 110A of capillary tube 110 and Pt electrode 103A can have 30 KV present during a test, a proper spacing of about 2.5 cm must be kept between the capillary/electrode combination and any metal surface. Capillary tube 110 and electrode 103A are held parallel to each other, approximately 0.125 inches apart, by autosampler head 204, for a distance of about 2 cm.

In one embodiment, thermistor 202 has a resistance of 10K ohms at 25° C. and a response time including electronic circuit delays of two seconds upon entry into the electrolyte. A thermistor such as that manufactured by YSI under part number 44106 is suitable for use in the autosampler.

Two identical stepper motor controllers 208, 209 are used to control the autosampler stepper motors 205, 206, 207. Each controller can independently control two stepper motors. Since the autosampler has three motors, second controller 209 has one spare motor controller.

Stepper motor controller cards 208, 209 are 3U style cards which are controlled by 68000 CPU 100. Stepper motor controllers 208, 209 communicate with 68000

CPU 100 via VME bus connector P1. The stepper motor controller can provide either full or half step outputs to motor driver circuits 210, 211, 212. The signals from autosampler position sensors (HOME, REF, END), described above, are supplied to stepper motor controllers 208, 209 for each axis. Controller card 208 is for the X and Y axis while controller card 209 is used for the Z axis. In one embodiment, cards 208, 209 are programmed for half-stepping with a maximum output rate of 1000 half-steps per second. The stepper motor controllers are programmed to control 4 phase motors and receive signals from three limit switches per autosampler axis where the signals received are TTL level compatible active low. The base address for the X axis and Y axis controller in FF00XX, while the base address for the Z axis controller is FF01XX. A controller such as that manufactured by Matrix Corporation and supplied under Part No. MS-DSC is suitable for use in the CE instrument.

Motor driver circuits 210, 211, 212 function as power drivers for four phase stepper motors 205, 206, 207 respectively. The phase input signals from stepper motor controllers 208, 209 are amplified and sent to a stepper motor 205, 206, 207. Each motor driver circuit generates a unipolar output drive signal. The CE instrument uses three of these boards—one for each axis of the autosampler. A motor driver such as that provided by Matrix Corporation under part number USD with 8 amps per phase can be used.

The position sensor interface 214 is mounted on autosampler head 204. The position sensor interface contains no electronics. The position sensor interface simply routes the wiring for the Y and X axis stepper motors 206, 207 to autosampler interface circuit 213 and provides a physical location for the three position sensors (HOME, REF, END) associated with each axis, as described above. The infrared opto sensors used for position sensing are Opto 22 (OPT-865).

Autosampler interface circuit 213 provides the interface electronics for all of the autosampler position sensors; interface electronics for sensing when running electrolyte level sensor 202 is in the non-extended position; interface electronics for sensing when the sample tray door is closed; a signal to open the sample door; and a common interface path between the X, Y an Z stepper motors 205, 206, 207 and the three motor driver circuits 210, 211, 212. While one embodiment of the interface between system controller 100 and stepper motors 205, 206, 207 has been described, this embodiment is illustrative only and is not intended to limit the scope of the invention. In view of the principles of this invention, one skilled in the art can use other circuit configurations to interface controller 100 and the stepper motors. A summary of the characteristics of the autosampler and sensors in the autosampler is given in Table 1.

TABLE 1

| | |
|---|---|
| **Autosampler Total Travel** | |
| | X – axis = 0.0026 inches/step |
| | Y – axis = 0.0026 inches/step |
| | Z – axis = 0.004 inches/step |
| **Maximum Travel Time** | |
| | X – axis = 2 inches/sec. |
| | Y – axis = 2 inches/sec. |
| | Z – axis = 0.8 inches/sec. |
| **Maximum Steps/Second Provided by the Controller** | |
| | X, Y – axis = 1000 half steps/sec. |
| | Z – axis = 1000 half steps/sec. |

TABLE 1-continued

| | |
|---|---|
| **Positional Accuracy Required** | |
| | X, Y – axis = 0.040 inches |
| | Z – axis = 0.010 inches |
| **Carrier/Door Release Solenoid** | |
| | Operating = +12 vdc – normally not powered. |
| | Power Dissipation Continuous Duty = 2.5 watts |
| | Life Expectancy = $2.5 \times 10^6$ cycles |
| | Part Number = R8X7DC-12 |
| | Manufacturer = Regdon |
| **Positional Sensors** | |
| (1) | X, Y, Z axis opto interruptor (infrared) three for each axis representing the HOME position, REF position, and END position |
| (2) | Door Closed opto interruptor (infrared) |
| (3) | Level Sensor HOME position opto interruptor (infrared) |

The autosampler of this invention makes capillary electrophoresis a true instrumental method of analysis. Unlike the prior art methods which contained only a single electrolyte and required manually positioning the sample container, the electrodes, and the electrolytes, the autosampler automatically introduces the sample into the capillary tube and can move the capillary tube to any one of four running electrolyte bottles. Further, as described below, the autosampler in conjunction with the replenishment system can change the electrolyte in any one of the four running electrolyte bottles. Hence, manual intervention for capillary electrophoresis testing is no longer required.

A first function of detector module 104 is to excite the sample passing through capillary tube 110 in sample region 110C with UV light from xenon flash lamp 105A and at a 90 degree angle to the incident light from lamp 105A measure the fluorescence emitted by the sample in capillary tube 110. A second function of detector module 104 is to illuminate capillary tube 110 at a 180 degree angle from the entrance slit to polychromator 106 so that the detector module can simultaneously measure absorbance.

The main components of detector module 104, as illustrated in FIGS. *5b′*-*5b″* are: polychromator 106; xenon flash lamp 105A; xenon flash lamp power supply 215; deuterium lamp 105B; deuterium lamp power supply 216; diode array 217; capillary tube 110; and a capillary tube holder (not shown).

In one embodiment, the polychromator housing is fabricated from a single piece of aluminum which has been stress relieved. A holographic concave grating 218 is mounted inside the aluminum housing and is positioned to disperse the incoming light into its component wavelengths which are in turn focused by grating 218 onto a diode array 217. A grating used in one embodiment was 37×37 mm with 560 grooves per mm and a radius of curvature of 97 mm. Such a grating is manufactured by American Holographics, and provided under catalog number 456.20.

The geometry of polychromator 106 is designed so that grating 218 spreads the incoming light over the plane of photodiode array 217. For the previously described grating, the centers of the adjacent photodiodes are separated by wavelengths of about 16 nanometers. Photodiode array 217 has 35 identical elements which are sensitive to the wavelengths of interest. However, only 16 photodiodes are currently utilized, five for UV absorbance measurements and ten for fluorescence measurements. Also, one diode is used to generate a reference signal in UV absorbance measurements. The wavelengths of light, the corresponding diode of the array selected, and the dye names, which generate fluorescent light at the specified wavelength, are listed in Table 2. In Table 2, two embodiments are given. In the first embodiment, sixteen channels are used as described above. In the second embodiment, eighteen channels are used and the two additional channels are identified in Table 2.

TABLE 2

| UV Absorption Measurement | | |
|---|---|---|
| Wavelength | Diode Array Number | |
| 214 nm | D1 | Absorbance |
| 230 nm | D2 | Absorbance |
| 246 nm | D3 | Absorbance |
| 262 nm | D4 | Absorbance |
| 278 nm | D5 | Absorbance |
| 422 nm | D15 | Absorbance Reference |

| Fluorescence Measurement | | |
|---|---|---|
| Wavelength | Diode Array Number | (Wavelength) Dye |
| 454 nm | D16 | (450–470) Coumarin, (450) OPA, (460) Hoechst |
| 470 nm | D18 | (475) Fluorescamine |
| 486 nm | D19 | |
| 502 nm | D20 | Used only for 18 channel detector |
| 518 nm | D21 | (520) Fluorescein |
| 534 nm | D22 | (520–550) NBD |
| 550 nm | D23 | (550) Rhodamine, (550) Dansyl |
| 566 nm | D24 | (560) Eosin, (570–580) Trimethylrhodamine |
| 582 nm | D25 | (580–590) Ethidium Bromide, Lissamine Rhodamine |
| 598 nm | D26 | |
| 614 nm | D27 | (620) Texas Red |
| 630 nm | D28 | (633) HeNe Laser Used only for 18 channel detector |

Diode array 217, which is mechanically mounted with two preamp boards (FIGS. 11*a*'-11*a*'' and 11*b*'-11*b*''), is adjustable for fine tuning the wavelength calibration. The adjustment allows moving the array through 4 mm of the spectrum. When the alignment is complete, two lock down screws are tightened.

The polychromator housing in addition to housing grating 218 also provides an optically rigid mounting surface for xenon flash lamp 105A, the capillary tube holder (not shown), UV reference preamp 219, signal preamp 220, filter 221, deuterium lamp 105B, and glass cover slip 222. A more detailed layout drawing of detection module 104 is shown in FIG. 7.

For a CE fluorescence measurement, high energy xenon flash lamp 105A excites the sample in capillary tube 110 with ultraviolet light. The broadband xenon light pulse is filtered with a 340 nm filter 221. The range of wavelengths from lamp 105A and the wavelengths transmitted by filter 221, described more completely below, are illustrated in FIG. 13*a*. The range of fluorescent wavelengths excited by the light passed through filter 221 is illustrated in FIG. 13*c*.

Flash lamp 105A, flash lamp socket, and discharge capacitor are housed in a steel enclosure 223 which in turn is mounted on polychromator 106 assembly. As described more completely below, the lamp arc is precisely aligned with respect to capillary tube 110. Lamp assembly 223 is designed so that a replacement flash lamp needs no alignment upon installation. However, if a small adjustment is necessary, a 3 point screw mechanism gives an additional 0.010 inch adjustment of the arc position. Lamp assembly 223, in one embodiment, contains Hamamatsu xenon flash lamp (L2436), Hamamatsu flash lamp socket (E2438), and a 0.1 uf capacitor with WVCW 3000 volts such as Condenser Products Company (KMOC-3M01ES). Lamp assembly 223 is connected to xenon flash lamp power supply 215 by a shielded cable.

Xenon flash lamp power supply 215 charges the 0.1 uF storage capacitor to 1000 vdc. When a trigger signal is received from 68000 CPU 100, the stored energy is discharged into xenon flash lamp 105A creating a high intensity light pulse. Xenon flash lamp 105A and power supply assembly 215 are capable of producing a light pulse at a maximum rate of 100 Hz.

For a CE absorption measurement, deuterium lamp 105B generates short wavelength UV light with very little light output above 300 nm (See FIG. 13*b*). This light is reflected by a mirror 308 onto sample region 110C of capillary tube 110. Deuterium lamp 105B is described in further detail below.

Deuterium lamp power supply 216 provides a high DC voltage for the electrodes of deuterium lamp 105B and a trigger voltage to initiate discharge of deuterium lamp 105B. The anode current is supplied through a floating constant current regulator/preregulator circuit and a voltage feeback loop maintains a constant 12-volt drop across the current regulator/preregulator circuit; irrespective of the load or line conditions. The starting circuit in power supply 216 provides a ramped high voltage pulse to deuterium lamp 105B, and at the moment of ignition of the deuterium lamp, this voltage is instantaneously removed. The lamp discharge is maintained by the current regulator circuit. A deuterium lamp power supply 216 having these characteristics, is provided by Mimir Instruments, Model No. 430.

The polychromator spreads the wavelengths of emitted light, shown in Table 2, onto a 35 element array of which only 16 elements of diodes are used in one embodiment. An array manufactured by Hamamatsu under part number S2313-35Q was used in one embodiment. The specification for this array are given in Table 3.

TABLE 3

| | |
|---|---|
| Number of Elements: | 35 |
| Dark Current: | 150 pA @ VR = 10 v |
| Junction Capacitance: | 140 pF @ VR = 10 v<br>60 pF @ VR = 0 v |
| Spectral Range: | 190–1050 nm |
| Peak Wavelength: | 720 nm |
| Radiant Sensitivity: | 80 ma/W @ 200 nm<br>230 ma/W @ 930 nm |
| Diode Element Size: | 4.4 × 0.94 mm |
| Effective Area: | 4.1 $mm^2$ |

The detector module 104 consisting of deuterium lamp 105B, mirror 308, xenon flash lamp 105A, filter 221, glass cover slip 222, polychromator 106 including grating 218 and photodiode array 217, provides a significant enhancement in fluorescence and absorption measurement techniques over prior art detectors. UV absorption and fluorescence measurements are performed by a single device. The high sensitivity of prior art discrete channel detectors is maintained and a multiplicity of spectral information is obtained from photodiode array 217.

The signals from diode array 217 are individually amplified by discrete channels so that the noise introduced by the scanning of prior art photodiode arrays is not present. Further, the detector is maximized for sensitivity rather than spectral resolution by monitoring a few wavelengths with 16 nm resolution rather than 400 wavelengths at 2 nm resolution as with the prior art diode array detector. This is most important for the fluorescence measurements, as the emitted fluorescent light is about 30 nm at full width, half height (FWHH). In this embodiment, the digital signals, derived from the output signal of several diodes, can be added for the best signal to noise measurement, without degrading the UV absorbance measurements which need better spectral resolution.

The detector preamp circuit 220 (FIGS. 11*a*'-11*a*" and 11*b*'-11*b*") contains diode array 217, 16 low noise amplifiers, and the diode biasing selector. Sixteen preamps are associated with the six absorbance diodes and the ten fluorescence diodes as defined in Table 2. The diode biasing selector is a signal which switches the common diode cathodes between +12 V for fluorescence measurements and ground for absorbance measurements. The diode biasing minimizes the capacitance of the diodes for fast pulse response for fluorescence measurements and minimizes the dark current for absorbance measurements. If both detection modes are required, the bias is applied.

The fluorescence preamp circuit provides an additional stage of gain for the 16 channels. The 10 fluorescence channels are AC coupled (pulsed) while the 6 absorbance channels are DC coupled (continuous).

A fluorescence signal processor circuit 225 (FIGS. 12*a*'-12*a*", 12*b*'-12*b*" 12*c*'-12*c*" and channels of fluorescence pulse data and xenon flash lamp reference data into DC voltages which are subsequently processed by A/D converter 227 into 12 bit digital data. The 11 channels of information are each input to fluorescence signal processor circuit 225 (FIGS. 12*a* through 12*d*) in the form of a pulse between 5 and 20 microseconds wide and a peak amplitude of approximately 20 mv. These signals are amplified, integrated and sent to a sample and hold amplifier. The gating time and the constants in circuit 225 are selected such that any continuous signal, which may be generated by longer wavelength light from deuterium lamp 105B upon the fluorescence photodiodes, as defined in Table 2, is effectively filtered from the input signals.

Three additional voltage signals are supplied to fluorescence signal processor circuit 225 from system I/O controller 228. These three voltage signals are a voltage monitor signal VMON from high voltage power supply 103, a current monitor signal IMON from the capillary holder, which indicates the current through capillary tube 110, and a vacuum monitor signal from replenishment system interface 229.

These three signals are simply routed to A/D converter 227. The six absorbance preamp signals are also not processed. The absorbance preamp signals are sent to absorbance signal processing circuit 226. Fluorescence signal processing circuit 225 is on a 6U style printed circuit card suitable for mounting in a VME chassis.

Absorbance signal processor circuit 226 is also on a 6U style printed card which resides in the VME chassis. As described above, the six absorbance signals from preamp 220 are supplied to circuit 226 via fluorescence signal processor circuit 225. The five channels of data and the reference channel are processed and then routed back to the fluorescence signal processor 225 and subsequently to A/D circuit 227. Analog ratioing of the absorbance channels with a deuterium light source reference signal, generated by the photodiode in photodiode array 217, and an auto zeroing function are performed by absorbance signal processor 226. The analog signal processing is required to obtain the accuracy needed for absorbance measurements because the twelve bits of information from analog to digital converter 227 are not suitable for direct processing of the absorbance data from preamp circuit 220. The absorbance signal processor circuit 226 is essentially a DC circuit because the absorbance input signals are continuous rather than pulsed. Accordingly, the coupling and time constants in this circuit are selected to minimize any signals generated by short wavelength fluorescence interacting with the absorbance photodiodes.

In yet another embodiment, analog to digital converter 227 is selected to provide 16 bits of digital information, i.e., 16 bit words. This word length provides the required accuracy and so absorbance signal processor 226 is not needed. The absorbance signals are passed directly to analog to digital converter 227. Alternatively, analog to digital converter 227 may be maintained in the capillary electrophoresis instrument and another analog to digital converter which generates 16 bits of digital data used to replace absorbance signal processor 266. In this case, the absorbance signals from fluorescence signal processor 225 are converted by the 16 bit analog to digital converter and the digital data is supplied directly to system controller 100. The path from the present absorbance signal processor circuit 226 through the fluorescent signal processor to the analog to digital converter 227 is not utilized in this embodiment.

In yet another embodiment, very low cost signal channel 16 bit CMOS chips (Crystal Simiconductor Corp. part number CS5501) are used to process the signals from the absorbance photodiodes. These components are used in a custom printed circuit board instead of the multiplexed high speed 16 bit analog to digital converter from Matrix, described above.

Xenon flash lamp reference preamp 219 samples the filtered light from xenon flash lamp 105A. The output signal of preamp 219 is sent to fluorescence signal processor circuit 225. This signal is used to initiate the timing sequences and signal processing of fluorescent data. The reference channel is also digitized by A/D converter 227. Since a xenon flash lamp light pulse varies in amplitude from pulse to pulse, the signal processing software in the 68000 CPU 100 ratios all of the fluorescent channels with the reference channel after the digitization of the data.

Capillary tube 110 (FIGS. 5*b*'-5*b*") is made of fused silica and is manufactured by Polymicro, of Arizona. Tube 110 is coated with polyamide to allow bending of the tube without shattering. This coating allows capillary tube 110 to flex as the autosampler moves sample end 110A of capillary tube 110 from a sample well to a selected running electrolyte bottle. The portion 110C of capillary tube 110 at detector 104 must be transparent to the UV light pulse and the light from the deuterium lamp. Therefore, the polyamide coating is burned away for a length of about 10 mm at location 110C where the light enters polychromator 106 after first passing through capillary tube 110. The outer protective coating of polyamide must be burned off for a length of about 1 cm with a flame prior to mounting in the detector. An ordinary propane cigarette lighter is used for this purpose.

The location of sample region 110C with respect to end 110B of capillary tube 110 is not critical so long as sample region 110C can be placed in capillary holder 232 and end 110B is near the bottom of detector electrolyte bottle 113. The exposed silica tube is very brittle and so this 10 mm portion of capillary tube 110 is rigidly held in place in capillary tube holder 232, as described below. Capillary tube 110 has an typical inner diameter of about 50 microns, an outer diameter of about 320 microns and a length which ranges from about 30 cm to about 75 cm.

Capillary tube holder 232, as illustrated in FIGS. 8*a* through 8*g*, holds the capillary tube 110 stationary; supports the two imaging lens holders for light from xenon UV lamp 105A and light from deuterium lamp 105B; and provides a vacuum tight connection to detector electrolyte bottle 113 for stationary end 110B of capillary tube 110. Detector electrolyte bottle 113 also has two teflon tubes which are part of the replenishment system. One teflon tube, which has an outer diameter of 0.125 inches, provides up to 22 inches of vacuum during a sample introduction. The other teflon tube, which has a 0.063 inch outer diameter, is used to evacuate spent electrolyte and to add fresh electrolyte, as described below.

Figure 8B:
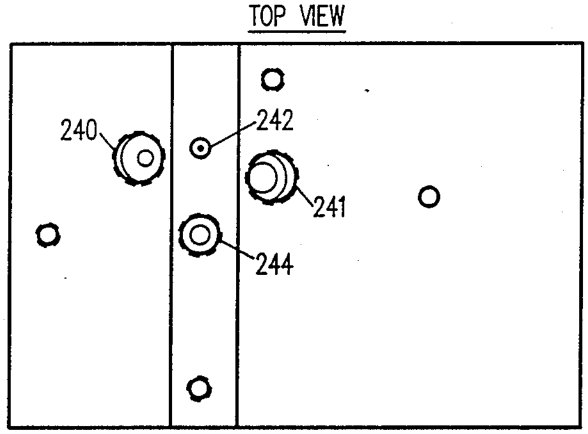
Figure 8A:
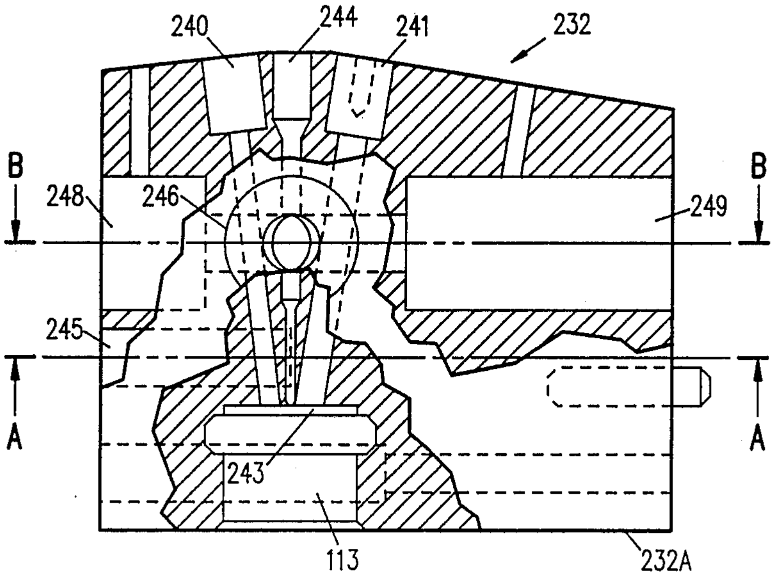
Figure 8C:
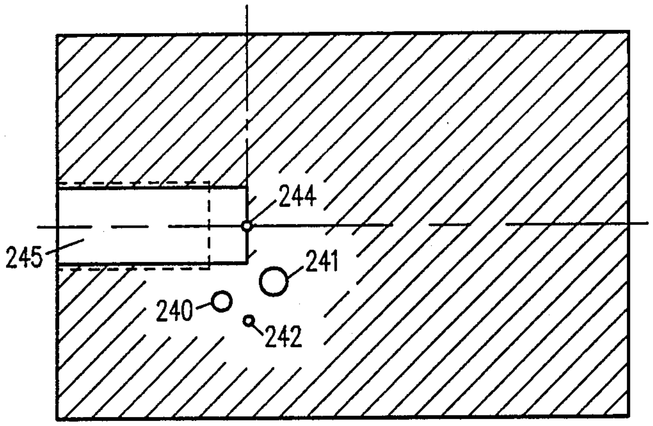
Figure 8D:
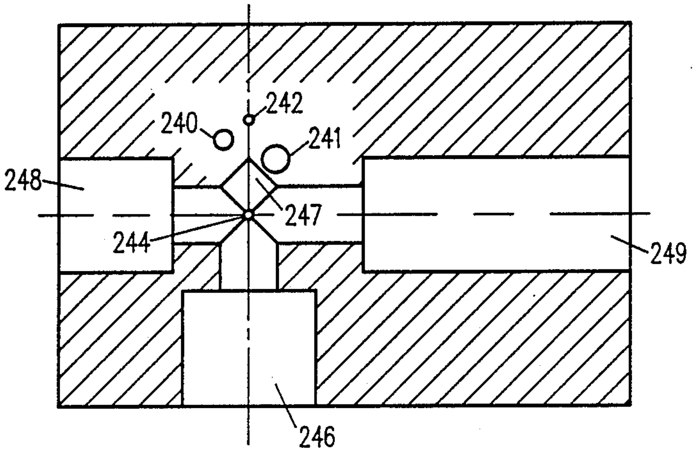
Figure 8E:
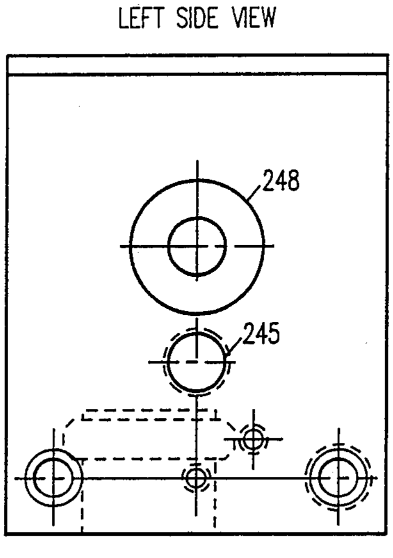
Figure 8F:
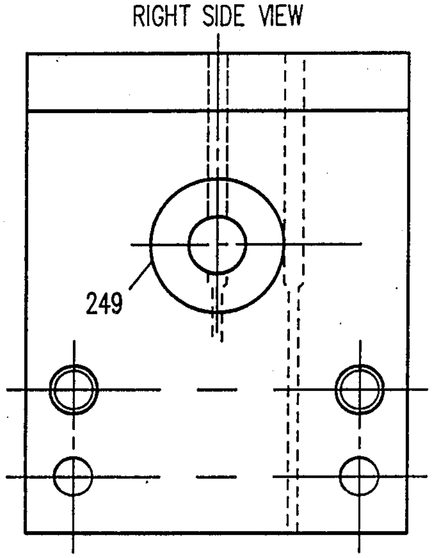
Figure 8G:
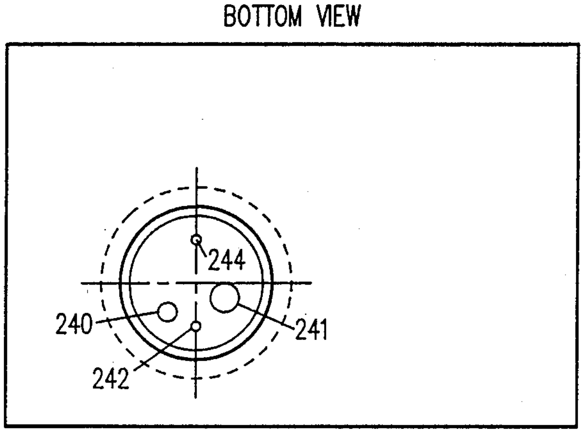

As shown in FIGS. 8*a* through 8*g* capillary tube holder 232 is a multiple-purpose element. First, at the bottom 232A of holder 232 is detector electolyte bottle 113 and a Viton O-ring 243. The bottle is mechanically held in place against O-ring 243 so as to form a vacuum-tight seal. The two teflon tubes are inserted through holes 240, 241. Platinum electrode 103B is inserted through hole 242 which extends through capillary holder 232. The electrode is passed through hole 242 and then glued into position. Capillary tube 110 is passed through hole 244 which also extends through the body of capillary tube holder 232. Hole 244 is half round at the bottom of hole 245 in which capillary tube 110 can rest. A threaded hole 245 is provided for use in securing capillary tube 110 in capillary tube holder 232. Hole 245 is threaded to accept a screw 390 (FIG. 14*a*) which has a free-turning disc 391 (FIG. 14*b*) mounted on the end going into holder 232. The screw is threaded into the sample holder until the disc encounters a captive O-ring, and after the disc contacts the O-ring an additional quarter turn of the screw securely fastens capillary tube 110 in place without damaging tube 110. Ultraviolet light from xenon lamp 105A enters the capillary tube through port 246. An apex 247, shown in section B—B of FIG. 8*d*, is designed to trap any of the light passing through capillary tube 110 so that the light is not reflected into polychromator 106. The light from deuterium lamp 105B enters through port 248. Both the light from deuterium lamp 105B and the fluorescent light from the sample exit holder 232 to polychromator 106 through port 249. The other features in capillary tube holder 232, as shown in FIGS. 8*a* through 8*g*, are used to secure capillary tube holder 232 to polychromator 106, xenon lamp 105A and deuterium lamp 105B, as shown in FIG. 7.

A programmable high voltage (0–30 KV) power supply 103 introduces sample components electrophoretically into capillary tube 110 prior to the electrophoretic separation. As shown in FIGS. 6*b*′–6*b*″ two platinum wire electrodes 103A, 103B electrically connect high voltage power supply 103 to detector electrolyte bottle 113 and to a selected running electrolyte bottle respectively. Both bottles contain an electrolyte solution and capillary tube 110 connecting the two bottles is filled with electrolyte, as previously described. After autosampler head 204 moves electrode 103A and sample end 110A of capillary tube 110 to one of the sample wells containing sample solution, a voltage, typically 30 KV, is applied across electrode 103A and platinum electrode 103B in detector electrolyte bottle 113. The electrical circuit is now complete and the sample components electrophoretically flow from the sample well into capillary tube 110. The voltage is then turned off and autosampler head 204, under the direction of 68000 CPU 100, moves capillary tube 110A and electrode 103A into the electrolyte of a running electrolyte bottle and a high voltage is again applied. The sample now travels through tube 110 from running electrolyte bottle RE1 (FIGS. 5*b*′–5*b*″) past polychromator 106 into detector electrolyte bottle 113, separating as it travels.

The CE instrument has two different HV power supply 103 configurations, a plus 0 to plus 30 KV programmable in 7.32 volt increments, and a minus 0 to minus 30 KV programmable in 7.32 volt increments. Only one polarity unit can be installed at a time, but the units are designed to be easily exchanged by the user.

The specifications for high voltage power supply 103 are given in Table 4.

TABLE 4

| | |
|---|---|
| **Option 1** | |
| Output Polarity: | Plus (0–30 KV) |
| Manufacturer: | Gamma High Voltage Research, Inc. |
| Part Number: | OEM version in custom case like #RC10 - 30 P-VM |
| Voltage Monitor Output: | Plus (0–3 vdc) corresponds to plus (0–30 KV) |
| Maximum Continuous Output Current: | Plus 330 microamps |
| **Option 2** | |
| Output Polarity: | Minus (0–30 KV) |
| Manufacturer: | Gamma High Voltage Research, Inc. |
| Part Number: | OEM version in custom case like #RC10 - 30 N-VM |
| Voltage Monitor Output: | Minus (0–3 vdc) corresponds to minus (0–30 KV) |
| Maximum Continuous Output Current: | Minus 330 microamps |
| **Common specifications for both options 1 and 2:** | |
| Input Voltage: | +28 vdc +/− 10% @ 800 ma |
| Line Regulations: | 0.01% maximum |
| Load Regulations: | 0.01% maximum |
| Ripple: | 0.05% maximum |
| Output Connector: | Alden 8111LSFP |
| Input Connector: | 9 pin Sub-D |

CPU controller 100, sometimes called the system controller, used in the CE instrument is a VME 30 U style 10 Mhz 68000 microprocessor VME bus master. Controller 100 controls all electronic processing and control functions and communicates serially (RS232) with OC-AT 107. The functions of controller 100 are described more completely below. The controller's specifications are listed in Table 5.

TABLE 5

| | |
|---|---|
| Manufacturer: | Matrix Corporation |
| Part Number: | MS-CPU00B |
| EROM: | 256K zero wait state EROM |
| SRAM: | 64K zero wait state, dual |

TABLE 5-continued

| | |
|---|---|
| | ported to the VME bus static RAM, with battery back up |
| Serial Ports: | Two RS232 serial communication ports. Only one serial port is used by the CE instrument. It is used to communicate to the PC-AT at 9600 baud |
| Timer: | 16 bit programmable timer for generating periodic interrupts |
| NOVRAM: | 256 bit non-volatile RAM |
| Front Panel: | Software abort and reset switch run and fail light |
| Size: | 3U |

The system software was written in Forth and was compiled using Laboratory Microsystems, Inc. Metacompiler for the 68000. The machine code is presented in Appendix A and incorporated herein by reference. To use the machine code a reference address of 4000 H must be used upon loading the program.

The overall system electronics architecture was planned to minimize interconnection wiring. Circuits having a "*" in FIGS. *5a'*-*5a''* and *5b'''*-*5b''* are mounted in a 6U style 7 slot VME card cage. The function of the VME chassis is to link the 68000 CPU VME bus controller to the other VME cards used by the CE instrument. The chassis is configured with seven VME slots, three of which are 3U style cards and four of which are for the 6U style cards. The mother board for the VME chassis has signal terminating resistors designed into the back plane. The chassis is made by ELMA Electronic Inc., part number 11-216-42-615.

A/D converter 227 changes analog voltage signal channels to digital signals which are then read and processed by 68000 CPU 100. The analog signal channels are:

1. 5 Absorbance Channels
2. 10 Fluorescence Channels
3. HV Power Supply Voltage (VMON)
4. HV Power Supply Current (IMON)
5. Vacuum Sensor Voltage
6. Xenon Flash Lamp Reference Signal
7. Deuterium Lamp Reference Signal The specifications for A/D converter 227 are listed in Table 6.

TABLE 6

| | |
|---|---|
| Manufacturer: | Matrix Corporation |
| Part Number: | MS-AD12E |
| Resolution: | 12 bits |
| Number of Channels: | 32 single ended |
| Input Range: | +(0-10 v) |
| Programmable Gains: | 1, 10, 100, 500, 1,000 |
| Settling Time: | 20 microseconds |
| Input Impedance: | 60 Megaohms. |
| Size: | 3U |
| Base Address: | FF0200 |

The replinishment system is described more completely below, but briefly, replenishment system interface 229 transfers signals from system controller 100 which turn ON and OFF valves V1 through V5, and transfers signals about the liquid levels in waste bottle 251, running electrolyte supply bottle 252, and detector electrolyte supply bottle 253 to controller 100. Replenishment system interface 229 also measures the vacuum present in waste bottle 251 (up to 22 inches of Hg).

The system I/O controller is a 6U VME card which resides in the VME chassis. Its basic function is to provide an I/O interface between 68000 CPU 100 and autosampler interface circuit 213, fluorescence signal processor circuit 225, replenish system interface 229 and front panel 230 displays.

System I/O controller 228 receives signals on the status of the interlocks and the position of the running electrolyte level sensor position as to being extended or not. Circuit 228 also passes to the fluorescenc signal processor 225 high voltage and current readings as well as the vacuum reading from waste bottle 251 and various control signals. In addition, circuit 228 passes signals which control the read the status of replenishment system interface 229; which control the biasing voltage to photodiode array 217; which fire xenon flash lamp 105A; and which turn on and off deuterium lamp 105B. System I/O controller circuit 228 also passes control voltages 0 to 10 V to power supply 103 and two channels of D/A data to the strip chart recorder outputs.

As described previously, the CE instrument can use various high voltage power supplies. In addition to those described, a power supply which rapidly switches from a positive high voltage through zero to a negative high voltage can be used in the CE instrument. The system I/O controller circuit 228 includes a high voltage rectifier and a current rectifier for processing the VMON signal and the IMON signal respectively from a rapidly switched power supply.

The CE instrument contains two power supplies. The first power supply is a linear power supply which provides +28 vdc at 1.0 amps to HV power module 103. The +28 volt supply is manufactured by Power One Incorporated, part number HB28-1-A.

The second DC power supply is a switching power supply which provides:

+5 vdc @ 12 amps for the digital logic;

±12 vdc @ 1.5 amps for the analog electronics; and

+12 vdc @ 5.0 amps for the motors and relays.

The manufacturer is SQV, part number SQV100-1222-4.

A detector capable of simultaneous measurements of fluorescence and absorption of a sample in a thin capillary having an inner diameter of about 50 microns and an outer diameter of about 320 microns as in the capillary electrophoresis instrument presents many problems. The light from the light sources must be focused such that light is incident only upon the sample in capillary tube 110. If ambient light passes around capillary tube 110 and enters polychromator 106 or reenters capillary tube 110, the ambient light inhibits accurate measurement of the absorption spectrum and the fluorescence spectrum. The small size of the capillary makes simultaneous measurements using separate polychromators for absorption and fluorescence impractical so that both spectra must be measured by a single polychromator.

The detector 104 of this invention uses a photodiode array 217 and a single polychromator 106, as previously described, for both fluorescence and absorption measurements. Since in absorption measurements, wavelengths less than 300 nanometers are primarily of interest and in fluorescence measurements wavelengths greater than 400 nanometers are of interest (FIG. 13*c*), the various wavelengths provided by polychromator 106 to photodiode array 217 are sufficient for both measurements.

There is some overlap of excitation light from the flash lamp assembly onto the diodes of less than 300 nm and some visable light from the deuterium lamp assembly falling on the diodes above 400 nm. However, the circuitry and measurement methods of this invention eliminate most of the potential problems introduced by this overlap.

The first step in minimizing the effect of the overlap in the selection of the light sources. Xenon flash lamp 105A in the capillary electrophoresis instrument provides light having wavelengths from less than 200 nanometers to greater than 650 nanometers (FIG. 13*a*). Since xenon flash lamp 105A is used for the fluorescence measurements, the entire bandwidth of light generated is not required, but rather a specific wavelength which causes a wide range of samples to fluoresce is needed. Accordingly, the excitation light from flash lamp 105A is filtered by a ½" diameter filter having a broad band pass centered about a 340 nanometer wavelength. (FIG. 13*a*). Accordingly, visible light, which would interfere with the fluorescence measurement, is rejected. Filters having such a characteristic include a Hoya number U340 filter or Schott number UG11 filter. Filter 221 was coated, in one embodiment, with a single layer anti-reflection coating on each side which was optimized for minimum reflectance at 340 nanometers. Xenon flash lamp 105A provides a pulse of light about 10 microseconds in duration.

Deuterium lamp 105B provides light having wavelengths of 200 nanometers and longer, but as the wavelength increases the light intensity decreases very rapidly (FIG. 13*b*). Thus, light from deuterium lamp 105B has only a small percentage of wavelengths greater than 300 nanometers, e.g., most of the light intensity from deuterium lamp 105B is less than 300 nanometers.

The difference between a continuous light source and a pulsed light source provides the means for eliminating problems caused by the overlap of the absorption spectrum and the fluorescence spectrum. The absorption spectrum represents a basically continuous output signal from the diode array while the fluorescence spectrum has an alternating current aspect caused by the pulsed light. Thus, the circuitry used to measure the absorption signals is effectively DC coupled so as to eliminate contributions from the fluorescent signals, i.e., the time constants and coupling reject high frequency signals, such as the fluorescence signals. Conversely, the circuitry used to measure the fluorescent signals are effectively AC coupled to eliminate contributions from the absorption spectrum, i.e., the time constants, coupling, and gating are such that continuous signals, such as the absorbance signals, are eliminated.

Finally, the longer wavelengths of light from deuterium lamp assembly 105B can excite some fluorescence. However, the magnitude of this fluorescence is sufficiently small that it is insignificant in comparison to the fluorescence excited by light from xenon lamp 105A. The use of two light sources in the CE instrument is illustrative only and is not intended to limit the scope of the invention. Using the principles of this invention, one skilled in the art could use a single light source with appropriate optical systems for both fluorescence and absorbance measurements. Further, the detector output signal processing systems, described previously, could be modified to accommodate detector output signals generated by a single light source.

To provide further accuracy in the measurements, as described previously, a xenon reference detector 219 and a reference diode in diode array 217 for deuterium lamp 105B are included in the capillary electrophoresis instrument. The reference signals provide means for correcting for amplitude variations of the source light. The reference diode for deuterium lamp 105B measures a long wavelength component from lamp 105B which is not absorbed. Since this wavelength is within the fluorescent spectrum, the coupling described above is used to separate the signal portion from deuterium lamp 105b from the signal portion from the fluorescent spectrum.

As described previously, the light from xenon flash lamp 105A must be precisely positioned so that the light is directly incident upon only the inner diameter of capillary tube 10. Further, since xenon flash lamp 105A has a finite lifetime, the apparatus holding xenon flash lamp 105A is designed to maintain proper alignment of the lamp's arc after replacement of flash lamp 105A. The arc 300 (FIG. 9, which is not drawn to scale) is aligned with a long axis parallel to a vertical plane 400 through sample region 110C. The housing of lamp 105A has fine adjustments which are used to provide da maximum fluorescence signal with a sample in capillary tube 110. The alignment of the cylindrical axis of lamp housing 105A with respect to optical axis 402 which is perpendicular to plane 400 passing through capillary tube 110 is not critical. Lamp 105A is attached to a mounting base 301 with a spring action strap 302 across the middle of lamp 105A. The end 303 of the lamp assembly has a pivot adjustment, which is implemented by a screw actuating a pad (not shown) protruding through mounting base 301. By adjusting the screw, arc 300 is aligned in plane 401 which is normal to optical axis 402 passing through arc 300. A pin (not shown) protruding through base 301 maintains the height of the arc on the optical axis of the instrument.

Immediately in front of xenon flash lamp 105A is a metal strip 304 having a slit which functions like a pinhole. The width of the slit is approximately fifteen times greater than the inner diameter of capillary tube 110 and the height of the slit is also approximately fifteen times greater than the height of sample region 110C in capillary tube 110.

Light from slit 304 encounters 340 nanometer filter 221, described previously, and after passing through filter 221, the filtered light is incident upon reference window 222. Reference window 222 is a microscope cover slip glass set at a 45 degree angle to optical axis 402 to reflect a sample of the ultraviolet light to reference detector 219. Reference window 222 is 0.1 mm thick and must be large enough to provide a clear aperture of 0.25 inches minimum diameter in a plane (not shown) perpendicular to optical axis 402. In one embodiment, reference window 222 has a magnesium fluoride antireflection coating on each side to reduce the total light reflected to reference detector 219 to about 3% of the irradiance from filter 221.

Light from reference window 222 encounters a first source imaging lens 305. Lens 305 and slit 304 are an imaging system. For reference slit 304, which is approximately fifteen times larger than the inner diameter of capillary tube 110, source imaging lens 305 has a 9.5 mm focal length, a 0.25 inch diameter and a is a plano-convex ultraviolet grade fused silica lens sold by Oriel under Catalog number 41115. For ultraviolet light, the focal length of lens 305 is actually 9.1 mm and the paraxial back focus is 7.7 mm. The back surface of lens 305, i.e., the surface closest to window 222, is located 0.314 inches in front of the center of capillary bore 244 of capillary sample holder 232 (FIG. 8*a*). This distance is established by a ray trace and the distance is shorter than the paraxial image position by an amount controlled by spherical aberration. After sample region 110C is encountered, holder 232 (FIG. 8*d*) has a conical hole 247 countersunk on the lens axis beyond capillary tube 110 to act as a trap for the excitation light.

The size of slit 304, described above, and source imaging lens 305 are an illustration of one embodiment only and are not intended to limit the scope of the invention. Other slit sizes and source imaging lenses can be used. The only requirement is that light incident upon sample region 110C must be directed to prevent polychromator 106 from receiving light from surrounding surfaces whose light reflecting properties are uncontrolled. To further limit the reflected light, the light passes through a black, light tight assembly.

The filtered UV light incident upon sample region 110C in capillary tube 110 causes the sample to fluoresce and the fluorescent light enters polychromator 106 at a 90 angle to the incident UV light.

Light from deuterium lamp 105B, used for absorption measurements, is on optical axis 403 (FIG. 9) passing directly through capillary tube 110 and into polychromator 106. Deuterium lamp 105B is a continuous extended light source and so a slit mask 307 is mounted in front of the source to provide an initial imaging of the light. Light from slit 307 encounters a mirror 308 which in turn reflects the light onto a lens 306. Lens 306 projects the light from slit 307 onto the bore of capillary tube 110 so as to provide maximum sensitivity. The incident light is focused so that light entering polychromator 106 passes through a path in sample region 110C, preferably a maximum path length. Hence, the width of slit 307 is limited so that the incident light falls on a region near the center of the diameter of capillary tube 110. Lateral adjustment of the slit position is made so as to obtain a maximum reading from polychromator 106 for a sample in capillary tube 110. If the slit is fixed, mirror 308 can be adjusted to align the slit image with the capillary tube.

Two different mirrors can be used in the CE instrument. In a first embodiment (not shown), a dichroic beam splitter filter is utilized as mirror 308. This mirror reflects wavelengths from about 190 to 350 nanometers and transmits wavelengths of about 400 to 700 nanometers. The range between 350 nanometers and 400 nanometers is a transition range. Hence, in this embodiment, mirror 308 is used as folding mirror for the ultraviolet light and as a window for the visible light. Hence, mirror 308 reflects the wavelength range from 190 to 350 nanometers onto lens 306 and passes the longer wavelengths from deuterium lamp 105B through mirror 308. In this embodiment, a reference detector is mounted so as to receive the longer wavelengths passed through mirror 308. The reference channel generates the signal used to adjust the absorbance signals for variations in intensity of lamp 105B.

In a second embodiment, illustrated in FIG. 9, a reflector mirror is used as a steering mirror 308 and all of the light from deuterium lamp 105B is reflected onto lens 306. In this embodiment, a sixth diode detector in diode array 217 is used as reference channel for measurement of variations in the amplitude of light from deuterium lamp 105B, as previously described.

The other elements of the detector are identical to those described previously for the fluorescence detector. However, the wavelength calibration adjustment is made by moving the detector assembly to get a selected pair of detector array elements to produce a specified ratio of signals for a given spectra light output from the calibration source.

In polychromator 106, the fluorescent light and the unabsorbed light from deuterium lamp 105B are incident upon a flat field concave holographic grating 218 (FIGS. 5*b*′-5*b*″) having a size of 37×37 mm with 560 grooves per millimeter. The grating can be obtained from American Holographic under Catalog number 456.20. This grating has an overall diffraction efficiency of about 30%. The grating is optimized to have an efficiency of about 33% at a wavelength of around 350 to 360 nanometers and the efficiency of the grating is something less than 30% at the long wavelength end of the grating around 600 nanometers.

The precise mounting of holographic grating 218 in polychromator 106 and the size of polychromator 106 are dictated by the manufacturer's specifications. For the grating described above, the polychromator housing wall has a thin edged aperture with a diameter such that an F/2.5 cone is formed from the slit position along the optical axis of the grating. The grating slit position is occupied by capillary tube 110. As described above, the region about capillary tube 110 is covered and baffled so that stray reflected light is prevented from falling on the internal walls of polychromator 106. However, should any stray light reach the internal walls of polychromator 106, the walls are relieved or milled out so as to keep them some distance from the cones of light from sample region 110C. In one embodiment, additional stray light rejection is provided by a baffle in the cavity of polychromator 106.

The grating is ultimately positioned so that the optical axis from the light source to the grating slit, and that from the grating slit to the vertex of the grating all lie in the same horizontal plane. As shown in FIG. 7, the polychromator housing wall is removed, and grating 218 is inserted and placed against four mounting brackets 275A, 275B which cover the corners of grating 218. The corners of grating 218 are not used and so this method of mounting grating 218 does not affect the efficiency of polychromator 106. Grating 218 is held in place by a fixture applied to the back side of grating 218. Photodiode array 217 is mounted on the polychromator housing so that the 214 nanometer wavelength light from grating 218 falls nominally at the middle of the first detector element. The circuit board containing photodiode array 217 is enclosed in a shielding box. The board is mounted so that the board can be adjusted ±2 mm in a horizontal direction along the plane of photodiode array 217. This adjustment provides means for wavelength calibration of the detector signals, as previously described.

The electrolyte replenishment subsystem of this invention is shown in FIG. 10. The electrolyte replenishment subsystem includes two 100 ml supply bottles 252, 253 which contain the running electrolyte and the detector electrolyte. Running electrolyte supply bottle 252 is connected to running electrolyte bottle RE1 by a ⅛ inch tube through valve V4 and detector electrolyte bottle 113 is connected by a ⅛ inch tube through valve V5 to supply bottle 253. A 500 ml waste bottle 251 is similarly connected by ⅛ inch tubing to running electrolyte bottle RE1 through valve V4 and to detector electrolyte bottle 113 through valve V5. Each of the bottles in replenishment system 410 has a thermistor level sensor, as previously described. A pump 254 capable of providing either a 22 inch Hg vacuum or pressure is coupled to running electrolyte supply bottle 252 and to detector electrolyte supply bottle 253 by a valve V1 and to waste bottle 251 by a valve V2. Waste bottle 251 also has a sensor which is connected to a vacuum sensor gauge. Valve V1 is a pressure vent valve while valve V2 is a vacuum vent valve. Valve V3 is a timed injection valve while valves V4 and V5 are refill or purge valves for the running electrolyte bottle RE1 and the detector electrolyte bottle 113. FIG. 10 illustrates only a single running electrolyte bottle RE1, but, as previously described, autosampler head 204 moves the ⅛ inch tube and level sensor to any of the four running electrolyte bottles. Accordingly, in FIG. 10, running electrolyte bottle RE1 (FIG. 5b′-5b″) has been selected.

To empty and fill running electrolyte bottle RE1 the external data communication device 107 (FIGS. 5a′-5a″) provides system controller 100 in the capillary electrophoresis instrument with the command "PREPURGE" or "POSTPURGE" directed to a running electrolyte bottle. These commands are described more completely in Appendix B which is incorporated herein by reference. When system controller 100 receives either of these commands, controller 100 opens valves V1, V3 and V5 and closes valves V2 and V4. Next, the level sensor is lowered to the bottom of running electrolyte bottle RE1 and pump 254 is turned on to full vacuum. The pump continues to run until the level sensor in running electrolyte bottle RE1 senses that bottle RE1 is dry.

After bottle RE1 is dry, if controller 100 receives a "FILL" command (See Appendix B) for the running electrolyte bottle, the other level sensors are checked to make sure that replenishment system 410 is in a configuration suitable for proceeding with the refill operation. If the sensors show that system 410 is in a configuration for proceeding, i.e., an adequate liquid level is present in the bottles, the level sensors are raised to the "full" position. Conversely, if an error is detected in the check of the other level sensors, such as running electrolyte supply bottle 252 is empty, then the empty and refill cycle is aborted.

After the level sensors are raised to the "full" position, valves V2, V3 and V4 are opened and valves V5 and V1 are closed by system controller 100 and then pump 254 is turned on so that a positive pressure is created in running electrolyte supply bottle 252 and consequently the running electrolyte is transferred to running electrolyte bottle RE1. When the level sensor detects the electrolyte, pump 254 is turned off and system controller 100 proceeds with the next instruction.

Purging and filling of detector electrolyte bottle 113 is similar to the purging and filling of running electrolyte bottle RE1. However, in this process the commands are directed to the detector electrolyte bottle (See Appendix B). In this process, system controller 100 purges detector electrolyte bottle 113 by opening valves V1, V3 and V4 and closing valves V2 and V5. System controller 100 turns pump 254 on so that pump 254 creates a vacuum. Pump 254 runs until detector electrolyte bottle 113 is evacuated of electrolyte. After the evacuation, if "FILL" command is received, system controller 100 continues to refill bottle 113 by opening valves V2, V3 and V5 and closing valves V4 and V1. Pump 254 is then turned on so that detector electrolyte is pumped from detector electrolyte supply bottle 253 to detector electrolyte bottle 113.

While the replenishment system of this invention has been described using only one running electrolyte bottle, one detector electrolyte bottle, one waste bottle and two supply bottles, this illustration is not intended to limit the scope of this invention. In view of this description, one skilled in the art could use additional valves, waste bottles, running electrolyte or detector electrolyte bottles as well as multiple supply bottles.

The replenishment system has significant advantages over the prior art. This system eliminates manual intervention in capillary electrophoresis tests. Also, the ability to frequently and easily change the electrolyte is significant because the possibility of a degraded electrolyte distorting test results is eliminated. Accordingly, this invention not only makes capillary electrophoresis easier, but also makes such testing more reliable and reproducible.

Replenishment subsystem 410 is also used for a timed injection cycle which draws a sample from the microtiter tray into capillary tube 110. In this operation, system controller 100 (FIGS. 5a′-5a‴) first positions autosampler head 204 (FIGS. 5b′-5b″), using the X and Y stepper motors 205, 206, over the sample location in the microtiter tray and then uses Z stepper motor 207 to lower capillary tube 110 to reach the bottom of the sample. Next valves V1, V3, V4 and V5 are opened and valve V2 is closed. Then, in response to the command from external computer 107 (See Appendix B), system controller 100 turns on vacuum pump 254 and runs pump 254 until a specified vacuum level is reached. System controller 100 maintains the vacuum by toggling valve V2. System controller 100 then closes valve V3 for a specified time. The closing of valve V3 causes the sample to be drawn into capillary tube 110. After the specified time valve V3 is reopened and subsequently capillary tube 110 and the high voltage electrode 103A are moved to the running electrolyte bottle selected by commands to system controller 100.

System controller 100, as described above, receives commands from external device 107 and then controls the hardware within the capillary electrophoresis instrument so as to perform the desired tests. Controller 100 controls the three stepper motor controllers so as to position the capillary tube in a desired location, the level sensors, and the replenishment system. Controller 100 provides gain control to multichannel analog digital converter 227, which converts the analog high voltage power supply voltage and current signals, the pressure/vacuum signals and related parameters, as well as controlling the multichannel digital to analog converter which generates signals which in turn supply analog output signals for the strip chart recorder terminals, described previously. Finally, system controller 100 controls the serial communications port to the external PC 107, the front panel LED status indicators, the xenon flash lamp trigger control, and the system integrity interlocks.

The software program in system controller 100 has three basic modes which are the power on initialize mode, the command mode and the test mode. In the power on initialize mode, system controller 100 initializes program parameters, initializes hardware in the capillary electrophoresis instrument, sets ASCII communication to "terminal" mode and moves autosampler head 204 to the HOME positions. The communication error LED on the front of the capillary electrophoresis machine is also turned on and a question mark signal sent to external PC 107. After the question mark is sent, the microprocessor waits for a status request from PC 107 and after receiving the status request the communication error LED is turned off and system controller 100 enters the command mode. In the command mode, system controller 100 responds to all commands from PC 107 and after receiving the command sends the signal "OK," back to PC 107. These commands include status, configuration data, test parameters, operational commands and data commands. If the command received is "STARTTEST", system controller 100 transmits the "OK" response and then transfers to the test mode. As described previously, the machine language Forth program for the system controller is given in Appendix A. In Appendix B, the commands to the system controller from the external PC or teletype are defined, and incorporated herein by reference.

In the test mode, the system controller 100 acquires and transmits data to PC 107 per the test parameters which were specified during the command mode. When the test is completed the phrase test complete is sent followed by a 0 for the data and "OK". If an escape character is received during the test or when the test is complete, system controller 100 moves the autosampler head 204 to the HOME position and returns to the command mode.

After the power on cycle described previously, and before the test command is given, external PC 107 is used to configure the EC instrument. When the power is initially applied, no assumptions are made as to hardware coordinate locations. Thus, PC 107 must provide this information sometime prior to transmitting the test parameters for the first test. Once the system is configured, the definitions are retained until changed by PC 107 or until the capillary electrophoresis instrument is turned off. The parameters that must be defined include the locations for the running electrolyte bottles and the test samples, the level sensors for each of the running electrolyte bottles, the running electrolyte supply bottle, the detector electrolyte supply bottle and the waste bottle. The purge controls, described previously, to purge the waste bottle, to purge a selected running electrolyte bottle and the running electrolyte bottle to be refilled using selected supply bottles. The specific commands are given in Appendix B.

After the initial setup the test parameters must next be specified. The test parameters instruct system controller 100 as to which running electrolyte bottle to use, whether the running electrolyte is to be purged and refilled, what aspiration method to use, what the high voltage test conditions are, and other parameters required for the test. Specifically, for each test, the running electrolyte and test sample must be specified and the aspiration method for drawing the test sample into capillary tube 110, i.e., either a vacuum or an applied voltage, must be specified.

After the initialization of the parameters which describe the test, the capillary tube run time power must be defined. There are two modes for controlling the power across the capillary tube during a test. The first mode is a voltage profile mode where a voltage vs. time profile is specified, e.g., the voltage may be changed in a ramp like fashion, and the second mode is a current mode wherein the current values, that must be maintained during the test, are specified. These modes are mutually exclusive. In the voltage profile mode, the applied voltage across the capillary tube is programmed to change as a function of time. The maximum number of profiles settings is limited to 50.

The final parameters that which must be specified are channel numbers of the output data vs. associated detectors. System controller 100 can group the output signals from the sixteen individual diode detectors into any desired combination to form detector groups. A single arithmetic value is reported during the test for each detector group. The grouping consists of adding together individual detector signals. Since fluorescence emmision wavelengths are typically 30 nm FWHH, the signals from two or three diodes can be summed to obtain a better signal to noise ratio. A group can consist from 1-16 detectors and any combination of the 16 detectors can be used to define the group. A maximum of four groups is allowed.

After the parameters for initializing the position of the autosampler head and the parameters for the test are entered, the test command is given and system controller 100 automatically performs the following sequence of operations. After receiving the test command, the status of the sample door is first checked and if the sample door is open an error command is transmitted to PC 107 and system controller 100 returns to the command mode. If the sample door is closed, then the standard response to "OK" is transmitted to PC 107, and the level sensor moved over the running electrolyte bottle specified for the test and lowered into the running electrolyte container. If a prepurge or fill command is given these commands are completed at this time. In the prepurge directive the plumbing is set as required, the vacuum pump is initialized and the vacuum is drawn for a period of time as described previously. After the selected running electrolyte bottle is evacuated, the pump is turned off and the replenishment system is set to exhaust the atmosphere.

The fill directive causes system controller 100 to raise the level sensor to the level defined in the fill directive, set the plumbing to the defined running electrolyte supply bottle and to start the pump for pressure. The pump continues to operate until the level sensor detects liquid and turns off the pump as previously described. After either the refill or purge command, if the level sensor does not detect a liquid level, an error flag is set. If a liquid level is detected, the level sensor is moved to the storage position. Since there is liquid in the running electrolyte bottle, the test is ready to commence and the autosampler head is moved to the running electrolyte bottle that will be used for the test and the capillary tube is lowered into the running electrolyte bottle. The plumbing is then set to draw a vacuum on the running electrolyte bottle and the vacuum pump is turned on. After a selected period of time, as specified in the test parameters, the pump is turned off and the exhaust is set to atmosphere. This operation fills the capillary tube with running electrolyte for the test. Next, autosampler head 204 moves the end of capillary tube 110A to the specified sample and the sample is drawn into the capillary either using the vacuum or the high voltage, as previously described. After the sample is drawn into the capillary tube, the end of the capillary tube is moved to the running electrolyte bottle and lowered into the bottle.

The test is commenced using either the specified voltage or current profile data. After the data is acquired, the high voltage is turned off and an end of data is transferred to PC 107 and the capillary tube is retracted from the running electrolyte. At this time, if a postpurge operation is specified, the running electrolyte is purged as previously described. The capillary tube is moved to the home position and the test is completed. The system controller completes all tests using a specified running electrolyte bottle before proceeding with tests using another running electrolyte bottle.

It will, of course, be understood that modifications of the present inventive automated capillary electrophoresis instrument including the absorbance and fluorescence detector will be apparent to others skilled in the art. For example, the detector can be employed with either column chromatography or tube gel electrophoresis. Consequently, the scope of the present invention should not be limited by the particular embodiments described above, but should be defined only by the claims set forth below and equivalents thereof.

APPENDIX A

CMP/M-701

S1234000601A000058FE000000000000000000000000000000000000000500FFFF6000000C5D
S12340209880398030B03EB012E648FABFD44287428649ED40503E2D402240F578003E2D57
S12340404024 4FF578003C1C3E3568004EF578005C22204C91CD285F3F0854463D063C1C03
S12340603E3568004EF5780099CD3F0C544649F568003C1C3E3568004EF578005446303 5BB
S123408068003C1C3E3568004EF57800544630 3568003C1C3E3568004EF5780000846C6908
S12340A0747100004068484E495449FC4562483A45385192482642 2A008661626F72747185
S12340C04090406849244202003 64F384F3840A4084572726F723A202000410A411800222C
S12340E04EEA51A64D584F1A411800224EEA53BE53BE4D584F1A4F385CF641EA0004490E3D
S1234100422A0084646F747140B940684D584F1A422A836C69744103411A3D1C3C1C3E3549
S123412068004EF5780000846 46C697441124130 2D1C3C1C3E3568004EF57800082646FD7
S12341404127414 4301E321E3F1C343C800094413F02D0423F003C1C3E3568004EF5780030
S1234160833F646F413D4168301E321EB24066D83E1449F578003C1C3E3568004EF578008B
S1234180856C65617665416041 8A584F3E1F49F578003C1C3E3568004EF5780000846C6F16
S12341A06F70418041A65257690CD8043C1C3E3568004EF578005C4F544C3C1C3E3568003E
S12341C04EF57800852B6C6F6F70419041CE301ED15769E2D8043C1C3E3568004EF578006E
S12341E000866272616E636841C441ECD8D43C1C3E3568004EF5780087306272616E6368D6
S123420041E142044A5E660CD8043C1C3E3568004EF57800544C3C1C3E3568004EF57800F0
S1234220008 6756E6E65737441F8422C3E1F49F578003C1C3E3568004EF5780000826F6658
S123424042214244301EB056660E544E544C3C1C3E3568004EF578000D460F28772756E9F
S123426074696D65423D40685 1584A1652544A58422A853B636F6465425C4068483A5158DB
S12342804A1652544A58422A0086444947495 43E42724294301E321E7400044100306B163F
S12342A00C41000A68085F410C41000A6B08B2006C04534230013D0023C1C3E3568004EF51C
S12342C0780000863E44494749544289 42CE301E064000300C40003A68025E403D003C1C68
S12342E03E3568004EF578000086544F47474C4542C342F4301E3E1EB13578003C1C3E35CE
S123430068004EF57800854E554C4C3F42E943103E164A35780066085 44E3E1F49F578008B
S12343203C1C3E3568004EF57800872F535452494E4743064336301EB0566F02301691564A
S12343400 16E00023C1C3E3568004EF5780000845 34B4950432A4358301E321E67203E2DD7
S1234360510A4A757800661 63E1E41F578005341B01856C9FFFC534891CD3D0852413D019C
S12343803C1C3E3568004EF578000084534341 4E434F4394301E321E67143E1E41F57800F6
S12343A0B01857C9FFFC534891CD3D0852413D013C1C3E3568004EF5780042803E0141F5E2
S12343C078001018220002400 03FB019661E5340B30856C8FFFC4A406A1230013208024 12E
S12343E00001D1C1544891CD32084E750240001F0241001F924093C1534901C0320802419C
S123440000 01D1C1321066B24E753C1C3E3568004EF57800008466696E64438441E3E1E49
S123442043F578003E1E67FCBE566604544E60F8320761864A4166163E1E0C47FFFF66E86F
S12344403D3C00003C1C3E3568004EF578000C5EFFFF66FA30013D003C1C3E3568004EF538
S1234460780 04A40671683C06A0C48414A416708D2404841534 14E7548414E7572FF4E750B
S12344808355 4D2A44154488301EC0DE2D003C1C3E3568004EF57800812A4480449E301EFE
S12344A0C1D63C803C1C3E3568004EF5780000842F4D4F44449844B8301E321E48C1610044
S12344C0FFA248412D013C1C3E3568004EF57800812F44AF44D6301E321E48C16100FF844A
S12344E03D013C1C3E3568004EF578000086554D2F4D4F4444D044F8301E660672FF584E34
S12345006004221E82C048412D013C1C3E3568004EF57800854D2F4D4F4444ED451E301E49
S1234520221E6100FF3E48412D013C1C3E3568004EF57800812B4514453A301ED1563C1CA3
S12345403E3568004EF5780081 2D4534454E301E91563C1C3E3568004EF578000082312B06
S1234560454845645 2563C1C3E3568004EF578000082322B455D4578545 63C1C3E35680050
S12345804EF5780000823 12D4571458C53563C1C3E3568004EF5780000823 22D458545A0CE
S12345A055563C1C3E3568004EF5780000823 22A45994 5B4E1D63C1C3E3568004EF5780004
S12345C00082322F45AD45C8E0063C1C3E3568004EF578008344322F45C145DC2016E2806A
S12345E02C803C1C3E3568004EF578000082442B45D445F4201ED1963C1C3E3568004EF5BF

S12346007800854241534528 45ED460C4280301ED08D2D003C1C3E3568004EF578000082C5
S123462044 2D46024626201E91963C1C3E3568004EF5780083533E44461F463C301E48C069
S12346402D003C1C3E3568004EF5780083414E4446344654301EC1563C1C3E3568004EF5F6
S1234660780000824F52464C466A301E81563C1C3E3568004EF5780083584F52466346805B
S1234680301E81563C1C3E3568004EF57800834E4F54467846964A5E57C048803D003C1CA9
S12346A03E3568004EF578008130468E46AEBD4E57C048803D003C1C3E3568004EF57800C5
S12346C0813C46A846C6BD4E5DC048803D003C1C3E3568004EF57800813E46C046DEBD4E10
S12346E05EC048803D003C1C3E3568004EF578000082553C46D846F88D4E55C048803D0011
S12347003C1C3E3568004EF578000082553E46F14712BD4E54C048803D003C1C3E356800AB
S12347204EF578000082303C470B472C4A5E5BC048803D003C1C3E3568004EF578000082CF
S1234740303D472547464A5E57C048803D003C1C3E3568004EF578000082303E473F476020
S12347604A5E5EC048803D003C1C3E3568004EF57800834430 3D4759477A4A9E57C0488020
S12347803D003C1C3E3568004EF578008344303C47724[illegible]A9E5BC048803D003C1C3E3550
S12347A068004EF578000082443D478C47AEBD8E57C048803D003C1C3E3568004EF5780082
S12347C08353504047A747C8200E908D3D003C1C3E3568004EF578008352504047C047E069
S12347E0200F908D3D003C1C3E3568004EF578008353502147D847F83E1E4DF578003C1C2B
S12348003E3568004EF578008352502147F048103E1E4FF578003C1C3E3568004EF5780023
S123482000823E524808482 83F1E3C1C3E3568004EF578000082523E4821483C3D1F3C1CA4
S12348403E3568004EF578000825240483548503D173C1C3E3568004EF5780081494849F8
S123486048623017906F00023D003C1C3E3568004EF57800814A485C487A302F0006906F82
S1234880000 83D003C1C3E3568004EF57800874558454355544548744 89A3C1E3E35680074
S12348A04EF5780087504552464F524D488E48B03E1E3C3578003E3568004EF578000 0846A
S12348C05049434B48A448C83E1EDE473D3678003C1C3E3568004EF578000084524F4C4C9A
S12348E048BF48E44280301ED04041F6080032102248544831215 5406EFA3C813C1C3E3503
S123490068004EF578000084445 24F5048DB4910544E3C1C3E3568004EF5780000845 3577D
S1234920415049074926201648402C803C1C3E3568004EF5780000844F564552491D49401C
S123494 03D2E00023C1C3E3568004EF57800834455504937495 63D163C1C3E3568004EF5A4
S12349607800 00843F44555049 4E496C4A5667023D163C1C3E3568004EF5780083524F5401
S123498049634984201E321E2D003D013C1C3E3568004EF57800008432445550497C49A066
S12349A02D163C1C3E3568004EF5780085325357415049974986201E22162C802D013C1C49
S12349C03E3568004EF57800853244524F5049AC49D2584E3C1C3E3568004EF578008532F6
S12349E04F56455249C849E82D2E00043C1C3E3568004EF578000082434049DE49FE4240F3
S1234A003E16103578003C803C1C3E3568004EF57800814049F74A183E1E08070000660E95
S1234A203D3578003C1C3E3568004EF5780041F5780054881D201D2060EA008243214A120A
S1234A404A423E1E301E1B8078003C1C3E3568004EF5780081214A3B4A5A3E1E08070000E5
S1234A60660E3B9E78003C1C3E3568004EF5780041F578001 0DE10DE60EC00822B214A543D
S1234A804A823E1E301E08070000660ED17578003C1C3E3568004EF5780041F578005488E3
S1234AA01D201D20D15610DE10DE60E400823E3C4A7B4AB43016E1583C803C1C3E35680004
S1234AC04EF578000082324 04AAD4ACC3E1E08070000660E2D3578003C1C3E3568004EF5E7
S1234AE0780041F578005888 1D201D201D201D2060E6008232214AC54AFA3E1E080700000F
S1234B00660E2B9E78003C1C3E3568004EF5780041F578001 0DE10DE10DE10DE60E883437A
S1234B20404C4AF34B264240205E10103D003C1C3E3568004EF578000082404C4B1E4840EA
S1234B40082E00000003660E205E3D103C1C3E3568004EF57800205E54881D201D2060ECCB
S1234B608343214C4B394B68205E301E10803C1C3E3568004EF578000082214C4B604B8018
S1234B80082E00000003660E205E309E3C1C3E3568004EF57800205E10DE10DE60EE0086FC
S1234BA04E45474154454B794BAA44563C1C3E3568004EF5780087444E45474154454B9F93
S1234BC04BC244963C1C3E3568004EF57800873F4E45474154454BB64BDA4A5E6A024456AE
S1234BE03C1C3E3568004EF5780000883F444E45474154454BCE4BF84A5E6A0244963C1C62
S1234C003E3568004EF57800834142534BEB4C104A566A0244563C1C3E3568004EF578007B
S1234C2000844441425 34C084C2A4A566A0244963C1C3E3568004EF57800834D41584C215E
S1234C404C42301EB0566D023C803C1C3E3568004EF57800834D494E4C3A4C5C301EB0566C
S1234C606E023C803C1C3E3568004EF5780081304C544C743D3C00003C1C3E3568004EF516
S1234C80780081314C6E4C883D3C00013C1C3E3568004EF5780081324C824C9C3D3C00020C
S1234CA03C1C3E3568004EF5780081334C964CB03D3C00033C1C3E3568004EF57800008284
S1234CC02D314CAA4CC63D3CFFFF3C1C3E3568004EF578000084464 94C4C4CBF4CDE301ED7
S1234CE0321E3E1E41F578006002 10C051C9FFFC3C1C3E3568004EF578008545524153452C S1234D004CD540684C724CDC422A85424C414E4B4CFA4068516E4CDC422A892D5452414960
S1234D204C494E474D0A4D283016671A3E2E0002DE4041F578000C20002056C8FFFA3C8059
S1234D404A566A0242563C1C3E3568004EF5780085434F554E544D1A4D5A3E164240103586
S1234D60780052473C873D003C1C3E3568004EF5780000004D76301E3E1E41F578004A408B
S1234D806B1210100240001FDE407001C04766105247600C4A106804534860F891CD3E08A0
S1234DA03D073C1C3E3568004EF578008543404F56454D504D86301E671653403E1641F536
S1234DC078003E2E000243F5780010D951C8FFFC584E3C1C3E3568004EF578000086434092
S1234DE04F56453E4DAC4DE84280301E671A3E1641F578003E2E000243F57800D1C0D3C084
S1234E0053401121 51C8FFFC584E3C1C3E3568004EF578008553484946544DD04E1E301E3A
S1234E206D06321EE1696006444 0321EE0693D013C1C3E3568004EF57800008445584954F4
S1234E404E144E443E1F49F578003C1C3E3568004EF5780000824F4E4E3B4E5C3E1E3B8CB4
S1234E60FFFF78003C1C3E3568004EF57800834F46464E554E763E1E3BBC000078003C1CE2
S1234E803E3568004EF57800321E60083E1E41F578002208301E48E70F0F4E424CDFF0F056
S1234EA03D004E75008446444F534E6E4EAE302E000241ED4ED6121880186 70A530166F8BF
S1234EC06100FFCA60046100FFC042663C1C3E3568004EF578000A0204050608090E20250B
S1234EE02E000084454D49544EA540684118000341180 0FE4B24411800044652420 2FFEEEA
S1234F0041180007411800FE4B664C8650F04A80422A00845459504 54EE34068493E45383A
S1234F20492441664F30486049FC4EEA41A4FFF8422A008243524F1340684118000 04EEAAE
S1234F404118000A4EEA50F04E74422A893F5445524D494E414C4F3340684118000341184 1
S1234F6000FE4B244118000146525646422A834B45594F4C40684F584202FFFC41180007D1
S1234F80411800FE4B24422A834259454F6E406840A41342594520495320 4E4F54204445C6
S1234FA046494E454420410A422A008643524541544 54F8840685 16E585A57B24924490EB9
S1234FC04202001E4F3851A64D584F1A40A40E20697320726564656669 6E6564200 0410AC0
S1234FE051A64C86465251B651A6495449FC4118001F4C5A499E49244A40456251925 1B60F
S123500049544118008042F251584A1651C251584A584118408C51C2422A0088434F4E531C
S12350205441 4E544FAB40684FB451C24118407C4266422A00885641524941424C45501B1B
S123504040684FB451A6457651C24C7251C24118408C4266422AC5444F45533E5035406877
S123506059BE427A41184EAD51C2411840525 1C2422A813A5056406854E454624FB4595ADB
S123508041184068426658 6C422AC13B50724068547455665 9BE422A597C483A490E5114B4
S12350A04E74422A00825330508A408C10000082523050A5408C1002853C5449423E50AF4F
S12350C0408C1004008423544942 50B8408C10060082445050C5408C10080088564F432DD0
S12350E04C494E4B50D1408C100A834F555450DB408C100C833E494E50EA408C100E874E98
S12351004F5F534B495050F4408C101085535441544550FE408C10120084424153455 10C38
S1235120408C10148344504C5119408C1016834353505124408C101885484C44512E408C44
S1235140101A00845350414E5138408C101C87434F4E5445585451 43408C101E8557534938
S12351605A45514E407C00020082424C515C407C0020874F524947494E2B5169406851640 5
S1235180449C4118400045384 22A85414C49474E5172406849544C8646524538422A0084DA
S12351A04845524551 8A406850D64A16422A85414C4C4F54519F406850D64A80422A812C80
S12351C051AE40684C9A51B651A6459E4A58422A0082432C51BE40684C8651B651A6458A08
S12351E04A40422A87444543494D414C51D140684118000A51204A58422A8348455851E4F6
S12352004068411800105120 4A58422A853E424F445951FA40684576422A853E4441544112
S1235220520C406845764A16422A85424F44593E521A4068459E422A853E4E414D45522A29
S123524040684CAE454C4CC44D74422A854E414D453E523840684C864D744CAE4538422A4E
S1235260853E4C494E4B524C4068459E422A854C494E4B3E52604068457642 2A00864E3E20
S12352804C494E4B526E40684C864D744562422A00864C3E4E414D45527D4068458A4CC447
S12352A04D74422A00842E435055529140684 0A406363830303020 00410A422A852E4E4197
S12352C04D4552A540684954456249 2449FC4118001F46524F1A538E422A00882E5645520A
S12352E053494F4E528C406841180003411800304 5384EEA4118002E4EEA4118000141 18AF
S1235300003045384EEA4118000041180030453 84EEA422A8350414452DB406851A6411824
S12353200100453842 2A8354494253144068 50C04A16422A0082233E53264068490E490E80
S12353405 13E4A16531A493E454C422A00823C23533540685 31A513E4A58422A0084484F33
S12353604C44534D40684CC4513E4A80513E4A164A40422A008453494 74E535D4068472A85
S12353804202000841180 02D5364422A8123537540685 1204A16568C498242CC5364422A51
S12353A000822353538C40685390499E4668474442 02FFF6422A8553504143 4553A1406835
S12353C0516E4EEA422A00865350414345535 3B640684C724C40496A4202000C531A492449
S12353E0499E4D124F1A422A83442E5253C7406848264954482 64C28535253A6483A537CA9

S1235400533A483A493E454C53D04F1A422A0082442E53E840684C7253EE53BE422A812E67
S1235420540F4068463A5414422A0082552E541E40684C725414422A83552E52542B4068D9
S12354404C72492453EE422A00822E5254384068482646 3A483A53EE422A00842143535092
S12354605449406847C651344A58422A853F434F4D50545B406851144A16474440A4106352
S12354806F6D70696C6174696F6E206F6E6C790040C2422A00863F535441434B546C4068D9
S12354A047C650AA4A16492446F640A40B656D707479207374616 36B40C247C651A6411825
S12354C00180453846F640A40F64696374696F6E6172792066756C6C40C2422A853F4558C3
S12354E045435495406851144A1640A40E657865637574696F6E206F6E6C790040C2422AB4
S123550000863F504149525354DC4068560E40A414696E636F6D706C657465207374727 5F1
S123552063747572650040C2422A00883F44454349 4D414C5501406851204A164118000AEE
S1235540560E40A414424153452060757374206265206465636960616C0040C2422A00841F
S12355603F435350552B406847C651344A16560E40A417646566696E6974696F6E206E6F63
S12355807420666 96E697368656440C2422A008A3F554E444546494E4544555F406840A420
S12355A00C697320756E646566696E65640040C2422A87304449564944 45558F40684CC4B7
S12355C040A41A646976696465206279207A65726F206F72206F766572666C6F770040C2E2
S12355E0422A00863F444550544855B240685672458A492446C440A40B656D707479207393
S1235600746163 6B40C2422A00823C3E55E3406846AC4744422A00823C3D56094068460C8C
S12356204744422A00823E3D5617406846C44744422A83443C3E5625406847AC4744422A0E
S123564083303C3E5632406847444694422A0082443C564040684624479242 2A0082443E25
S1235660564F406849B45654422A854445505448565D406847C650AA4A164924454C45C601
S1235680422A00864D552F4D4F44566A406848264C72484E44F6483A4924482644F6483AE6
S12356A0422A834D4F445683406844B6490E422A852A2F4D4F4456A240684826560A483A5B
S12356C0451C422A00822A2F5680406856884924490E422A00824D2A56C54068499E467EC8
S12356E048264C0E49244C0E4486483A4BF6422A00864558504543545 6D54068514A4E749F
S12357004C724166577C4F74495441180008 46AC42020038490E514A4A164202001E4CC45A
S123572051 4A4A80411800084EEA411800204EEA411800084EEA41EA0008411800074EEA52
S1235740483A459E482641EA003049544118000046AC42020010490E411800204EEA4188FD
S123576041EA001649544EEA493E514A4A1645384A404C86514A4A8041A4FF8C4C724924B4
S1235780514A4A1645384A40422A855155455 25956F14068532C4118005056FA50FA4E7409
S12357A0514A4A1650CC4A58422A008446494E44578A4068495448264CC451584A16483AEC
S12357C0441C4954420200184982490E41180040465242020008 4C8641EA00044CC4422A50
S12357E0000040684826 50CC4A16532C493E50FA4A164334493E4924484E4356493E4924D5
S1235800483A4392490E499E4924454C48264982454C456250FA4A16453849824C5A50FA9E
S12358204A58483A51A65192499E4A40456249244DB451A6519249544D584538516E49241B
S12358404A40422A4068510 84E5A57E251084E74422A0084574F524457AB406857E2422AD6
S1235860008 8434F4D50494C45525853406851144E5A516E585A430E57B2496A420200140B
S1235880472A42020008 51C241EA00044898 41EA00065D5E5DF641EAFFDA422A8B494E5400
S12358A04552505245544552586140685114 4E74516E585A430E57B24202000A4898549E08
S12358C041EA00065D5E5E1C41EAFFE6422A89494E54455250524554589C406851144A163B
S12358E04202000858 6C41EA000458AA422AC15B58CE58F449ED58AC544F3C1C3E35680059
S12359004EF57800C15D58EE590A49ED586E544F3C1C3E3568004EF57800008451554954AD
S12359205904406850FA4E7451144E7450B44A16480E4F385792580A51144A1647444202 3B
S1235940000A40A4026F6B00410A41EAFFE0422A0086534D554447455918406851584A1648
S12359604954 49FC41180020466849244A40422A0088554E534D554447455951406851 58CC
S12359804A16495449FC411800DF465249244A40422A89494D4D45444941544455971406804
S12359A051584A16495449FC4118004046684924 4A40422A87434F4D50494C45599240682B
S12359C0483A4954457648264A1651C2422AC95B434F4D50494C455D59B44068547451 6ED6
S12359E0585A57B24744559C51C2422A0086464F524745545 9CE40685BFC4954524050 0625
S1235A004A5852684A1651584A58422AC12259ED406851144A16420200185 9BE40A44118C9
S1235A20002258444 9FC45625192518641EA001A4118002258444954 49FC456241183DB0A3
S1235A4049244DB441183DB0422A00C22E285A0C406841180029584440584F1A422AC1287B
S1235A605A4B406841180029584 4490E422A00C641424F5254225A5E406854745A1059BEEB
S1235A8040C2422A00C22E225A6F406854745A1059BE410A422A00C2444F5A8540685474 6D
S1235AA059BE414251A64C7251C24CAE422AC33F444F5A97406854745 9BE416651A64C72B1
S1235AC051C24CAE422A00C44C4F4F505AAE406854744CAE550A59BE41A4495445765B24A7
S1235AE051A649244A58422AC52B4C4F4F505AC7406854744CAE550A59BE41CC49544576A0

S1235B005B2451A649244A58422AC54C454156455AE84068547459BE4188422A0084424159
S1235B20434B5B0A406851A6454C51C2422A00C249465B1D4068547459BE420251A64C7276
S1235B4051C24C9A422A00C45448454E5B2F406854744C9A550A51A6493E454C49244A588C
S1235B60422A00C4454C53455B47406854744C9A550A59BE41EA51A64C7251C249244C9A14
S1235B805B4E4C9A422AC5424547494E5B634068547451A64C86422AC5554E54494C5B8647
S1235BA0406854744C86550A59BE42025B24422AC55748494C455B984068547458B3445760F
S1235BC0422AC5414741494E5BB0406854744C86550A59BE41EA5B24422A00C65245504565
S1235BE041545BC24068547448264826SBCA483A483A459E5B4E422A81275BDB4068516E3D
S1235C00585A57B24744559C422AC35B275D5BF84068547458FC5DC6422A0084434F4C44EC
S1235C205C0A40684118402 24A1650AA4A58411840244A1650844A58411840264A1650C0A9
S1235C404A58411840284A1650D64A58411840204A1651584A5851144E7450FA4E74512AA3
S1235C604E7450F04E74514A4E7451084E7451EE5C7C422A854944454E545C1B40684F38C2
S1235C804F3852AC40A406464F5254482000410A52E640A40E2028524F4D207665727369FA
S1235CA06F6E2900410A4F3840A42B436F707972696768742031393834204C61626F7261D9
S1235CC0746F7279204D6963726F737973746560D7320496E632E410A4F384F3840A40652C3
S1235CE0656164792100410A4F385CF6422A8541424F52545C74406850AA4A1647F651EE01
S1235D0051144E745922422A87434F4E564552545CEE406845624954482649FC51204A160F
S1235D2042924202002C492451204A164486490E498251204A16448645F2512A4A1645629D
S1235D40420200084C86512A4A80483A41EAFFC6483A422A874E554D4245523F5D084068E0
S1235D60512A4E5A4C724C7249824954456249FC4118002D46AC4C0E49544826453 85D1263
S1235D80495449FC4118002E46AC42020014495448265D124954483A454C458A512A4A5836
S1235DA0483A42020008 48264BC0483A49FC4954516E46AC492447444668422AC74C4954C1
S1235DC04552414C5D544068547459BE411851C2422A00C8444C49544552414C5D8C4068B1
S1235DE0547459BE412E51C251C2422A874E554D4245522C5DD340684744559C512A4A1614
S1235E004562420200085D0E41EA0006490E5DC6422A872F4E554D4245525DEC406847443E
S1235E20559C512A4A16456247444202000 4490E422A00844455 4D505E12406851204A1682
S1235E40482652004F384F384118000553D0411800104C7241425E6248604CAE544E41A45C
S1235E60FFF84C9A530040A410303132333435363738394142434445460041 0A493E453839
S1235E80492449544118000F4652467E41425EFA4F3848604C724118000453EE53BE486011
S1235EA0411800104538486049 9E41425EC4486049FC53BE4C72535253905390533A4F1AA7
S1235EC041A4FFEC4C9A53D041425EF2486049FC495441180020 46C4493E4118007E460C85
S1235EE0466842020008490E4118002E4EEA41A4FFDC4118001041CCFF984F38483A512047
S1235F004A58422A00822E535E3340685120 4A1648265672496A420200464C724924458AF5
S1235F2041425F5A56724860454C458A48C649544F3851EE41180006544E520040A4022087
S1235F402800410A4C724118000453EE40A40320682941 0A4CC441CCFFCC41EA00104F38E1
S1235F6040A4073C656D7074793E410A4F38483A51204A58422A85574F5244535F05406896
S1235F8051204A16482652004F384F3851584A16495449544C7253525390539053905390 2C
S1235FA0533A4F1A53BE52C450F04A164118003C46DC420200084F3841EA001C50F04A16AF
S1235FC04118001456A8496A4202000C411800144924454C53D052864A16495447444F588A
S1235FE046684202FFAC490E4F384F38483A51204A58422A0086412F444D53425F76407CED
S123600000FF0086412F444C53425FF5407C020087412F4464617461600 3407C0000008606
S1236020412F446075786010407C000187412F446761696E601F407C0002874C414D506DEC
S12360407362602C407C00FF874C414D506C7362603A407C0200874C4D5054524947604888
S1236060407C0001875452494752535460 56407C000000864C4D5053494D6064408C10201F
S123608087444154414 92F4F6073408C102600864D5558492F4F6080408C102C874C414D2F
S12360A050492F4F608F408C103289234348414E4E454C53609C407C001400884C41535448
S12360C04142532360AA407C000D87485643484 14E2360B8407C001387484943484 14E234F
S12360E060CA407C0012852341444453600 8408C103887665245504F525460E6408C103A6F
S1236100008666504153532360F2408C103C0086664348414E236101408C103E0088664CEC
S12361204D50464952456 10F408C10408741435152415445611D408C104287414351434EFB
S12361405452612C408C10448941435150455249 4F44613A408C1046008A414351524154C4
S1236160456D61786148407C00648753554D4441544161594 08C104800882A415645444140
S12361805441616A408C109E008A5245504F5254464 94C456179408C10CA008A5449 4D4562
S12361A0522D494E5452618961AA2D072D082D002D092D012D0B2D034280303C0001307CED
S12361C010FAD0902080307C10F62050101061000460610000246100018861000 2EC261EA8
S12361E0265E221E225E201E205E2E1E4E733C1C3E3568004EF57800327C111830114A40FE

```
S12362006700000B0307C1128045000016A0000A4327C1106225142 11327C110C3091307C58
S123622011022050108061 0000A0307C11204A506700000E307C110E308C00A7600001488
S1236240307C11164A506700000A610000E667000046307C110E3D1030113D003D3C000A4F
S12362603D3C0008367C68E49050307C111E8050673C6A14066E00010004066E00010002FC
S12362800456000 1367C68EE6100063A4E9332960C5E00A66F1C307C11184250307C11206E
S12362A04250327C1106225112BC00086004DCFC0008307C11204A50660C307C111E4A5098
S12362C06704610000204E75307C111A3010307C11183210024100086702 4440307C111008
S12362E001504E754250327C11123D113D11327C11103011915 63D3C003C610005F23D3C3A
S1236300FFC4610005E0303C0052E0D60256FFFE6A04004000083 27C11183280301E915633
S1236320327C1114329E327C1124307C110E30914E75367C11103D13307C1114B748660823
S1236340307C110E30BC00A6367C1112BD4B660E307C110E308C00A7307C111642504E7505
S1236360327C114030114A40670000B0307C115004500001 6A0000A4327C112E2251421115
S1236380327C11343091307C112A2050108061 0000A0307C11484A506700000E307C113656
S12363A030BC00A760000014307C113E4A506700000A610000E667000046307C11363D1098
S12363C030113D003D3C000A3D3C0008367C68E49050307C11468050673C6A14066E0001ED
S12363E00004066E00010002045600013 67C68EE610004D24E9332960C5E00A66F1C307C94
S12364001140425030 7C11484250327C112E225112BC00086004DCFC0008307C11484A50E5
S1236420660C307C11464A50670461000 0204E75307C11423010307C11403210024100080 1
S123644067024440307C11380 1504E754250327C113A3D113D11327C11383011915 63D3C83
S12364600 03C6100048A3D3CFFC4610004783 03C0052E0D60256FFFE6A040040000 8327CA7
S123648011403280301E9156327C113C329E327C114C307C11363091 4E75367C11383D1328
S12364A0307C113CB7486608307C113630BC00A6367C113ABD4B660E307C113630BC00A7EE
S12364C0307C113E42504E75327C116830114A40670000B0307C117804500001 6A0000A4C7
S12364E0327C1156225142 11327C115C3091307C1152205010806 10000A0307C11704A500A
S12365006700000E307C115E308C00A760000014307C11664A506700000A610000E6670004
S1236520004 6307C115E3D1030113D003D3C000A3D3C0008367C68E49050307C116E80504B
S1236540673C6A14066E00010004066E000100020456000 1367C68EE6100036A4E9332964C
S12365600C5E00A66F1C307C11684250307C11704250327C1156225112BC00086004DCFC6C
S123658000 08307C11704A50660C307C116E4A50670461 0000204E75307C116A3010307C2F
S12365A011683210024100086702 4440307C11600 1504E754250327C11623D113D11327CE6
S12365C011603011915 63D3C003C61000 3223D3CFFC461000310303C0052E0D60256FFFE6A
S12365E06A04004000083 27C11683280301E9156327C1164329E327C1174307C115E3091D1
S12366004E75367C11603D13307C1164B7486608307C115E308C00A6367C1162BD4B660E64
S1236620307C115E308C00A7307C116642504E75307C10444A506B0000D00650FFFF662081
S1236640327C10463091307C103C4A506606327C10383091307C103E4A50660430BC0015BD
S1236660307C103E4A50670000A0367C10322653327C10404A51670A425116BC000160003E
S12366800088168C0000367C103E32130C41000C660432BCFFFF4283327C1026225 1361145
S12366A06B66E541327C1048D2C1D791307C103C0C50000166142611429 1327C103886D188
S12366C0327C109EE241D2C132830653FFFF66280650FFFF6632307C103A4A50662A30BC12
S12366E0FFFF307C10A0327C10CC303C001432D80640FFFF66F86010307C102C20503E136D
S1236700367C670A10B378004E750000010203040506070 8090A0B0C0D0E0F101112131482
S12367201516171819 1A1B1C1D1E1F884D55585441424C45619B407C670A8552446D7578AF
S1236740672B40686736453849FC5422422A00844E554C4C673A4068422A0082442A674FA0
S12367604068499E56DA4924490E49544CC446C44202000E49D049D04C72411880004E4230
S1236780475E42020010490E49D04118FFFF41187FFF4E42499E467E48264C0E48264C2879
S12367A0484E449C483A49244826448 64C72483A45F2483A472A420280044BC0422A00828D
S12367C0442F675B40684954474442020006490E4C86493E482648264C28484E4C0E44B67C
S12367E049824982484E4C0E44F64924490E4924483A483A467E472A420200044BC0422AAC
S12368008344 3C3D67BF40685662469442 2A83443E3D68004068565446944 22A0084444D11
S1236820415868 0E406849E649E65654420200044 9B449D0422A0084444D494E681D4068F2
S123684049E649E656624202000449B449D0422A8734234 34E565254683740685352539 01A
S12368605390539053905 33A422A8735234 34E56525468504068535253905390539053907 5
S12368805 33A422A873823434E565254686A4068535253905390539053905390539053903 8
S12368A05390533A422A4A40671683C06A0C48414A416708D240484153414E7548414E7577
S12368C072FF4E753F1E301EC0DE20003D1F301E221E6100FFD248412D012016 48402C80CD
```

```
S12368E0544E4E75301EB05660DC3C804E75301EB0566E023C804E75008854494D45524354
S12369004E546884407C01700088494E5452726174656BF9407C13888741444A54494D450A
S123692069094O7C05FA8754494D4541444A6918407C0000008C492F4F2D54494D45524F14
S12369404646692640BC10F685434C4F434B6935408C10FA00884144A54494D4552694858
S1236960408C10FE872E3174696D657269554O8C11000086323075736563696440684C72CC
S12369804142698A675641A4FFFC422A87323030757365636973406841180 00A697C422A73
S12369A0008635306D736563698C40684118O9C4697C422A873130306D73656369A14068BA
S12369C041181388697C422A85316D73656369B44068411800032697C422A8D494E54522382
S12369E0362D454E41424C4569C869EC46FC25003C1C3E3568004EF578000086405 4494DFE
S1236A004552690A40684118000F411800FE4B244118000D411800FE4B2441180100449C5C
S1236A204538422A00862154494D455269FB4068495441180100 44D441180000411800FE69
S1236A404B664118000F411800FE4B66422A8B5354415254 2D54494D45526A254068411 84E
S1236A60001D411800FE4B24490E422A008A53544F502D54494D45526A4E40684118001F16
S1236A80411800FE4824490E422A008E53544F502D494E5445525255 0546A6D40686A7A38
S1236AA04C7241180008411800FE4B666A7A422A8F53544152542D494E54455252555 05441
S1236AC06A8B40686A9C411800084118000B411800FE4B666A5C69EA422A008A494E4954FF
S1236AE02D54494D45526AB040686A9C4118006041180009411800FE4B666A7A4118001E9E
S1236B0041180019411800FE4B664118001E41180004449C4C72493E463A4B7E411861A853
S1236B2052144924457 6463A4B7E4118001F411800FE69444AF84118000041180000695051
S1236B404AF869046A2E6AC2422A854054494D456ADB40684118000041180000490069 50ED
S1236B604ACA69504ACA49E647AC4202FFF0411800056 7C4422A8B5245534554 2D434C4FCD
S1236B80434B6B4A4068411800004118000069504AF8411800004118000069504AF8422A40
S1236BA000862E317365633F6B76 40686B5241180 06444F64924490E696E4A16493E696EDC
S1236BC04A58560E422A00882E3553656344 6C796BA140684C726BAA4202000445624954FD
S1236BE04118000546DC4202FFEE490E422A00882E6E536563446C796BC740686BAA490E6F
S1236C004C0E6BAA453849544C72561C4202FFF4490E422A008656454C6D61786BEF407CF4
S1236C2003E8008656454C6D696E6C15407C001E008653544F504C6E6C23407C003C854D7A
S1236C40546D696E6C31407C0005854D546D61786C3E407C00A6893E4343574C494D49549F
S1236C606C4A407C005E00883E43574C494D49546C56407C0056873E4343575245466C673B
S1236C80407C005F00863E43575245466C76407C005700885245465350454544 6C85407C22
S1236CA000FF855353434D446C93407C0052834343576CA2407C005A008243576CAE407C4F
S1236CC00052874D4F544F5223316C89407C00FF00864D31444154416CC2407C0001854D37
S1236CE031434D446CD1407C000300884D3153544154555 36CDE407C0003854D31415558A8
S1236D006CEB407C00058 74D315245534554 6CFA40684118008 86D026CCC4B664C86697CD1
S1236D204118000860026CCC4B66422A87404D3144415441 6D0640686CDA6CCC4B24422A57
S1236D4087214D31444154416D2C40686CDA6CCC4B66422A0086214D31434D446D404068C5
S1236D606CE66CCC4B66422A89404D3153544154555 36D5540686CF66CCC4B24422A894D88
S1236D803144575249544 53F6D6840686D744118000646524 7444 22A008A3F4D3153544F27
S1236DA0505045446D7E40686D744118000446524744422A00884D314C494D49543F6D997C
S1236DC040686D74411800044652475E422A00884D313E4C494D49546DB540684C726E1E49
S1236DE04ACA4B666C626D5E6DC04202FFFC6DA64202FFFC4118000 86E1E4ACA4B66422A55
S1236E00008A492F4F2D4D3153544 55060CF408C110289492F4F2D4D315057526E01408CEC
S1236E2011068540314 64C476E12408C110A00884D3150455 2494F446E22408C110C854DE0
S1236E4031534554 6E2F408C110E854D31504F536E3E408C1110008640315 04F53276E4A26
S1236E60408C1112874D3156305 04F536E57408C1114874D314D4F56453F6E64408C1116AC
S1236E800008640315354503F6E72408C11180086 4D3153495A456E81408C111A00884D31B4
S1236EA04343576 66C676E8F408C111C0086 4D31504F533F6E9D408C111E874D3153544F8C
S1236EC0503F6EAD408C112000884D3153545043 4D446EBA408C1122008640315 472756E62
S1236EE06EC9408C1124854D3156454C6ED9408C1126874D3154494D45526EE6408C112843
S1236F000088 4D315245 46504F536EF2407C00000086 4D31546D696E6F01407C0005008629
S1236F204D31546D61786F11407C00A68B2B4D31504F534C494D49546F1F407C3A988B2DDA
S1236F404D31504F534C494D49546F2C407CC5688B494E49542D4D3144415441 6F3E4068E1
S1236F606D8A4202FFFC411800C86D4A6D8A4202FFFC4118003260 4A411800C849546D8AD2
S1236F804202FFFC6D4A41180100 44D46D8A4202FFFC6D4A69AA6CE66CCC6E0E4AF86D02CE
S1236FA06CCC6E1E4AF84C726E8A4A586F2849546E3A4A5845626E464A586F1A6EE24A5879
S1236FC04C726E7C4A584C726EC44A584C726EB64A58422A00905354415254 2D4D3146557D
```

```
S1236FE04C4C535445506F5040686D1069966D8A4202FFFC4C9A6D5E6F5E4C9A6E984A5894
S12370006EE24A1645B26EE24A586E524A164118FFFE46526E524A58422A0090535441522D
S12370205420D4D3148414C46535445506FD5406860106996608A4202FFFC411800066D5E2E
S12370406F5E4C866E984A58422A00864D3153544550701B40686EA84A1642020008 6CB424
S123706041EA00046CBE6D8A4202FFFC6D5E422A0086214D3156454C704B4068496A474499
S12370804202000A4CC46EC44A584E424C726EB64A584C726E7C4A586E8A4A16475E42021B
S12370A000204954472A6E8A4A166CB446AC467E420200084CC441EA00044C726EC44A5853
S12370C04954472A420200086F4C41EA00046F3A49546E6E4A586E604A584C0E69144924F0
S12370E044D46F1A4C406E984A16449C49546EE24A586E464A584CC46E7C4A584CC46EB664
S12371004A58422A85504F534D31707140686F4C4C406F3A4C5A6E984A164BA84652495 4BB
S12371206E604A166E984A164BA8465246AC42020006490E4E424C726EB64A5849546E601A
S12371404A586E8A4A16475E420200426E524A16454C496A420200324954482647 2A6E8A88
S12371604A164118000846524 75E467E483A4C0E6C3A45B246C4466842020008 4CC441EA91
S123718000044C726EC44A5841EA0004490E6EE24A166E464A584CC46E7C4A584CC46EB6F9
S12371A04A58422A8B214D31504F5373706565647104406 86C1E4C5A6E984A164C864C407F
S12371C04C9A4C5A44D46914492444D449546E464A586EE24A58422A874D4F544F52233247
S12371E071A4407C00FF00864D3244415441 71D8407C0009854D32434D4471E7407C000B97
S123720000884D32535441545553 71F4407C000B854D324155587201407C000D874D3252CD
S12372204553455472104068411800887218 71E24B664C86697C411800087218 71E24B66DA
S1237240422A87404D32444154417 21C40687 1F071E24B24422A87214D32444154417242A4
S1237260406871F071E24B66422A0086214D32434D4472564068 71FC71E24B66422A894081
S12372804D325354415455537 26B40687 20C71E24B24422A894D32445752495 4453F727E50
S12372A04068728A41180006465247444 22A008A3F4D3253544F5050454472944068728A27
S12372C04118000446524744422A00884D324C494D49543F72AF4068728A4118000446523F
S12372E0475E422A00884D323E4C494D495472CB40684C7273344ACA4B666C62727472D6AA
S12373004202FFFC72BC4202FFFC411800087 3344ACA4B66422A008A492F4F2D4D325354E0
S1237320455072E5408C112A89492F4F2D4D3250575273 17408C112E854D32464C47732854
S1237340408C113200884D32504552494F447338408C1134854D3253455473 45408C1136D9
S12373608 54D32504F537354408C113800864D32504F5327 7360408C113A874D3256305053
S12373804F53736D408C113C874D324D4F56453F737A408C113E00864D325354503F738894
S12373A0408C114000864D3253495A457397408C114200884D324343 57666C6773A5408C42
S12373C01144008 64D32504F533F73B3408C1146874D3253544F503F73C3408C1148008867
S12373E04D325354504 34D4473D0408C114A00864D325472756E73DF408C114C854D325652
S1237400454C73EF408C114E874D3254494D455273FC408C115000884D32524546504F5351
S12374207408407C000000864D32546D696E7417407C0005008 64D32546D617874 27407C31
S123744000A68B2B4D32504F534C494D4954 7435407C3A988B2D4D32504F534C494D4954FD
S12374607442407CC5688B494E49542D4D32444154417454406872A04202FFFC411800C802
S1237480726072A04202FFFC41180032726041180 0C8495472A04202FFFC726041180 1002D
S12374A044D472A04202FFFC726069AA71FC71E273244AF8721871E273344AF84C7273A04A
S12374C04A58743E495473504A584562735C4A58743073F84A584C7273924A584C7273DA19
S12374E04A584C7273CC4A58422A00905354415254 2D4D3246554C4C535445507466406820
S12375007226699672A04202FFFC4C9A7274747 44C9A73AE4A5873F84A1645B273F84A5853
S12375207 3684A164118FFFE465273684A58422A009053544152542D4D3248414C465354A9
S1237540455074EB40687226699672A04202FFFC4118000672747474 4C8673AE4A58422A75
S12375600086 4D3253544550753140 6873BE4A164202000 86C8441EA00046CBE72A04202CC
S1237580FFFC7274422A0086214D3256454C75614068496A47444202000A4CC473DA4A5884
S12375A04E424C7273CC4A584C7273924A5873A04A16475E420200204954472A73A04A1636
S12375C06CB446AC467E420200084CC441EA00044C7273DA4A584954472A42020008746269
S12375E041EA0004745049547384 4A5873764A584C0E691449244 4D474304C4073AE4A16C6
S1237600449C495473F84A58735C4A584CC473924A584CC473CC4A58422A85504F534D3261
S12376207587406873AE4A164BA8465274624C4074504C5A4954737 64A1673AE4A164BA870
S1237640465246AC42020006490E4E424C7273CC4A58495473764A5873A04A16475E420248
S12376600042736 84A16454C496A42020032495448264 72A73A04A164118000846524 75E42
S1237680467E483A4C0E6C3A45B246C44668420200084CC441EA00044C7273DA4A5841EA8E
S12376A00004490E73F84A16735C4A584CC473924A584CC473CC4A58422A8B214D32504F51
S12376C053737065656476 1A40686C1E4C5A73AE4A164C864C404C9A4C5A44D46914492460
```

```
S12376E044D44954735C4A5873F84A58422A874D4F544F52233376BA407C00FF00864D3388
S123770044415441 76EE407C0101854D33434D4476FD407C010300884D335354415455533 1
S1237720770A407C01038540334155587717407C0105874D3352455345547726406841 1899
S12377400088772E76F84B664C86697C41180008772E76F84B66422A87404D334441544130
S123776077324068770676F84B24422A87214D33444154417758406877067 6F84B66422A2D
S12377800086214D33434D44776C4068771276F84B66422A89404D335354415455537 78126
S12377A04068772276F84B24422A894D33445752495444 53F7794406877A04118000646 5263
S12377C04744422A008A3F4D3353544F5050454477AA406877A041180004465247 44422A7A
S12377E000884D334C494D49543F77C5406877A04118000446 52475E422A00884D333E4C2C
S1237800494D495477E140684C72786C4ACA4B666C62778A77EC4202FFFC411801006BAAEA
S12378204538495447 2A42020006490E816277D24202FFEC490E41180008786C4ACA4B665C
S12378404C72495478A04A5878AE4A58422A008A492F4F2D4D335354455077FB408C115200
S123786089492F4F2D4D33505752784F408C1156854D33464C477860408C115A00884D331F
S123788050455249 4F447870408C115C854D335345547870408C115E854D33504F53788CE4
S12378A0408C116000864D33504F532778 98408C1162874D335630504F5378A5408C11643C
S12378C0874D334D4F56453F7882408C116600864D335354503F78C0408C116800864D33FB
S12378E053495A4578CF408C116A00884D33434357666C67780D408C116C00864D33504F5A
S1237900533F78EB408C116E874D3353544F503F78FB408C117000884D3353545043 4D4404
S12379207908408C117200864D335472756E7917408C1174854D3356454C7927408C117604
S12379408 74D3354494D4552793 4408C117800884D3352454 6504F537940407C00000088C5
S1237960 4D3356454C6D6178794F407C00FA00864D33546D696E795F407C001400864D338C
S12379805 46D6178796F407C00A6882B4D33504F534C494D4954797D407C3A988 2D4D339C
S12379A0504F534C494D4954798A407CC5688B494E49542D4D3344415441 799C406877B6F6
S12379C04202FFFC411800C8777677B64202FFFC411800647776411800C8495477B6420211
S12379E0FFFC777641180100 44D477B64202FFFC777669AA771276F8785C4AF8772E76F89D
S1237A00786C4AF84C7278D84A587986495478884A58456278944A58797879304A584C72FF
S1237A2078CA4A584C7279124A584C7279044A58422A00905354415254 2D4D3346554C4C2C
S1237A40535445507 9AE4068773C699677B64202FFFC4C9A778A79BC4C9A78E64A5879304E
S1237A604A1645B279304A5878A04A164118FFFE465278A04A58422A0090535441525 42D89
S1237A804D3348414C4653544550 7A334068773C699677B64202FFFC41180006778A79BC03
S1237AA04C8678E64A58422A00864D3353544550 7A79406878F64A16420200086CB441EA42
S1237AC000046C8E77B64202FFFC778A422A0086214D3356454C7AA94068496A4744420240
S1237AE0000A4CC479124A584E424C7279044A584C7278CA4A5878D84A16475E4202002073
S1237B004954472A78D84A166CB446AC467E420200084CC441EA00044C7279124A584954BA
S1237B20472A4202000879AA41EA00047998495478BC4A5878AE4A584C0E6914492444D48A
S1237B4079784C4078E64A16449C495479304A5878944A584CC478CA4A584CC479044A584D
S1237B60422A85504F534D337ACF406878E64A164BA8465279AA4C4079984C5A495478AE3B
S1237B804A1678E64A164BA8465246AC42020006490E4E424C7279044A58495478AE4A58D3
S1237BA078D84A16475E4202004278A04A16454C496A420200324954482 6472A78D84A1688
S1237BC04118000846524 75E467E483A4C0E6C3A45B246C44668420200084CC441EA000483
S1237BE04C7279124A5841EA0004490E79304A1678944A584CC478CA4A584CC479044A5836

S1237C00422A88214D33504F5373706565647B6240686C1E4C5A78E64A164C864C404C9A0E
S1237C204C5A44D4691449 2444D4495478944A5879304A58422A88494E49542D4D4F544F53
S1237C4052537C024068702E4C7249546E524A586E604A5875444C72495473684A58737610
S1237C604A587A8C4C72495478A04A5878AE4A58422A0088414C4C2D484F4D457C364068FE
S1237C80828A4694420200048 3244C726E1E4ACA4B664C7273344ACA4B664C72786C4ACA1C
S1237CA04B6678066C62605E6C6272746 0C072D646524202FFF84118006468AA4538495410
S1237CC0472A42020006490E81B06DA672BC46524202FFE8490E7C446F0C74227E4C41180E
S1237CE000086E1E4ACA4B664118000873344ACA4B6641180008786C4ACA4B66422A85540B
S1237D0053544 4D317C7340684954710C6BAA42020014495 46E524A1649544F38542246ACD3
S1237D2041EA00044C724F584202000E4F744118001B46AC41EA00044C7246684202FFCE84
S1237D40490E422A85545354 4D327CFE4068495476226BAA420200144954 73684A16495424
S1237D604F38542246AC41EA00044C724F584202000E4F744118001B46AC41EA00044C7214
S1237D8046684202FFCE490E422A855453544 4D337D44406849547B6A6BAA420200144 95468
S1237DA078A04A1649544F38542246AC41EA00044C724F584202000E4F744118001B46ACAC
S1237DC041EA00044C7246684202FFCE490E422A8558484F4D457D8A407C00008559484FF2
```

```
S1237DE04D457DD0407C0000855A484F4D457DDC407C00000088583E4C495144455470E881
S1237E00407CFD580088593E4C49514445547DF5407CFE9300885A3E4C49514445547E0546
S1237E20407CFFB08958593E4C49514445547E154068490E48267E004838483A7E10453810
S1237E407E4C422A85504F5358597E244068780649 9E7622710C6E524A1673684A1649E672
S1237E6047AC4202FFF249D0422A0086504F5358595A7E44406848267E4C483A49547B6A28
S1237E8078A04A16493E46AC4202FFF6490E422A0084504F53587E6B4068710C422A008425
S1237EA0504F53597E9140687622422A0084504F535A7E9F40687B6A422A893F5873746F5C
S1237EC0707065647EAD40686E8A4A164744422A893F5973746F707065647EBA406873A0C0
S1237EE04A164744422A893F5A73746F707065647ED0406878D84A164744422A883F5859EE
S1237F005A73746F707065647EE640687EC67EDC46527EF24652422A874F534354494D45B3
S1237F207EFC408C117A00884F534353504545447F18408C117C874F5343776169747F27D7
S1237F4040687F224A164C724C4068AA42020004458A4954472A4F5846684202FFEE490E13
S1237F60422A008843484B53504545447F3640687F324A164118FC184C40411803E84C5A71
S1237F807F324A58422A8743484B54494D457F6340687F224A164118FF384C40411800C8CA
S1237FA04C5A7F224A58422A875445535458595A7F86406897CE7C7E411807D0411807D02A
S1237FC0411801F47E747DD87DE4411801F47E744F584202000E4F744118001B46AC41EA1A
S1237FE000044C724202FFD2422A0086224552524F527FA840684118000086E1E4ACA4B6687
S12380004118000873344ACA4B6641180008786C4ACA4B6640A408203C4552524F523E0075
S1238020410A5922422A00865354415455537FEB408C117E875445524D666C678027408C70
S123804011808954455240606F64653F80344068803E4A165646422A87535441545553 3FBA
S1238060804240685120 4A16520080304A16543051204A58422A89445241574552657272C5
S12380808058406841188001803 04A16466880304A58804E420200264F3840A41C284452F5
S12380A041574552204F50454E2E2054455354204 1424F525445442129004 10A7FF4422A18
S12380C087524565727 26F728076406841188002803 04A16466880304A58804E4202002099
S12380E04F3840A416284E4F2052452E205445535420 41424F525445442129004 10A7FF4C8
S1238100422A008A524554524143546572 7280C0406841188004803 04A16466880304A5832
S12381208 04E4202002E4F3840A4252853454E534F522052455452414354204552524F528A
S12381402E2054455354204 1424F5254454421294 10A7FF4422A00885A4158495365727298
S12381608103406841188008803 04A16466880304A58804E4202002E4F3840A425285A206C
S12381804158495320524554524143542045 52524F522E2054455354204 1424F5254454418
S12381A02129410A7FF4422A855B59657272815740684118801080304A16466880304A584F
S12381C0804E4202002C4F3840A4222858206F722059204158495320 4552524F522E205435
S12381E045535420414 24F525445442129004 10A7FF4422A894C4951444554647 76E81A83C
S1238200407C2000008E4C4951534F4C494E4F494470777281F4407C40008B53454E534FCC
S1238220526C656E7468820540 7C001E8D4C4556454C53454E5345492F4F821A408C118227
S12382408548566D6178822C407C7530008848565345 54492F4F8240408C118889492F4F52
S1238260535441545553824D408C118A8B50414E454C5354415455 53825C408C118C893FF2
S123828053454E534F527570826C40684118030 0411800FF4B3E4C9A465247448 04E42022D
S12382A0001640A40A3F53454E534F5275702000410A49545422422A8D455854454E442D4C
S12382C053454E534F52827E4068804E4202001640A40E455854454E442D53454E534F522F
S12382E020004 10A82684A1682004668821646684954411803004 11800FF487E6BD2821660
S12383004CC4467E4652411803004 11800FF4B7E422A008E52455452414354 2D53454E53FB
S1238320 4F5282B84068828A420200044E424C7282684A1682004CC4467E46528216466896
S12383404954411803004 11800FF4B7E4C866BFA82164CC4467E4652411803004 11800FF10
S12383604B7E6BD2456249544CAE46DC42020006490E8110828A4202FFB8490E422A873FD1
S12383804C4951554944831340684CC4804E4202001440A4083F4C4951554944200041 0A3F
S12383A04954542242 2A0086505540506F6E837E4068804E4202000E40A407505540506F30
S12383C06E20410A422A87505540506F666683A74068804E4202001040A408505540506FBF
S12383E06666200041 0A422A8756454E542D444583C64068804E4202001040A40856454E74
S12384005420444520004 10A422A008E415350522D56414355554D2D4F4E83E8406840A4F4
S12384200F415350522D564143555 54D2D4F4E20410A422A8D415350522D564F4C54532D9F
S12384404F4E840B406840A40E415350522D564F4C54532D4F4E2000410A422A8F41535043
S1238460522D5641435555 4D2D4F4646843440684 0A4104 15350522D564143555540 2D4F9C
S1238480464620004 10A422A008E415350522D564F4C54532D4F4646845C406840A40F4128
S12384A05350522D564F4C54532D4F464620410A422A008E434845434B2D415350522D5350
S12384C04554848940 68422A8D4452415745 52636C6F7365643F84B3406841180300 41183F
```

S12384E000FF4B3E4C8646524744422A884452415745526F70656E3F84C84068840847447З
S1238500422A008621485653455484EC40684C724C4082484C5A4118409582485 6CA8258F6
S12385204A58422A884F50454E2D445241574552850340687C7E82684A1649544118800090
S1238540466841180300411800FF4B7E68D2411880004CC4467E4652495482684A584118E8
S1238560030041 1800FF4B7E422A008A494E49542D50414E454C852440684118120149 54B2
S12385804118030241 1800FF4B7E827A4A58422A008852554E4C45446F6E85684068827A8B
S12385A04A16411804004668495482 7A4A584118030241 1800FF4B7E422A8952554E4C4517
S12385C0446F666685914068827A4A16411804004CC4467E46524954827A4A584118030 29C
S12385E0411800FF4B7E422A8853414D504C454C45446F6E85BA4068827A4A164118080047
S123860046684954827A4A5841180302411800FF4B7E422A008C53414D504C454C45446FF0
S1238620666685E84068827A4A1641180800 4CC4467E46524954827A4A584118030241183A
S123864000FF4B7E422A8953484F57754140505386154068827A4A16411803FF4CC4467EA4
S12386604652411 8003F46684954827A4A5841180302411800FF4B7E422A00842E52455653
S1238680864640684 0A413285265762034 2F32312F38382031313A333029410A422A855489
S12386A0524143458 67B408C118E892E31736563434E5452869E408C1190872E6E44454C4C
S12386C0415986AA408C11920086662E3153454386BA408C11948850524F46494C45706E0C
S12386E0747286C9408C11960088485674617267657486D6408C11980086485653455 43010
S123870086E9408C119E894556454E547469 6D6586F9408C11A4008648566 46C7461870 65B
S12387204 08C11AA008848566 46C74612B2D87 17408C11B000886652456 56D707479872500
S1238740408C11B287665245666 96C6C8735408C11B48747524F555023318744408C11B648
S123876087475 24F5550233287524 08C11C98747524F555023338760408C11DC8747524F94
S1238780555023348 76E408C11EF8747524F55502335877C408C12028747524F555023365C
S12387A0878A408C1215008C494E49542D444154414 1435187984068 4CC461444A584C72F9
S12387C0610A4A584C7261184A584C7260FC4A58411 8000A60EE4A58616661364A584C72E2
S12387E061284A58607C4C7260A64AF8606E60A64ACA4B66600C601A45385FFE608A4AF8E3
S1238800600C602845385FFE60984AF8617460B6411 80004449C453861744142882A4C72DF
S12388204860 4A584C9A41CCFFF6422A8D53544152542D444154414 1435187A740684CC479
S12388406 1444A5860B661184A5860EE4A164C864C40610A4A58617460B641180004449C5B
S1238860453861744142887 44C7248604A584C9A41CCFFF661364A1661664C5A4C864C4071
S1238880691449244 4D449546 1544A5861444A58422A008C53544F502D444154414 143513D
S12388A0882C40684CC461444A58422A8B5453542D44415441414351889340688 7B64C8621
S12388C04C40495460EE4A586B84883C610A4A1647444202FFF888A26B525414422A008AF2
S12388E0534156452D47524F555088AC4068493E47444202000C4CC449244A40490E4E425F
S1238900493E482647C650AA4A16483A457645B2454C560E4202002450AA4A1647F640A4EB
S12389201544455445 43544F5220434F554E54204552524F5220410A4E424924493E453805
S123894049244142898C41180010493E46C4493E4C8646C44668420200244 0A410444554CA
S12389604543544F5223204552524F522000410A50AA4A1647F6418841EA000E48604A4073
S12389804CC44860456 24A4041A4FFBC422A8947524F5550236164728 8DF408C1228008A77
S12389A03F4156452D47524F5550898E4068482 6484E4C8646AC42020004875C484E4C9AB0
S12389C046AC42020004876A484E4CAE46AC420200048778484E4118000446AC4202000472
S12389E08786484E4118000546AC42020004879448 4E4118000646AC4202000487A2483A43
S1238A00490E899A4A584118000041 18000041 1800114C7241428A62899A4A164860453845
S1238A2049FC49544118001046DC4202001C490E4860496A4202000A67C44CC441EA0004FB
S1238A40490E418841EA001845B2619645384A164C724C4041180FFF4C5A463A45F241A4F1
S1238A60FFB8422A00905245504F52542D47524F5550444154418 99F40684C8689AC420274
S1238A800008685A4F1A53BE4C9A89AC42020008685A4F1A53BE4CAE89AC42020008685AAE
S1238AA04F1A53BE4118000489AC42020008685A4F1A53BE4118000589AC42020008685A7D
S1238AC04F1A53BE4118000689AC42020008685A4F1A53BE422A008E5245504F52542D48B1
S1238AE056766F6C74738A65406882584A1682484 1180FFF56CA4C725352539053905390B6
S1238B0053905390533A4F1A53BE422A8D5245504F52542D48566 16D70738AD74068619633
S1238B2060E245B245384A164C72685A4F1A53BE422A8B5245504F52542D54494D45880C5B
S1238B40406868524118006467C4688E4F1A53BE422A915245504F52542D444154415341A0
S1238B604D504C458832406841 18003A4EEA88408A788AE8881C4F38422A83545323885290
S1238B80408C122A83524523887A408C1232008646494C7365748B84408C123A0088415387
S1238BA050455241544588 8F408C124200864845594255468890408C124A85564F4C5453FD

S12388C08BAD407C0001008656414355554D8BBA407C000000885428707269 6D652988C7A8
S12388E0408C127400864445454678797A8BD540684FB451C251C251C2411800065186427AF9
S1238C004EAD4052482 6484E4118000445384A16484E45764A16483A4A16422A833D54531F
S1238C208BE540688880482 6484E4A58484E45764A58483A41180004453 84A58422A833D4A
S1238C4052458C1C4068888A4826484E4A58484E45764A58483A4118000445384A58422A11
S1238C60008830464 94C4C2D52458C3E40688B984826484E4A58484E45764A58483A411837
S1238C80000445384A584CC4874E4A58422A893D5428707269 6D65298C6140688BE04A5890
S1238CA0422A893D454D5054592D52458C8E40684CC487404A58422A00863D47524F555034
S1238CC08CA2406849544C8646AC4202000A490E875C88EC4E4249544C9A46AC4202000A0A
S1238CE0490E876A88EC4E4249544CAE46AC4202000A490E877888EC4E42495441180004F9
S1238D0046AC4202000A490E878688EC4E424954411800054 6AC4202000A490E879488EC86
S1238D204E4249544118000646AC4202000A490E87A288EC4E42490E40A40047524F55500A
S1238D40232045525 24F5220410A50AA4A1647F6422A883D53414D504C45524154458CB9D9
S1238D6040686166 4C5A4C864C40495461364A586914492444D461544A58422A893D415387
S1238D8050455241544 58D5240688BA84826484E4A58484E45764A58483A4118000445385F
S1238DA04A58422A0086405245 78797A8D7C40688B8A4826484E4118000445384A16484E3F
S1238DC045764A16483A4A16422A00864054537879 7A8DA540688B804826484E4118000408
S1238DE045384A16484E45764A16483A4A16422A00885650524F46494C458DCB408C1276F8
S1238E0085565063 6E748DF1408C12DC835856508E00408C12DE893D5650524F46494C45AE
S1238E208E0C40684C728E084A584C728E124A5840A4026F6B00410A4F388B649544 1182D
S1238E40000B453849244 1428E564118002048604A4041A4FFF68BB645624118000A56FA92
S1238E608BB6495441 18000A453849244 1428E8A486049FC4118002046C44202000A411811
S1238E80002048604A4041A4FFE88B6495441 18000A4538492441428EF84860456249FCE8
S1238EA049544118002C46DC4924411 8003A46C44652486049FC4118002046AC4652420294
S1238EC00034486 05D5E47444202000 84C7241EA0004490E49548DFC8E084A1645384A58A1
S1238EE04C9A8E084A80472A4202000A4CC48E124A58418841A4FFA48E124A16472A420211
S1238F00FF30422A00885245444 54678797A8E164068411840224A1650AA4A584118402499
S1238F204A1650B44A58411840264A1650C04A58411840284A1650D64A58411840204A1654
S1238F4051584A5851144E7450FA4E74512A4E7450F04E74514A4E7451084E7451EE40A4B5
S1238F60026F6B00410A5CF6422A88584D49542D5245504F52548F05406860FC4A16949016
S1238F804A1646524202000A8B664C7260FC4A58422A87474F544F7879488F6A4068828AC8
S1238FA046944202000483247 8AE4A167DF0560E4202000A7DF07EB441EA001A7EF24202A7
S1238FC00014499E7EA67E987F0A420200084C86949E4A8049D0422A85474F544F7A8F92D7
S1238FE04068828A469442020004832478AE4A16493E560E420200087EB441EA0010490E6F
S12390007EF2420200084C86949E4A80422A915345542D534F555243452D46494C544552E8
S12390208FD840684C86949E4A80422A008A46494C544552776169749 00E40684C86949E94
S12390404A80422A89474F544F5245787948902D4068828A4694420200048324 8DAE490E78
S12390608F9C422A009053455 42D4C4556454C2D53454E534F5290444068 8DAE482648269A
S12390807E004538483A7E104538483A7E2045387E7482C84C7286B64A584118000586C427
S12390A04A584C86949E4A80422A008A53454E534F5277616974906540688 6B64A1686C434
S12390C04A16562A420200084C86949E4A80422A893F454D5054592D524590AB4068874061
S12390E04A164202001E4F3840A40B454D505459494E47205245410A4C7287404A5841EA73
S1239100002A4F3840A41B454D50545920434F4D504C455445204F522042595041535345 9B
S123912044204 10A4C86949E4A80422A00883F46494C4C2D524590D04068874E4A1642020F
S1239140001E4F3840A40A46494C4C494E47205245 00410A4C72874E4A5841EA002A4F3860
S123916040A41A46494C4C20434F4D504C455445204F5220425950415353454420 00410AA6
S12391804C86949E4A80422A0088434845434B2D5245912D40688388420200148 3244C86A5
S12391A0949E4A804C7286B64A5841EA000480CA422A89474F544F524578797A91894068A8
S12391C0828A4694420200048324 8DAE7E744C86949E4A80422A009253455 42D4341504987
S12391E04C4152592D5052494D4591B2406883B04C7286B64A584C86949E4A80422A008E07
S1239200505249 4D452D4341 50494C41525991D7406886B64A168BE04A1646DC4202000C62
S123922083D083F24C86949E4A80422A89474F544F5453787948 91FF40688DD4490E8F9C6B
S1239240422A87474F544F54537A922C40688DD44826490E490E483A8FE0422A008C534559
S1239260542D41535045524154459 24240688BA84A168BD046AC42020008841C41EA00049D
S123928084444C7286B64A584C86949E4A80422A88444F2D4153504552415445925D4068F5
S12392A086B64A168BA845764A16562A4202002088A84A168BD046AC42020008846E41EA93

```
S12392C00004849A4C86949E4A8041EA000484C4422A008C535441525470726F66696C65AC
S12392E0929040684C7286E44A584118000004118000086F44AF84C7286864A584118000073
S123930041180000871244AF84118000041180000087204AF84C7287304A5841180000411881
S1239320000087024AF84C72850C6884883C4C8694904A584C86949E4A80422A8D4E455812
S12393405 42D50524F46494C453F92D3406886F44ACA87024AF886E44A1680FC4538495465
S1239360 4A164954472A4202000849D04C724E42463A86F44AF84576 4A1687124A584118 0D
S1239380000486E44A8086F44ACA87024ACA4624495487304A5887124A16496A4202000412
S12393A067C487204AF887124A16463A411803E867606B5245F287124AF887024ACA41184C
S12393C0000A676087024AF84C7286864A584CC4422A008A444F2D50524F46494C45933CAB
S12393E040686B5287124ACA681442020020934C47444202001494FC949E4A5888A240A443
S12394000528454E4429410A41EA004A86024A1686864A16495486D24A5846AC4202000436
S12394204E4287204ACA86864A164562676087024ACA45F24118000A67C486F44ACA87302C
S12394404A16472A4202000868244 1EA0004683E490E850C422A87474F544F48484893D338
S123946040684C72850C7DD87DE48F9C422A0088454E4442D54455354945640687C7E4C728E
S12394 80949E4A58422A8754455354666C67946F408C12E00086544553545 0439486408C88
S12394A012E2834E554C9495406840A40D4558454355544520 4E554C2020410A4C86949ECF
S12394C04A80422A94A89022903A94A8907890B8900C913890B8919491BE92109238924CD3
S12394E0926C929E905091BE92E293E094A8947A008853544F505445535494A2407C0014C6
S12395008B5445535450524F4752414C94F1407C94C4008841424F5254666C679500408C31
S123952012E4008A434845 434B2D54455354 95134068949E4A1649544411800 1246AC4202BC
S123954 00000685F68652495494FC46AC42020004862449544 5B2950E45384A164898949E77
S12395604A164826484E46AC483A4744466 84954469486A64A164C72560E4652420 20034A1
S1239580949E4A16495440A4045850433D00410A542245B2950E45384A1652404954456277
S123 95A0492449FC4118001F46524F1A40A4015D410A4202FF7E422A008A53544152542D7D
S12395C054455354 49523406884FA4202000680824E42859C40A4026F6B00410A4F387C7EE0
S12395E04C86949E4A584C72951E4A5884FA4202000680824E426BAA4202000A8F784C8618
S123960086B64A809530949E4A164 95444118001246AC4202000685F686524118001346DCC4
S12396204202 0004862447C650AA4A16560E4202004647C650AA4A1646C44202001440A432
S1239640084449525 45920535441434B410A5F0A47C650AA4A1646DC4202001640A40F53FC
S1239660 5441434B820554E444552464C4F57410A50AA4A1647F64F58495442020032490EFA
S12396804F7441180 01B46AC49544202002240A4072841424F5254942 94904A5817
S12396A04C72949E4A584C86951E4A587C7E949E4A16474446684202FF348578422A0090B8
S12396C0494E49542D54455354 42D50415241 4D5395B940684CC48DFC4A584C864C864C864D
S12396E08CC24C9A4C864C9A8CC24CAE4C864CAE8CC2411800044C86411800048CC24C9A58
S12397004C864C9A8CC24C72411800058CC24C72411800068CC27DD87DE47DF08C227DD844
S12397207DE47DF08C44411800328C9A4C7287404A584C72874E4A58422A8D215445535420
S12397402D50524F46494C45966F40684C728DFC4A584C728DFC4C9A45384A584118 03E851
S123 97608DFC411800 0445384A58411800 1E8DFC411800 0645384A584CC48DFC411800 0868
S1239780 45384A58422A008C21544553542D5041524 14D53973A406841180C1C4C7241184B
S12397A003848C22411803B64118 0361411803848C44411800C8411800 648D08088422A37
S12397C08B494E49542D53595354454D 978740 686A9C7C4487B66AE896024C7280304A5821
S12397E04C7286A64A584C72803E4A584C7282684A58974A979685788682422A8354535474
S123980097C040684F3850FA4A16542250CC4A1654224F384 1180020 50FA4A16532C453806
S12398204404118005050FA4A1645624142986E4F584202FFFC4F7441180020532C4860CE
S12398404562 4538 4A4 04954411800 0D46AC4202000E490E4860456250CC4A584188495445
S12398 60532C486045384A404EEA41A4FFC44F3850FA4A16542250CC4A1654224F38511451
S1239 8804C874E516E585A4 30E57B24202000A4898549E41EA00065D5E5E1C41EAFFE64F381A
S12398A050FA4A16542250CC4A1654224F38422A8954455354205445535497FC40684118D5
S12398C003E84C72414298FC95C64F3840A4074 359434C452023410A48604562542240A450
S12398E00920434F4D504C455445410A4F38951E4A164202000441884 1A4FFCE422A0000CE
S9030000FC
```

APPENDIX B

Defining running electrolytes and test samples requires the following command

Nx Ny Nz DEFxyz name<Cr> where:

N is the numeric value of the subscripted coordinate to be associated with "name". −15000<=-N<=15000 name is an alpha-numeric string of 20 characters or less, containing at least 1 alpha.

| | |
|---|---|
| EXAMPLE: | 500 100 20 DEFxyz RE1<Cr><br>Defines RE1 top be at the indicated X=500, Y=100, Z=20 position. |

NOTE:

The System Controller places no significance on the alpha-numeric string characters in "name". In the above example "RE1" is most likely a running electrolyte bottle. However, the character significance of the name is known to the System PC not the System Controller. To the System Controller, the string "RE1" is shorthand for the assigned coordinates.

The format for defining the liquid level sensor vs. "name" relationship is:

name N=GUAGE#<CR> where:

name is an alpha-numeric string, as defined above.

N is the level sensor number (1–4).

| | |
|---|---|
| EXAMPLE: | RE3 2 - GUAGE#<Cr><br>Instructs the System Controller to use the #2 level sensor anytime an operation on RE3 requires level information. |

To inform the System Controller which of the two plumbing systems in the replenishment system is associated with which running electrolyte bottle, the following format is used.

name N=PURGE#<Cr> where:

name is an alpha-numeric string previously defined

N is the plumbing identifier (1 or 2)

| | |
|---|---|
| EXAMPLE: | RE3 1 =PURGE#<Cr><br>Instructs the Sample Handler to use plumbing #1 when emptying RE3. |

To define which running electrolyte supply bottle is plumbed to which running electrolyte bottle, the following format is used.

name N=RESERVOIR#<CrLf> where:

name is an alpha-numeric string previously defined

N is the plumbing identifier (1 or 2)

| | |
|---|---|
| EXAMPLE: | RE4 1 =RESERVOIR#<CrLf><br>Instructs the System Controller to use the plumbing associated with the supply bottle #1 when filling RE4. |

After establishing names for the Running Electrolyte (RE) and the Test Sample (TS) coordinate definitions, the names assigned can be used to define the RE & TS for the next test.

The format for defining the Running Electrolyte (RE) is:

name =RE
Defines "name" as the Running Electrolyte
The format for defining the Test Sample (TS) is:
name =TS
Defines "name" as the Test Sample

| | |
|---|---|
| EXAMPLE: | RE4 =RE<Cr><br>Specifies that the Running Electrolyte be drawn from the location labeled RE4<br>Al =TS<Cr><br>Specifies that the Test Sample be drawn from the sample location labeled Al |

The format for establishing the asperation method to draw the sample into the capillary tube is:

Nv Nt type=ASPERATE<Cr> where:

type is one of two character strings, "VOLTS" or "VACUUM".

Nv is the value of the asperation force in units of mmHg (torr) for vacuum or volts for electromotive.

Nt is the time to apply the force in units of seconds.

| | |
|---|---|
| EXAMPLE: | 30000 20 VOLTS =ASPERATE<Cr><br>Defines the asperation to consist of applying 30 kv across the capillary for 20 seconds.<br>100 60 VACUUM - ASPERATE<Cr><br>Defines the asperation to consist of applying a 100 torr vacuum to the capillary tube for 60 seconds. |

Pretest Purge is a directive to empty a RE container at the beginning of a test, and would be generally be followed by a FILL directive. To establish this directive in the next test protocal, the following format is used:

Nv Nt name PREPURGE<Cr> where:

Nv is the vacuum level to use for the purge.

Nt is the time in seconds to apply the vacuum.

name is an alpha-numeric string defined above for the running electrolyte bottle and the associated plumbing.

The PREPURGE directive is not retained for subsequent tests. Consequently, all tests requiring a pretest purge must be so directed before the test is started.

| | |
|---|---|
| EXAMPLE: | 200 60 RE1 PREPURGE<Cr><br>Directs that RE1 be emptied before starting the next test, using a 200 torr vacuum for 60 seconds. |

Posttest purge follows the same format and operation as the Pretest purge using the directive POSTPURGE.

Nv Nt name POSTPURGE<Cr>

The posttest purge is performed at the end of the next test. After the purge is completed, the posttest directive is cleared as in the case of the PREPURGE.

The format for the FILL directive is:

name Nz FILL<Cr> where:

name is the alpha-numeric string defined above.

Nz is the vertical position to which the level sensor is to be lowered for gauging the fill level.

There are two modes for controlling the power across the capillary during a test:

1. VPROFILE, which specifies a voltage vs. time power control
2. ICONSTANT, which specifies a constant current value to be maintained during the test.

These modes are mutually exclusive. Transmitting a VPROFILE directive clears any previous ICONSTANT directive and any associated settings. The same is true when an ICONSTANT directive is transmitted: i.e., any previous VPROFILE directive and associated settings are cleared.

During the course of a test the applied voltage across the capillary tube can be programmed by the operator to change as a function of time. These voltage vs. time profiles are transmitted to the System Controller by the PC prior to starting a test. The profile information is transferred as voltage level, delta time information. That is, the voltage data transferred to the System Controller is the new voltage setting and the time data is the period of time over which the System Controller is to change from the currently running value to the new setting. The profile information is transmitted as a block of data using a directive followed by the data. A "−1" in the data stream marks the end of the profile settings. Anytime voltage profile settings are transmitted, the entire profile must be transmitted; one specific setting in the profile cannot be separately edited. The format for transferring the voltage profile is:

VPROFILE<Cr>
v1 t1<Cr>
v2 t2<Cr>
. . .
vn tn<Cr>
−1<Cr> where:

vn is the voltage level in volts
0< =vn< =30000 volts tn is the time interval in seconds within which to make the change to vn
0< =tn< =30000 seconds −1 is the end of data mark The maximum number of profile settings is limited to 50.

| | | |
|---|---|---|
| EXAMPLE: | VPROFILE<Cr> | |
| | 2000 0<Cr> | directs an initial step to 2000 volts |
| | 10000 30<Cr> | directs a 30 second up ramp from 2000 to 10000 volts |
| | 10000 60<Cr> | directs a hold at 10000 volts for 60 seconds |
| | 8000 0<Cr> | directs a step to 8000 volts |
| | 2000 30<Cr> | directs a 30 second down ramp to 2000 volts |
| | −1<Cr> | directs that the profile data is complete. |

The format of the constant current directive is:

Ni Nt ICONSTANT where:

Ni is the value of the constant current in microamps
50< =Ni< =500 microamps

Nt is the time interval of the test in second
0< =Nt< =15000 seconds

The format for defining a group of detector signals is:

n1 n2 n3 . . . Nd Ng=GROUP where:

n is a detector number (1-16)

Nd is the number of detector data signals in the group

Ng is the group # (1-4)

| | |
|---|---|
| EXAMPLE: | 10 1 2 =GROUP |
| | Defines group #2 to be 1 detector signal, detector 10. |
| | 8 9 10 10 11 12 6 3 =GROUP |
| | Defines group #3 to be 6 detector signals, wherein detector 10 is used twice. |

I claim:

1. A fluorescence and absorption detector comprising:

light source means for simultaneously providing a first light beam and a second light beam wherein said first and second light beams are simultaneously incident upon and interact with a sample and emerging light from such a sample is characteristic of said sample;

means, receiving said emerging light, for separating light into a number of different wavelengths wherein said emerging light is separated into different wavelengths; and means, receiving each of said different wavelengths from said means for separating light, for providing an output signal corresponding to each of said different wavelengths;

wherein said first light beam includes a wavelength of light causing such a sample to fluoresce and said second light beam includes a wavelength absorbed by such a sample;

said emerging light comprises unabsorbed light from said second light beam and fluorescent radiation; and a first subset of said output signals represent said flourescent radiation from such a sample and a second subset of said output signals represent said unabsorbed light from such a sample.

2. A detector as in claim 1 wherein said first light beam is incident upon a first region of such a sample and said second light beam is incident upon a second region of such a sample so that said beams are incident upon such a sample from different directions.

3. A detector as in claim 2 wherein said light source means for providing a first light beam comprises a xenon flash lamp.

4. A detector as in claim 2 wherein said light source means for providing a second light beam comprises a deuterium lamp.

5. A detector as in claim 2 further comprising a filter placed in the path of said first light beam so that light incident upon such a sample from said filter consists essentially of said wavelength which causes such a sample to fluoresce.

6. A detector as in claim 5 wherein said filter comprises approximately a 340 nanometer wavelength filter.

7. A detector as in claim 5 further comprising a first imaging system placed in the path of said first light beam wherein said first light beam is projected upon only a selected portion of said first region of such a sample.

8. A detector as in claim 7 wherein said first imaging system comprises a slit mask and a lens.

9. A detector as in claim 2 further comprising a second imaging system placed in the path of said second light beam wherein said second light beam is projected upon only a selected portion of said second region of such a sample.

10. A detector as in claim 9 wherein said second imaging system comprises a slit mask and a lens.

11. A detector as in claim 2 wherein said means for separating light receives emerging light from a sample at a first selected angle from said first light beam.

12. A detector as in claim 11 wherein said means for separating light receives emerging light from a sample at a second selected angle from said second light beam.

13. A detector as in claim 12 wherein said first selected angle is about 90°.

14. A detector as in claim 13 wherein said first selected angle is about 180°.

15. A detector as in claim 2 wherein said means for separating light comprises a grating.

16. A detector as in claim 15 wherein said output signal providing means comprises a photodiode array wherein said photodiode array receives light from said separating means.

17. A detector as in claim 16 further comprising a multiplicity of amplifiers, operatively connected to said diode array, each diode in said photodiode array receiving light from said separating means being operatively connected to one of said multiplicity of amplifiers.

18. A detector as in claim 17 wherein said first light beam is a pulsed light beam.

19. A detector as in claim 18 wherein said second light beam is a continuous light beam.

20. A detector as in claim 19 wherein a first subset of photodiodes of said photodiode array provide pulsed output signals in response to wavelengths from said grating corresponding to said fluorescence, and a second subset of photodiodes of said photodiode array provide continuous output signals in response to wavelengths from said grating corresponding to unabsorbed light from said second light beam.

21. A detector as in claim 20 wherein amplifiers for said first subset of photodiodes pass said pulsed signals and reject continuous signals, and amplifiers for said second subset of photodiodes pass said continuous signals and reject pulsed signals.

* * * * *